(12) United States Patent
Bielas et al.

(10) Patent No.: US 10,538,807 B2
(45) Date of Patent: Jan. 21, 2020

(54) COMPOSITIONS AND METHODS FOR DETECTING RARE NUCLEIC ACID MOLECULE MUTATIONS

(71) Applicant: Fred Hutchinson Cancer Research Center, Seattle, WA (US)

(72) Inventors: Jason H. Bielas, Seattle, WA (US); Sean D. Taylor, Kirkland, WA (US); Matthew T. Laurie, Olympia, WA (US)

(73) Assignee: Fred Hutchinson Cancer Research Center, Seattle, WA (US)

( * ) Notice: Subject to any disclaimer, the term of this patent is extended or adjusted under 35 U.S.C. 154(b) by 616 days.

(21) Appl. No.: 14/402,820

(22) PCT Filed: May 29, 2013

(86) PCT No.: PCT/US2013/043158
§ 371 (c)(1),
(2) Date: Nov. 21, 2014

(87) PCT Pub. No.: WO2013/181276
PCT Pub. Date: Dec. 5, 2013

(65) Prior Publication Data
US 2015/0133312 A1    May 14, 2015

Related U.S. Application Data

(60) Provisional application No. 61/783,815, filed on Mar. 14, 2013, provisional application No. 61/654,236, filed on Jun. 1, 2012.

(51) Int. Cl.
*C12Q 1/68* (2018.01)
*C12Q 1/6876* (2018.01)

(52) U.S. Cl.
CPC ..... *C12Q 1/6876* (2013.01); *C12Q 2600/156* (2013.01)

(58) Field of Classification Search
None
See application file for complete search history.

(56) References Cited

U.S. PATENT DOCUMENTS

| 5,741,678 A | 4/1998 | Ronai | |
| 2005/0053975 A1* | 3/2005 | Reddy | C12Q 1/683 435/6.12 |
| 2009/0181378 A1* | 7/2009 | Sanders | C12Q 1/6886 435/6.11 |

OTHER PUBLICATIONS

Fuery et al. (Clin Chem, 2000, 46:5, p. 620-624).*
Pekin et al. (Lab Chip, 2011, 11, p. 2156-2166).*
Ohashi et al. (Biomed Microdevices, 2007, 9:695-702).*
Doherty (Journal of Clinical Endocrinology & Metabolism, 2002, 87(3):1151-1155).*
Polymeropoulous et al. (Science, 1997, vol. 276, p. 2045-2047).*
Bielas et al. (Nature Methods, 2005, p. 1-6, IDS reference).*

(Continued)

*Primary Examiner* — Stephanie K Mummert
(74) *Attorney, Agent, or Firm* — Seed Intellectual Property Law Group LLP

(57) ABSTRACT

The present disclosure relates to compositions and methods for detecting rare nucleic acid molecule mutations in a plurality of nucleic acid molecules. Also disclosed are methods for determining the size of a nucleic acid molecule using droplet digital PCR.

24 Claims, 27 Drawing Sheets
Specification includes a Sequence Listing.

(56) References Cited

OTHER PUBLICATIONS

Asano et al. (Human Cancer Biology, 2006, 12(1):43-48) (Year: 2006).*
Matsuura et al. (Nature Genetics, 1997, vol. 15, p. 74-77) (Year: 1997).*
Beer et al., "On-Chip Single-Copy Real-Time Reverse-Transcription PCR in Isolated Picoliter Droplets," *Analytical Chemistry* 80(6):1854-1858, 2008.
Bielas et al., "Quantification of random genomic mutations," *Nature Methods* 2(4):285-290, 2005.
Brown et al., "Replication of mitochondrial DNA occurs by strand displacement with alternative light-strand origins, not via a strand-coupled mechanism," *Genes & Development* 19(20):2466-2476, 2005.
Buehler et al., "Rapid quantification of DNA libraries for next-generation sequencing," *Methods* 50(4):S15-S18, 2010.
Chabi et al., "Quantification of Mitochondrial DNA Deletion, Depletion, and Overreplication: Application to Diagnosis," *Clinical Chemistry* 49(8): 1309-1317, 2003.
Chang et al., "A microfluidic system for fast detection of mitochondrial DNA deletion," *Lab on a Chip* 11(16):2693-2700, 2011.
Chinault et al. "Application of dual-genome oligonucleotide array-based comparative genomic hybridization to the molecular diagnosis of mitochondrial DNA deletion and depletion syndromes," *Genetics in Medicine* 11(7):518-526, 2009.
Cortopassi et al., "Detection of a specific mitochondrial DNA deletion in tissues of older humans," *Nucleic Acids Research* 18(23):6927-6933, 1990.
Dressman et al., "Transforming single DNA molecules into fluorescent magnetic particles for detection and enumeration of genetic variations," *Proceedings of the National Academy of Sciences of the United States of America* 100(15):8817-8822, 2003.
Edgar et al., "Random Point Mutations with Major Effects on Protein-Coding Genes Are the Driving Force behind Premature Aging in mtDNA Mutator Mice," *Cell Metabolism* 10(2): 131-138, 2009.
Foury et al., "Yeast mitochondrial DNA mutators with deficient proofreading exonucleolytic activity," *The EMBO Journal* 11(7):2717-2726, 1992.
He et al., "Detection and quantification of mitochondrial DNA deletions in individual cells by real-time PCR," *Nucleic Acids Research* 30(14):e68, 2002. (6 pages).
Hindson et al., "High-Throughput Droplet Digital PCR System for Absolute Quantitation of DNA Copy Number," *Analytical Chemistry* 83(22):8604-8610, 2011.
Hori et al., "Uniform amplification of multiple DNAs by emulsion PCR," *Biochemical and Biophysical Research Communications* 352(2):323-328, 2007.
Horton et al., "Marked increase in mitochondrial DNA deletion levels in the cerebral cortex of Huntington's disease patients," *Neurology* 45(10):1879-1883, 1995.
Hwang et al., "Spectrum of mitochondrial DNA deletions within the Common Deletion region induced by low levels of UVB irradiation of human keratinocytes in vitro," *Gene* 440(1-2):23-27, 2009. (12 pages).
International Search Report and Written Opinion, dated Sep. 2, 2013, for International Application No. PCT/US2013/043158, 13 pages.
Kujoth et al., "Mitochondrial DNA Mutations, Oxidative Stress, and Apoptosis in Mammalian Aging," *Science* 309(5733):481-484, 2005. (5 pages).
Kwon et al., "Multiplex Ligation-Dependent Probe Amplification (MLPA) Assay for the Detection of Mitochondrial DNA Deletion in Chronic Progressive External Ophthalmoplegia (CPEO)," *Annals of Clinical & Laboratory Science* 41(4):385-389, 2011.
Li et al., "BEAMing up for detection and quantification of rare sequence variants," *Nature Methods* 3(2):95-97, 2006.
Linnarsson, "Recent advances in DNA sequencing methods—general principles of sample preparation," *Experimental Cell Research* 316(8):1339-1343, 2010.
Melov et al., "Marked increase in the Number and variety of mitochondrial DNA rearrangements in aging human skeletal muscle," *Nucleic Acids Research* 23(20):4122-4126, 1995.
Meyer et al., "From micrograms to picograms: quantitative PCR reduces the material demands of high-throughput sequencing," *Nucleic Acids Research* 36(1):e5, 2008. (6 pages).
Ottesen et al., "Microfluidic Digital PCR Enables Multigene Analysis of Individual Environmental Bacteria," *Science* 314(5804):1464-1467, 2006.
Pinheiro et al., "Evaluation of a Droplet Digital Polymerase Chain Reaction Format for DNA Copy Number Quantification," *Analytical Chemistry* 84(2):1003-1011, 2012.
Robinson et al., "Accurate prediction of repeat prostate biopsy outcomes by a mitochondrial DNA deletion assay," *Prostate Cancer and Prostatic Diseases* 13(2):126-131, 2010.
Ruiz-Pesini et al., "An enhanced MITOMAP with a global mtDNA mutational phylogeny," *Nucleic Acids Research* 35(Database):D823-D828, 2007.
Song et al., "Replication Pauses of the Wild-Type and Mutant Mitochondrial DNA Polymerase Gamma: A Simulation Study," *PLoS Computational Biology* 7(11):e1002287, 2011. (9 pages).
Spelbrink et al., "In Vivo Functional Analysis of the Human Mitochondrial DNA Polymerase POLG Expressed in Cultured Human Cells," *The Journal of Biological Chemistry* 275(32):24818-24828, 2000. (12 pages).
Sudmant et al., "Diversity of Human Copy Number Variation and Multicopy Genes," *Science* 330(6004):641-646, 2010. (7 pages).
Trifunovic et al., "Premature ageing in mice expressing defective mitochondrial DNA polymerase," *Nature* 429(6990):417-423, 2004.
Valasek et al., "The power of real-time PCR," *Advances in Physiology Education* 29(3):151-159, 2005.
Vermulst et al., "DNA deletions and clonal mutations drive premature aging in mitochondrial mutator mice," *Nature Genetics* 40(4):392-394, 2008.
Vermulst et al., "Mitochondrial point mutations do not limit the natural lifespan of mice," *Nature Genetics* 39(4):540-543, 2007.
Vermulst et al., "Quantification of random mutations in the mitochondrial genome," *Methods* 46(4):263-268, 2008. (13 pages).
Warren et al., "Transcription factor profiling in individual hematopoietic progenitors by digital RT-PCR," *Proceedings of the National Academy of Sciences of the United States of America* 103(47):17807-17812, 2006.
White, III et al., "Digital PCR provides sensitive and absolute calibration for high throughput sequencing," *BMC Genomics* 10:116, 2009. (12 pages).
Xiao et al., "Role of Excess Inorganic Pyrophosphate in Primer-Extension Genotyping Assays," *Genome Research* 14(9):1749-1755, 2004.
Yun et al., "Genomic DNA functions as a universal external standard in quantitative real-time PCR," *Nucleic Acids Research* 34(12):e85, 2006. (10 pages).
Zhang et al., "A novel real-time quantitative PCR method using attached universal template probe," *Nucleic Acids Research* 31(20):e123, 2003. (8 pages).
Bielas, "Digital Detection of Ultra-Rare Nuclear and Mitochondrial Mutations: Fundamental and Clinical Implications in Cancer and Disease, Digital PCR Short Course," PowerPoint presentation, Molecular Med Tri-Con, Feb. 2012, Cambridge Healthtech Institute, San Francisco, CA, 44 pages.
Laurie et al., "Simultaneous digital quantification and Fluorescence-based size characterization of massively parallel sequencing libraries," *BioTechniques* 55(2):61-67, 2013.
Taylor et al., "Targeted enrichment and high-resolution digital profiling of mitochondrial DNA deletions in human brain," *Aging Cell* 13:29-38, 2014.

* cited by examiner

| Sample ID | Control Region | | | Major arc | | | | | $O_L$ | | | Measured Deletion Frequency | |
|---|---|---|---|---|---|---|---|---|---|---|---|---|---|
| | Dilution factor | Positive droplet counts | Negative droplet counts | molecules /μl | Dilution factor | Positive droplet counts | Negative droplet counts | molecules /μl | Dilution factor | Positive droplet counts | Negative droplet counts | Molecules /μl | Major arc | $O_L$ |
| WT1 | 10000 | 18243 | 6974 | 1410 | 1 | 512 | 24001 | 23.2 | 1 | 6 | 20586 | 0.32 | 1.65E-06 | 2.27E-08 |
| WT2 | 10000 | 12434 | 13505 | 717 | 1 | 37 | 24976 | 1.63 | 1 | 2 | 24253 | 0.0906 | 2.27E-07 | 1.26E-08 |
| WT3 | 10000 | 18396 | 7481 | 1360 | 1 | 44 | 23965 | 2.02 | 1 | 5 | 23112 | 0.238 | 1.49E-07 | 1.75E-08 |
| mut1 | 10000 | 7490 | 19730 | 354 | 1 | 468 | 18957 | 26.8 | 1 | 86 | 23844 | 3.96 | 7.57E-06 | 1.12E-06 |
| mut2 | 10000 | 12235 | 13976 | 691 | 1 | 674 | 25457 | 28.7 | 1 | 145 | 26094 | 6.09 | 4.15E-06 | 8.81E-07 |
| mut3 | 10000 | 9178 | 17062 | 473 | 1 | 523 | 22302 | 25.5 | 1 | 120 | 26201 | 5.02 | 5.39E-06 | 1.06E-06 |

*Fig. 3*

| SampleID | Control Region | | | | | Minor arc | | | | Measured Deletion Frequency |
|---|---|---|---|---|---|---|---|---|---|---|
| | Dilution factor | Positive droplet counts | Negative droplet counts | molecules /µl | Dilution factor | Positive droplet counts | Negative droplet counts | molecules /µl | | |
| -dox 1 | 3000 | 13127 | 1050 | 2860 | 1 | 83 | 11374 | 7.99 | | 9.30E-07 |
| -dox 2 | 3000 | 11810 | 1158 | 2650 | 1 | 90 | 14023 | 7.03 | | 8.80E-07 |
| -dox 3 | 3000 | 12836 | 724 | 3220 | 1 | 87 | 13072 | 7.29 | | 7.50E-07 |
| +dox 1 | 3000 | 11012 | 913 | 2820 | 1 | 297 | 11413 | 28.2 | | 3.33E-06 |
| +dox 2 | 3000 | 12303 | 1174 | 2680 | 1 | 289 | 11077 | 28.3 | | 3.52E-06 |
| +dox 3 | 3000 | 11152 | 702 | 3110 | 1 | 356 | 12568 | 30.7 | | 3.29E-06 |

Fig. 4

COMPOSITIONS AND METHODS FOR DETECTING RARE NUCLEIC ACID MOLECULE MUTATIONS

CROSS REFERENCE TO RELATED APPLICATIONS

This application claims the benefit under 35 U.S.C. § 119(e) to U.S. Provisional Application No. 61/654,236 filed on Jun. 1, 2012, and U.S. Provisional Application No. 61/783,815 filed on Mar. 14, 2013 which applications are incorporated by reference herein in their entirety.

STATEMENT OF GOVERNMENT INTEREST

This invention was made with government support under ES019319 awarded by the National Institutes of Health and W81XWH-10-1-0563 awarded by the U.S. Army Medical Research and Material Command. The government has certain rights in this invention.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 360056_408WO_SEQUENCE_LISTING.txt. The text file is 5 KB was created on May 29, 2013 and is being submitted electronically via EFS-Web.

BACKGROUND

Technical Field

The present disclosure relates to compositions and methods for detecting rare nucleic acid molecule mutations in a plurality of nucleic acid molecules.

Description of the Related Art

Mitochondria are multifunctional, essential organelles that play a key role in vital cellular processes such as oxidative phosphorylation (OXPHOS), cellular metabolism, calcium storage and regulation of apoptosis (Scheffler, I. E., *Mitochondria*, $2^{nd}$ ed., Wiley-Liss, 2008). Whereas most mitochondrial proteins are encoded in the nucleus, synthesized in the cytosol and subsequently imported into the mitochondria, a subset of genes encoding crucial subunits of the major OXPHOS complexes are encoded within the mitochondria itself on a multi-copy, circular genome.

Maintenance of the mitochondrial genome(s) is crucial for proper organelle function. Accumulated defects, including point mutations, deletions, and rearrangements, can lead to mitochondrial dysfunction and are known to cause a number of mitochondrial disorders (Greaves et al., 2012, J. Pathol. 226:274-286). Large-scale deletions (spanning hundreds to thousands of basepairs) in mtDNA are increasingly associated with a wide variety of pathologies and diseases, including neuromuscular and mitochondrial deletion syndromes (Chinnery, P. F. in *Gene Reviews* eds. R A. Pagon, T. D. Bird, C. R. Dolan & K. Stephens, 1993), neuropsychiatric disorders (Kato et al., 2011, Neurosci. Res. 69:331-336), Huntington's disease (Horton et al., 1995, Neurology 45:1879-1883), and a growing number of cancers (Lee et al., 2010, Ageing Res. Rev. 9:S47-58). Furthermore, mitochondrial deletions are known to accumulate with age and are thought to be an important driving force in mammalian aging (Trifunovic et al., 2004, Nature 428:417-423; Vermulst et al., 2008, Nat. Genet. 40:392-394; Cortopassi & Arnheim, 1990, Nuc. Acids Res. 18:6927-6933).

While mechanisms for large-scale mtDNA deletions have been proposed (Foury et al, 2004, Cell. Mol. Life. Sci. 61:2799-2811; Krishnan et al., 2008, Nat. Genet. 40:275-279; Song et al., 2011, PLoS Comp. Biol. 7:31002287), they have not been tested in vivo. One of the key difficulties to testing these hypotheses is a lack of sensitive assays that can detect de novo deletions and trace the kinetics of clonal expansion. De novo mtDNA deletions are relatively rare events, occurring with frequencies that are thought to be as low as 1 deletion per million genomes. Furthermore, even though specific deletions are known causes of neuromuscular disorders, this same lack of assay sensitivity has also precluded the use of mtDNA deletions as biomarkers for disease. For example, Kearns-Sayre Syndrome is a mitochondrial deletion disorder caused by accumulation of a large deletion in the mtDNA, typically between nucleotides 8470 and 13446 (the so-called "common deletion") (Di-Mauro S. & Hirano, M. in *Gene Reviews* eds. A. Pagon, T. D. Bird, C. R. Dolan, & K. Stephens, 1993). While the pathogenic deletion is present in all tissues, particularly in skeletal muscle, the measured frequency in blood is low, presumably due to strong selection against dysfunctional genomes in proliferating hematopoietic cells. For this reason, the pathogenic deletion is difficult to detect in patient blood samples using current methods, precluding the use of the deletion as a convenient biomarker for early detection of the disease.

BRIEF SUMMARY

In one aspect, the present disclosure provides a method for detecting nucleic acid molecules comprising a rare mutation, comprising: a) contacting a plurality of nucleic acid molecules with a first restriction endonuclease, wherein the first restriction endonuclease is capable of cleaving a nucleic acid molecule comprising a first target region having a site specific for the first restriction endonuclease, and wherein the nucleic acid molecule is not cleaved by the first restriction endonuclease when the first target region comprises a mutation that alters the site specific for the first restriction endonuclease; b) amplifying the mutated first target region from the plurality of nucleic acid molecules of step (a) with a first 5' primer and a first 3' primer, wherein the primers are complementary to nucleic acid sequences flanking the first target region on a nucleic acid molecule, and wherein only the mutated first target region is substantially amplified; and c) quantifying the amplified amount of mutated first target region, thereby detecting a rare mutation within a plurality of nucleic acid molecules.

In further aspects, the nucleic acid molecule comprising a mutated target region may be a genomic DNA molecule or a mitochondrial DNA molecule.

In still further aspects, the methods of the present disclosure may be used to detect mutations associated with chronic myelogenous leukemia, Huntington's disease, Kearns-Sayre syndrome, Pearson syndrome, or chronic progressive external ophthalmoplegia.

In another aspect, the present disclosure provides a method for determining the size of a nucleic acid molecule, comprising: a) amplifying a nucleic acid molecule using droplet digital PCR to produce a target amplicon; b) measuring the fluorescence value of a positive droplet containing the target amplicon; and c) comparing the fluorescence value of the positive droplet containing the target amplicon to the fluorescence values of at least two control amplicons of known size, thereby determining the size of the nucleic acid molecule.

These and other aspects of the present invention will become apparent upon reference to the following detailed description and attached drawings. All references disclosed herein are hereby incorporated by reference in their entirety as if each was incorporated individually.

BRIEF DESCRIPTION OF THE SEVERAL VIEWS OF THE DRAWINGS

FIG. 3. ddPCR data on the deletion frequency of Polga$^{+/+}$ and Polga$^{-/-}$ knock-in mice at the major arc target region and the $O_L$ target region.

FIG. 4. ddPCR data on the deletion frequency of HeLa cells expressing D274A exo$^-$ pol γ variant.

DETAILED DESCRIPTION

Figure 1A:
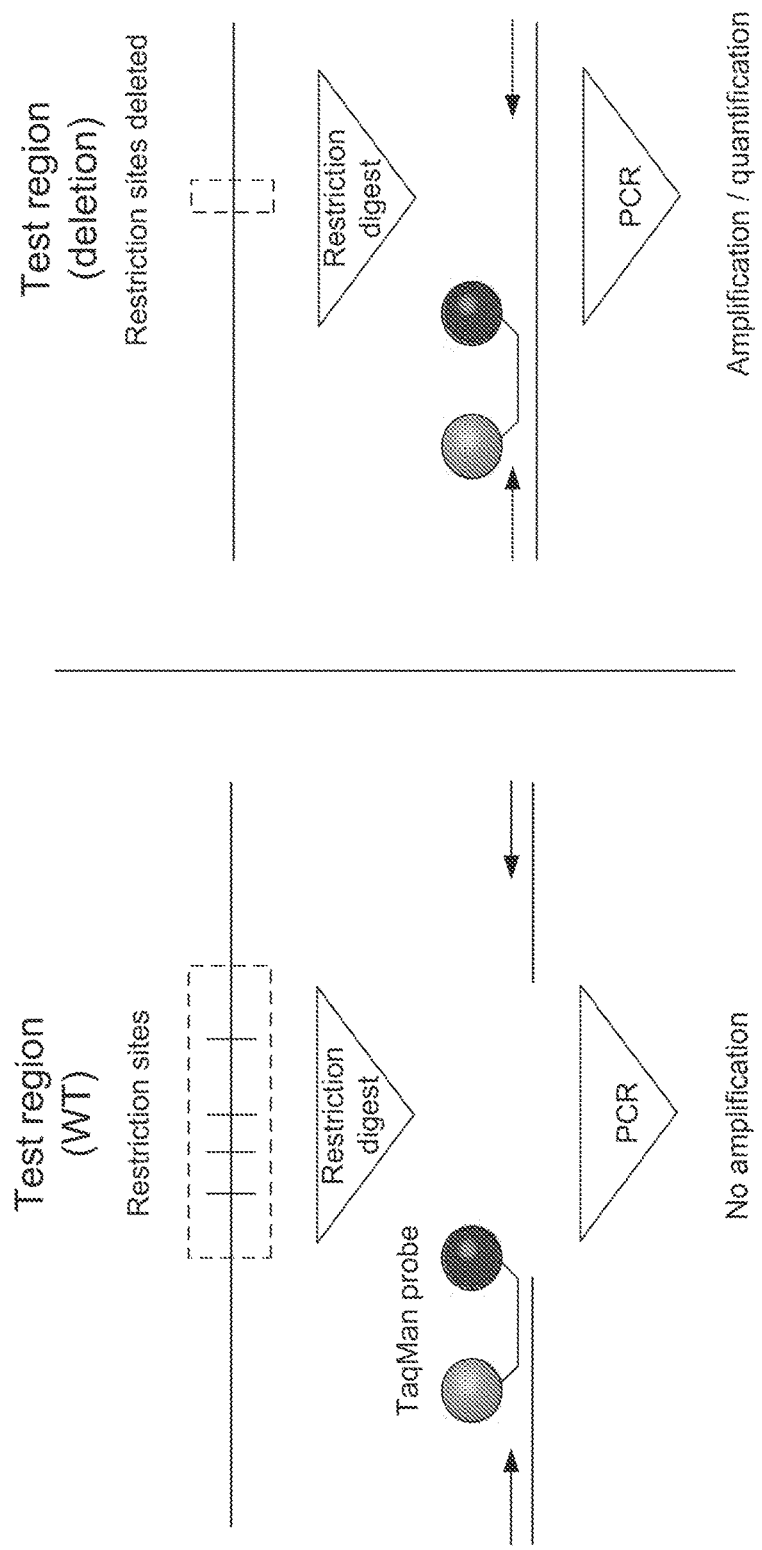
FIG. 1. Overview of Digital Deletion Detection (3D). (A) Selective detection and amplification of deletion-bearing molecules. WT molecules harbor endonuclease recognition sites within the target region. Upon digestion, the target is cleaved, making the WT molecule unsuitable as a template for PCR amplification. In contrast, mutant molecules that harbor deletions that remove the restriction recognition sites are resistant to digestion. These molecules serve as templates for PCR amplification. The presence of the TaqMan® hydrolysis probe allows for detection and enumeration of each molecule in the sample bearing the appropriate deletion. (B) Mutant target molecules (depicted as an idealized, unbroken circular chromosome) are individually sequestered into 1 nl water-in-oil droplets along with TaqMan® PCR chemistry and target-specific TaqMan® probes. Droplets are thermally cycled. Since the average number of molecules per droplet is less than one, positive droplets (dark gray) represent individual reaction vessels for single molecule quantitative PCR amplification. Droplets are individually scanned, and scored as positive or negative, thus providing a digital quantification of all deletion-bearing molecules within the sample. Alternatively, droplets can be disrupted and the amplification products subjected to physical characterization, e.g., gel electrophoresis, cloning, sequencing, or other applications.

The instant disclosure provides methods for interrogation of a specific target region on a nucleic acid molecule, among a plurality of nucleic acid molecules, in order to detect mutations (e.g., deletions) present within the target region. The disclosed methods involve targeted destruction of nucleic acid molecules bearing wild-type target regions via restriction endonuclease followed by quantitative amplification of intact mutant target regions.

In one aspect, the present disclosure provides a method for detecting rare nucleic acid molecule mutations by contacting a plurality of nucleic acid molecules with a first restriction endonuclease that is capable of cleaving a nucleic acid molecule comprising a first target region having a site specific for the first restriction endonuclease and wherein the nucleic acid molecule is not cleaved by the first restriction endonuclease when the first target region comprises a mutation that alters the site specific for the first restriction endonuclease. The mutated first target region from the plurality of nucleic acid molecules of the restriction endonuclease digestion step is then amplified with a first 5' primer and a first 3' primer, wherein the primers are complementary to nucleic acid sequences that flank the first target region on a nucleic acid molecule, wherein only the mutated first target region is substantially amplified. Finally, the amplified amount of the mutated first target region is quantified, thereby detecting a rare mutation within a plurality of nucleic acid molecules.

Additionally, this disclosure provides methods for determining the size of a nucleic acid molecule using droplet digital PCR. Such methods are useful, for example, for sample preparation in next generation sequencing techniques.

Prior to setting forth this disclosure in more detail, it may be helpful to an understanding thereof to provide definitions of certain terms to be used herein. Additional definitions are set forth throughout this disclosure.

In the present description, the terms "about" and "consisting essentially of" mean±20% of the indicated range, value, or structure, unless otherwise indicated. It should be understood that the terms "a" and "an" as used herein refer to "one or more" of the enumerated components. The use of the alternative (e.g., "or") should be understood to mean either one, both, or any combination thereof of the alternatives. As used herein, the terms "include," "have" and "comprise" are used synonymously, which terms and variants thereof are intended to be construed as non-limiting.

A "nucleic acid molecule" refers to a single- or double-stranded linear or circular polynucleotide containing either deoxyribonucleotides or ribonucleotides that are linked by 3'-5'-phosphodiester bonds. A nucleic acid molecule includes a genomic DNA molecule or a mitochondrial DNA molecule.

A "nucleic acid molecule mutation" or "mutation" refers to a change in the nucleotide sequence of a nucleic acid molecule. A mutation may be caused by radiation, viruses, transposons, mutagenic chemicals, errors that occur during meiosis or DNA replication, or hypermutation. A mutation can result in several different types of change in sequence, including substitution, insertion or deletion of nucleotide(s).

A "spectrum of mutations" refers to a range of mutations that are present or detected in a sample derived from a host organism (including prokaryotic and eukaryotic organisms).

Mutations characteristics that may be interrogated when determining mutation spectrum include size, frequency, sequence, location, breakpoints, type of mutation, or type of nucleic acid molecule mutated.

A "restriction endonuclease" or "restriction enzyme" refers to an enzyme that cuts or cleaves nucleic acids at a specific recognition nucleotide sequence known as restriction or recognition site. Recognition sites usually vary between 4 and 8 nucleotides, and many of them are palindromic. Restriction endonucleases and their specific recognition sites are well known in the art and are widely commercially available.

A "target region" refers to a pre-defined region of a nucleic acid molecule (e.g., genomic DNA molecule or mitochondrial DNA molecule), which contains a known or suspected rare mutation, preferably a deletion. A target region is generally from about 100 by to about 15,000 by in length. In certain embodiments, a target region is from about 500 by to about 5,000 by in length. A target region may contain one or more mutations or deletions of varying sequence and size. A restriction endonuclease is selected such that at least one restriction site for that restriction endonuclease, preferably two or more restriction sites, is contained within the target region. A pair of primers is designed to be specific for nucleic acid sequences that flank the target region. The selected restriction endonuclease cleaves nucleic acid molecules containing at least one restriction site (e.g., wild type molecules), thus preventing PCR amplification of the target region with the flanking primers. However, if a mutation (e.g., a deletion) is present in the target region that alters the restriction site, the target region between the primers remains intact, thus allowing for selective amplification of only the mutation-bearing molecules. A target region may contain restriction sites for multiple restriction endonucleases. A nucleic acid molecule may have more than one target region. A selected endonuclease may have multiple restriction sites within a target region, outside the target region, and within multiple target regions on a nucleic acid molecule.

As used herein, "amplifying" refers to production of multiple copies of a nucleic acid molecule, such as by PCR.

As used herein, "digital PCR" refers to an assay that provides an end-point measurement that provides the ability to quantify nucleic acids without the use of standard curves, as is used in real-time PCR. In a typical digital PCR experiment, the sample is randomly distributed into discrete partitions, such that some contain no nucleic acid template and others contain one or more template copies. The partitions are amplified to the terminal plateau phase of PCR (or end-point) and then read to determine the fraction of positive partitions. If the partitions are of uniform volume, the number of target DNA molecules present may be calculated from the fraction of positive end-point reactions using Poisson statistics, according to the following equation:

$$\lambda = -\ln(1-p) \quad (1)$$

wherein $\lambda$ is the average number of target DNA molecules per replicate reaction and p is the fraction of positive end-point reactions. From $\lambda$, together with the volume of each replicate PCR and the total number of replicates analyzed, an estimate of the absolute target DNA concentration is calculated. Digital PCR includes a variety of formats, including droplet digital PCR, BEAMing (beads, emulsion, amplification, and magnetic), and microfluidic chips.

"Droplet digital PCR" (ddPCR) refers to a digital PCR assay that measures absolute quantities by counting nucleic acid molecules encapsulated in discrete, volumetrically defined, water-in-oil droplet partitions that support PCR amplification (Hinson et al., 2011, Anal. Chem. 83:8604-8610; Pinheiro et al., 2012, Anal. Chem. 84:1003-1011). A single ddPCR reaction may be comprised of at least 20,000 partitioned droplets per well.

"BEAMing" (beads, emulsion, amplification, and magnetic) refers to a digital PCR format based on emulsion PCR, where templates are clonally amplified in the presence of magnetic beads. Post-PCR, the emulsion is broken to recover the beads, which are subsequently labeled with a fluorescent hybridization probe and read by conventional flow-cytometry (Dressman et al., Proc. Natl. Acad. Sci. USA, 2003, 100:8817-8822; Diehl et al., 2006, Nat. Methods 3:95-97).

"Microfluidic digital PCR" or "microfluidic chip" refers to a digital PCR format wherein the sample is split into hundreds of nanoliter partitions on an array or chip (Warren et al., 2006, Proc. Natl. Acad. Sci. USA 103:17807-17812; Ottesen et al., 2006, Science 314:1464-1467). A microfluidic chip also use water-in-oil droplets in a combined format, as is described in Beer et al., 2008, Anal. Chem. 80:1854-1858.

A "droplet" or "water-in-oil droplet" refers to an individual partition of the droplet digital PCR assay. A droplet supports PCR amplification of template molecule(s) using homogenous assay chemistries and workflows similar to those widely used for real-time PCR applications (Hinson et al., 2011, Anal. Chem. 83:8604-8610; Pinheiro et al., 2012, Anal. Chem. 84:1003-1011).

A "fluorogenic probe" comprises an oligonucleotide "probe" sequence labeled with both a "fluorescent reporter dye", or "fluorophore", and a "quencher dye", or "quencher." A "fluorescent reporter dye" or "fluorophore" refers to a molecule that emits light of a certain wavelength after having first absorbed light of a specific, but shorter, wavelength, wherein the emission wavelength is always higher than the absorption wavelength. A "quencher dye" "quencher" refers to a molecule that accepts energy from a fluorophore in the form of light at a particular wavelength and dissipates this energy either in the form of heat (e.g., proximal quenching) or light of a higher wavelength than emitted from the fluorophore (e.g., FRET quenching). Quenchers generally have a quenching capacity throughout their absorption spectrum, but they perform best close to their absorption maximum. For example, Deep Dark Quencher II absorbs over a large range of the visible spectrum and, consequently, efficiently quenches most of the commonly used fluorophores, especially those emitting at higher wavelengths (like the Cy® dyes). Similarly, the Black Hole Quencher family covers a large range of wavelengths (over the entire visible spectrum and into the near-IR). In contrast, Deep Dark Quencher I and Eclipse® Dark Quencher effectively quench the lower wavelength dyes, such as FAM, but do not quench very effectively those dyes that emit at high wavelengths.

As used herein, a "nucleic acid molecule primer" or "primer" and variants thereof refers to short nucleic acid sequences that a DNA polymerase can use to begin synthesizing a complementary DNA strand of the molecule bound by the primer. A primer sequence can vary in length from 5 nucleotides to about 50 nucleotides in length, from about 10 nucleotides to about 35 nucleotides, and preferably are about 15, 16, 17, 18, 19, 20, 21, 22, 23, 24, 25, 26, 27, 28, 29, 30, 31, 32, 33, 34, or 35 nucleotides in length. In certain embodiments, a nucleic acid molecule primer that is complementary to a target nucleic acid of interest can be used to initiate an amplification reaction, a sequencing reaction, or both.

An "amplicon" refers to a nucleic acid fragment formed as a product of natural or artificial amplification events or techniques. For example, an amplicon can be produced by PCR, ligase chain reaction, or gene duplication.

A "target amplicon" refers to an amplicon formed using a nucleic acid molecule of interest (e.g., from a patient sample, from a nucleic acid library, from a ligation reaction) as template.

As used herein, "next generation sequencing" (NGS) or "massive parallel sequencing" refers to high-throughput sequencing methods that allow the sequencing of thousands or millions of molecules in parallel. Examples of next generation sequencing methods include sequencing by synthesis, sequencing by ligation, sequencing by hybridization, polony sequencing, ion semiconductor sequencing, and pyrosequencing. By attaching primers to a solid substrate and a complementary sequence to a nucleic acid molecule, a nucleic acid molecule can be hybridized to the solid substrate via the primer and then multiple copies can be generated in a discrete area on the solid substrate by using polymerase to amplify (these groupings are sometimes referred to as polymerase colonies or polonies). Consequently, during the sequencing process, a nucleotide at a particular position can be sequenced multiple times (e.g., hundreds or thousands of times)—this depth of coverage is referred to as "deep sequencing."

Methods for Detecting Nucleic Acid Molecules Comprising a Rare Mutation

By way of background, currently the two most common clinical assays employed to detect pathogenic mtDNA deletions are variations on Southern blotting and long PCR (Cortopassi & Arnheim, 1990, Nucleic Acids Res. 18:6927-6933; Spelbrink et al., 2000, J. Biol. Chem. 275:24818-24828; Chang et al., 2011, Lab on a chip 11:2693-2700; He et al., 2002, Nucleic Acids Res. 30:e68; Chinault et al., 2009, Genet. Med. 11:518-526; Melov et al., 1995, Nucleic Acids Res. 23:4122-4126; Kwon et al., 2011, Anals of clinical and laboratory science 41:385-389). Although Southern blotting is highly specific, its low sensitivity means that deletions are difficult to detect until well after they have expanded to high levels within the cells and tissues. While traditional PCR-based assays offer some advantages over Southern blotting in that they are far more sensitive to low levels of deletions, few studies could be found that report deletions which occurred at frequencies less than a few percent, and only one purported to achieve sensitivities of 1 in ten thousand (Hwang et al., 2009, Gene 440:23-27). Additionally, given that larger deletions result in smaller amplification products that are preferentially amplified, traditional PCR-based assays will show a strong bias towards detection of large deletions to the exclusion of small deletions within a heterogeneous population. In recent years, real-time quantitative PCR (QPCR) has emerged as a means for both sensitive detection and quantification of mitochondrial deletions (Vermulst et al., 2008, Methods 46:263-268; Bielas & Loeb, 2005, Nat. Methods 2:285-290; Chabi et al, 2003, Clinical Chemistry 49:1309-1317; Robinson et al., 2010, Prostate cancer and prostatic diseases 13:126-131). While offering more consistent gains in sensitivity, QPCR relies on comparisons to standard curves. As such, it is better suited for measuring fold changes rather than absolute quantification of deletion frequencies. Furthermore, the relatively high background of wildtype (WT) DNA reduces both the precision and specificity of the detection probes (Hindson et al, 2011, Anal. Chem. 83:8604-8610).

Disclosed herein is a method for detection, quantification, and analysis of rare nucleic acid mutations, including genomic and mtDNA deletion events. One embodiment of this method, termed Digital Deletion Detection (3D), allows direct detection, quantification and characterization rare site-specific deletions that occur at frequencies as low as 1 deletion per $10^7$ genomes. 3D is adaptable to any organism, and can be used to interrogate multiple sites within the genome to look for both random and specific mutations (e.g., deletions).

In certain embodiments, the present disclosure provides a method for detecting rare nucleic acid mutations, comprising: a) contacting a plurality of nucleic acid molecules with a first restriction endonuclease, wherein the first restriction endonuclease is capable of cleaving a nucleic acid molecule comprising a first target region having a site specific for the first restriction endonuclease, and wherein the nucleic acid molecule is not cleaved by the first restriction endonuclease when the first target region comprises a mutation that alters the site specific for the first restriction endonuclease; b) amplifying the mutated first target region from the plurality of nucleic acid molecules of step (a) with a first 5' primer and a first 3' primer, wherein the primers are complementary to nucleic acid sequences flanking the first target region on a nucleic acid molecule, wherein only mutated first target region is substantially amplified; and c) quantifying the amplified amount of mutated first target region, thereby detecting a rare mutation within a plurality of nucleic acid molecules.

A nucleic acid molecule is any nucleic acid molecule in which detection of a mutation is desirable, including genomic DNA, mitochondrial DNA, or mRNA. In certain embodiments, a nucleic acid molecule is genomic DNA. In other embodiments, a nucleic acid molecule is mitochondrial DNA. Methods for isolating nucleic acid molecules for use in the methods described herein are well known in the art.

In certain embodiments, a mutation is a deletion of one or more nucleotides. In other embodiments, a mutation is an insertion or substitution of one or more nucleotides. A mutation may also include rearrangements of large segments of nucleotides, such as chromosomal translocations, inversions, or duplications. For mRNA, a mutation may result from alternative splicing events, such as deletion of one or more exons or usage of alternative splice sites. The disclosed methods may be used to detect any mutation that would alter at least one restriction site within a target region. Alteration of a restriction site includes deletion, substitution, or insertion of nucleotides within the restriction site sequence, as well as deletion or substitution of the entire restriction site sequence.

A "target region" refers to a pre-defined region of a nucleic acid molecule (e.g., genomic DNA molecule or mitochondrial DNA molecule), which contains a known or suspected rare mutation. A target region is generally from about 100 by to about 15,000 by in length. In certain embodiments, a target region is from about 500 by to about 5,000 by in length. A restriction endonuclease is selected such that at least one restriction site for the restriction endonuclease is contained within the target region. In certain embodiments, a restriction endonuclease has two or more restriction sites within a target region. In some embodiments, a restriction endonuclease has three or more restriction sites within a target region. One or more mutations may alter the same restriction site within a target region. Two or more mutations may alter different restriction sites of the endonuclease located within a target region. Therefore, mutations that are identified within a first target region using the methods disclosed herein may or may not be identical; for example, mutations may differ in size, breakpoints, location, and sequence. A target region may be large enough that it encompasses mutations in different locations within the target region, which may or may not overlap. Thus, within a plurality of nucleic acid molecules, a first restriction endonuclease is capable of cleaving a nucleic acid molecule comprising a first target region having a restriction site of the first restriction endonuclease, and a nucleic acid molecule is not cleaved by the first restriction endonuclease when the first target region comprises a mutation that alters the restriction site of the first restriction endonuclease.

In certain embodiments, a composition comprising a plurality of nucleic acid molecules may be obtained from a human subject. In other embodiments, a composition comprising a plurality of nucleic acid molecules may be obtained from other subjects, including prokaryotic and eukaryotic organisms. Prokaryotic organisms include bacteria and bacteria. Eukaryotic organisms include protozoa, algae, plants, slime molds, fungi (e.g., yeast), and animals. Animal organisms include mammals, such as primate, cow, dog, cat, rodent (e.g., mouse, rat, guinea pig), rabbit, or non-mammals, such as nematodes, bird, amphibian, reptile, or fish. A plurality of nucleic acid molecules may be from any sample from a subject, including a blood sample, a tumor sample, a tissue biopsy sample, a sputum sample, or a urine sample. In certain embodiments, a plurality of nucleic acid molecules consists essentially of a single type of nucleic acid molecule, e.g., genomic DNA or mtDNA. In other embodiments, a plurality of nucleic acid molecules consists essentially of more than one type of nucleic acid molecule, e.g., a mixture of genomic DNA and mtDNA. A plurality of nucleic acid molecules may include nucleic acid molecules from a variety of cells, tissues, organs, and sources within a subject, including tumor and normal tissues; maternal and fetal tissues; wild type and mutant cells.

Following endonuclease treatment of a plurality of nucleic acid molecules with a first restriction endonuclease, mutated first target region from the plurality of nucleic acid molecules is amplified with a first 5' primer and first 3' primer, wherein the primers are complementary to nucleic acid sequences that flank the first target region on a nucleic acid molecule. Methods for designing primers are well known in the art, and programs for selecting PCR primers are readily available, including Primer3, NCBI's Primer-BLAST, OligoPerfect™, or QuantPrime. Only a mutated first target region is substantially amplified, whereas a "non-mutated" first target region having a site specific for the first restriction endonuclease is not substantially amplified due to cleavage of the PCR template. Amplification may be performed using a variety of quantifying PCR methods, including digital PCR platforms. In certain embodiments, amplification is performed using droplet digital PCR (Hindson et al., 2011, Anal. Chem. 83:8604-8610; Pinheiro et al., 2012, Anal. Chem. 84:1003-1011; both references are hereby incorporated by reference in their entirety). In other embodiments amplification is performed using BEAMing (beads, emulsion, amplification, magnetic) or microfluidic chips (Dressman et al., Proc. Natl. Acad. Sci. 2003, 100: 8817-8822; Warren et al., 2006, Proc. Natl. Acad. Sci. USA 103:17807-17812). The partitions (discrete reaction compartments) where amplification occurs may be water-in-oil droplets or microfluidic chambers, depending on the digital PCR platform. In other embodiments, amplification occurs in 1 nl water-in-oil emulsion droplets. In further embodiments, a water-in-oil droplet also comprises a magnetic bead (for BEAMing platform).

In certain embodiments, the concentration nucleic acid molecules within partitions is adjusted to a level where most of the partitions contain no mutant template copies (e.g., amplified target region), while a small fraction of the partitions contain at least one mutant template copy. In certain embodiments, final concentration of a plurality of nucleic acid molecules following cleavage by an endonuclease is adjusted to yield an amount of positive molecules (e.g., amplified target region) per µl within the range of linearity for the Poisson calculation. Methods for determining final concentration the range of linearity for the Poisson calculation have been described in Pinheiro et al., 2012, Anal. Chem. 84:1003-1011 (incorporated by reference in its entirety). In a further embodiment, concentration of a plurality of nucleic acid molecules following cleavage by an endonuclease is adjusted to yield less than 3500 positive molecules per µl.

Amplification is performed to the terminal plateau phase of PCR. To quantify the amplified amount of mutated first target region, partitions (e.g., droplets) containing amplified target region template (positives) are distinguished from partitions that do not (negative). Detection of amplified mutated first target region may be accomplished by a variety of fluorescent labeled primers or probes that have been developed for real-time PCR. In certain embodiments, fluorogenic probes, such as TAQMAN® probes, are used during the amplification step for detection of amplified mutated first target regions (positives). In other embodiments, fluorescently labeled primers, such as LUX® or SCORPION® primers, are used during the amplification step for detection of amplified mutated first target regions (positives). In yet other embodiments, dyes with increased fluorescence when bound to double stranded DNA, such as intercalator or minor-groove binder dyes, are used to detect amplified mutated first target regions. Intercalator dyes are specific for double-stranded DNA are known in the art and include SYBR® GREEN and EVAGREEN™. Minor groove binding dyes include cyanine dyes 4-[(3-Methyl-6-(benzothiazol-2-yl)-2,3-dihydro-(benzo-1,3-thiazole)-2-methylidene)]-1-methyl-pyridinium iodide (BEBO) and BOXTO (4-[6-(benzoxazole-2-yl-(3-methyl-)-2,3-dihydro-(benzo-1, 3-thiazole)-2-methylidene)]-1-methyl-quinolinium chloride). Flow cytometry methods may then be used to measure fluorescence of mutated first target region amplicons from various digital PCR platforms (Warren et al., 2006, Proc. Natl. Acad. Sci. USA 103:17807-17812; Dressman et al., 2003, Proc. Natl. Acad. Sci. USA 100:8817-8822; Hindson et al., 2011, Anal. Chem. 83:8604-8610).

The number of amplified mutated first target regions (i.e., rare nucleic acid molecule mutations) per partition or droplet is calculated using Poisson statistics:

$$\lambda = -\ln(1-p)$$

where $\lambda$ is the average number of mutant genomes per partition and p is the fraction of positive partitions. From $\lambda$, the absolute concentration of mutation-bearing nucleic acid molecules is calculated using the volume of each partition and the total number of partitions analyzed (Hindson et al., 2011, Anal. Chem. 83:8604-8610, incorporated by reference in its entirety).

Quantification of mutation frequency using digital PCR also uses a control primer set. The first primer set is complementary to nucleic acid sequences that flank a first target region on a nucleic acid molecule and measures the concentration of nucleic acid molecules comprising a mutation. The control primer set, a control 5' primer and a control 3' primer, is complementary to nucleic acid sequences that flank a control target region in a separate region of a nucleic acid molecule and contains no restriction sites for the first (or other) restriction endonuclease. The control primer set measures the concentration of all nucleic acid molecules in a plurality of nucleic acid molecules. Because certain mutations (e.g., de novo deletions) are so rare, in certain embodiments, PCR reactions using different primer sets may be run using different dilutions of the digested plurality of nucleic acid molecules. Mutation frequency may be calculated by taking the ratio of normalized concentrations of mutation bearing nucleic acid molecules to the total nucleic acid molecules screened. In some embodiments, reactions that yielded less than 10 positive partitions (e.g., droplets) per well are scored conservatively as having no positives above background (Pinheiro et al., 2012, Anal. Chem. 1003-1011).

Methods for detecting rare nucleic acid mutations disclosed herein may also be used to detect a plurality of different mutations located in multiple target regions, as well as located in a single target region. For example, the methods described herein may further comprise amplifying a mutated second target region from the plurality of nucleic acid molecules that have been contacted with a first restriction endonuclease. A first restriction endonuclease is capable of cleaving a nucleic acid molecule comprising a first target region having a site specific for the first restriction endonuclease, and the nucleic acid molecule is not cleaved by the first restriction endonculease when the first target region comprises a mutation that alters the restriction site for the first restriction endonuclease. A first restriction endonuclease may also cleave a second target region having a site specific for the first restriction endonuclease, while a nucleic acid molecule is not cleaved at the second target region by the first restriction endonuclease if the second target region comprises a mutation that alters the site specific for the first restriction endonuclease. A mutated second target region is then amplified with a second 5' primer and second 3' primer, which are complementary to nucleic acid sequences flanking the second target region on a nucleic acid molecule, and only mutated target regions (i.e., first and second target region using their respective primer sets) are substantially amplified. Amplified amount of mutated second target region is then quantified, thereby detecting rare mutations in two different target regions with a single restriction endonuclease. In other embodiments, the methods disclosed herein further comprise amplifying a plurality of different target regions, wherein one or more different target regions comprise a mutation that alters a site specific for the first restriction endonuclease. The plurality of mutated target regions is then quantified, thereby detecting rare mutations in a plurality of different target regions using at least one restriction endonuclease. Mutations in a plurality of target regions on a nucleic acid molecule may be detected using a single restriction endonuclease with at least one restriction site (preferably two or more) within each of the plurality of target regions.

Alternatively, mutations in a plurality of target regions on a nucleic acid molecule may be detected using multiple restriction endonucleases. In certain embodiments, the contacting step (a) further comprises contacting a plurality of nucleic acid molecules with a second restriction endonuclease. The second restriction endonuclease is be capable of cleaving a nucleic acid molecule comprising a second target region having a site specific for the second restriction endonuclease, and a nucleic acid molecule is not cleaved by the second restriction endonuclease when the second target region comprises a mutation that alters the site specific for the second restriction endonuclease. The mutated second target region is then amplified with a second 5' primer and second 3' primer, wherein the primers are complementary to nucleic acid sequences flanking the second target region on a nucleic acid molecule, and wherein only mutated target regions are substantially amplified. The amplified amount of the mutated second target region is then quantified, thereby detecting rare mutations in two different target regions using two restriction endonucleases. In other embodiments for detecting mutations in a multiple of target regions, one or more different target regions may comprise a mutation that alters a site specific for the first restriction endonuclease, or one or more different target regions may comprise a mutation that alters a site specific for the second restriction endonuclease. In yet other embodiments for detecting a plurality of mutations in multiple target regions, multiple restriction endonucleases (e.g., two, three, four, or five) are used, and a restriction site specific for each restriction endonuclease is each located within a different target region. Multiple mutated target region amplicons from different target regions may be quantified and detected using methods known in the art, such as differentially labeled fluorescent primers or probes or incorporating unique bar codes/cyphers/identifier tags into the primers.

For methods of detecting rare nucleic acid molecule mutations in a plurality of different target regions using multiple restriction endonucleases, it is apparent to one of skill in the art that the plurality of nucleic acid molecules may undergo cleavage with multiple restriction endonucleases in a single reaction, or digests may occur individually or be divided into smaller sets of multiple digests that are compatible with each other (e.g., compatible buffers and reaction conditions, compatible locations of restriction sites, compatible locations of target regions for downstream quantification). Amplification of the plurality of mutated target regions may also occur in a single reaction, in individual reactions with a single primer set complementary to nucleic acid sequences flanking a single target region, or in pooled reactions with multiple primer sets complementary to nucleic acid sequences flanking multiple target regions. It is apparent to one of skill in the art how to design pooled amplification experiments for optimal amplification of mutated target regions and subsequent quantification.

In certain embodiments, the amplified target regions comprising a mutation are then be further characterized. Following thermal cycling, the amplified target regions may undergo further processing prior to characterization, including purification processes to remove oil carrier (for oil-in-water droplets), excess primers, probes, or digested template DNA. Sizes of the amplicons may be analyzed via gel electrophoresis methods known in the art, including agarose gel electrophoresis, polyacrylamide gel electrophoresis, or capillary gel electrophoresis. Amplified target regions may also be cloned and then sequenced using techniques known in the art. In certain embodiments, where digital PCR uses a PCR mix containing dUTP in place of dTTP, the resulting amplicons are not suitable for standard cloning techniques because of *E. coli*'s endogenous uracil DNA glycosylases. Thus, a second round of PCR may be performed to generate thymidine bearing amplicons. Additionally, non-specific products may amplify in the partitions. Non-specific artifacts do not bind the TAQMAN probe and therefore do not affect quantification of the amplified target regions. However, non-specific products may interfere with cloning and sequencing of true mutation-containing amplicons. Therefore, in other embodiments, target specific amplicons are selected for cloning using a second round of PCR with a set of nested primers that anneal to a target region's TAQMAN probe site. Standard cloning and sequencing techniques may then be performed on following a second round of PCR. Sequencing amplified target regions allows precise definition of size, location, breakpoints, sequence, type of mutation, frequency of each mutation, or spectrum of mutations.

In certain embodiments, the methods disclosed herein may be used to monitor accumulation of rare nucleic acid molecule mutations over time. For example, frequency of a nucleic acid mutation, such as a deletion, within a first target region can be monitored over time by performing the methods disclosed herein on a plurality of nucleic acid molecules derived from a sample from a subject to detect mutations at an initial timepoint. A sample that is similar in type to the initial sample (e.g., both are blood samples, both are tissue biopsy samples) is obtained from the subject at a later timepoint (e.g., hours, days, weeks, months, or years later) and then the selected method used for detecting nucleic acid mutations in the initial sample is performed on the plurality of nucleic acid molecules derived from the later sample. Multiple time points may be performed, and the mutations may be further characterized for changes in size, location, breakpoints, sequence, types of mutation, frequency, or spectrum of mutations over time. Similarly, accumulation of mutations in multiple target regions may be monitored over time.

The methods of the present disclosure may be used to detect nucleic acid molecules, including genomic and mitochondrial DNA, comprising a mutation associated with a variety of diseases. Mitochondrial and genomic mutations are associated with muscular disorders, neuropsychiatric disorders, cancer, and neurodegenerative diseases (Chinnery, P. F. in Gene Reviews eds. R A. Pagon, T. D. Bird, C. R. Dolan & K. Stephens, 1993); Kato et al., 2011, Neurosci. Res. 69:331-336; Horton et al., 1995, Neurology 45:1879-1883; Lee et al., 2010, Ageing Res. Rev. 9:S47-58; Cancer Genetics and Cytogenetics, 2001, 128:18; Fearon & Vogelstein, 1990, Cell 61:759-767; Yokota, 2000, Carcinogenesis 21:497-503). Mitochondrial DNA deletions are also associated with aging (Vermulst et al., 2008, Nat. Genet. 40:392-394; Tanhauser and Laipis, 1995, J. Biol. Chem. 270:24769-24775). Using the methods disclosed herein for detecting nucleic acid molecules comprising a mutation associated with a disease may be useful for determining disease diagnosis, disease staging or progression, prediction of response to therapy, or spectrum of mutations in a sample.

Huntington's Disease is a neurodegenerative genetic disorder caused by polyglutamine expansion of the Huntington protein (Htt) that affects muscle coordination and leads to cognitive decline and psychiatric problems. A potential mechanism of pathogenesis of Huntington's Disease is via mitochondria dysfunction (Kim et al., 2010, Hum. Mol. Genet. 19:3919-3935). Huntington's disease is associated with elevated levels of common mitochondrial 4977 deletion in the cortex (Horton et al., 1995, Neurology 45:1879-1883). Other mitochondrial DNA deletions have also been observed in Huntington's disease patients (Banoei et al., 2007, Cell Mol. Neurobiol. 27:867-75).

Kearns-Sayre syndrome (KSS) causes progressive external ophthalmoplegia, abnormalities of the electrical signals that control the heartbeat (cardiac conduction defects), problems with coordination and balance that cause unsteadiness while walking (ataxia), or abnormally high levels of protein in the fluid that surrounds and protects the brain and spinal cord (the cerebrospinal fluid or CSF). Pearson syndrome is a usually fatal disorder of infancy characterized by sideroblastic anemia and exocrine pancreas dysfunction. Chronic progressive external ophthalmoplegia (CPEO) is similar to KSS, but with later onset. These three diseases, which all arise sporadically, are commonly caused by a specific mtDNA deletion of 4977 by between two direct repeats in the mtDNA sequence at nucleotide positions 13447-13459 and 8470-8482 (Porteous et al., 1998, Eur. J. Biochem. 257:192-201; Wong, 2001, Genet. Med. 3:399-404). However, the length and location of mtDNA deletions in these patients are variable (Yamashita et al., 2008, J. Hum. Genet. 53:598-606).

Deletions in tumor suppressor genes, including PTEN, RB1, p16, CHEK2, or p53, are common causes of cancer. Numerous cancers have mutations in the p53 tumor suppressor gene (Kohler et al., 1993, JNCI J. Natl. Cancer Inst. 85:1513-1519; Nichols et al., 2001, Cancer Epidemiol. Biomarkers Prev. 10:83). A spectrum of deletions and insertions have been observed in the RB1 gene in retinoblastoma patients (Albrecht et al., 2005, Human Mutation 26:437-445). A 5,395 bp deletion in CHEK 2 predisposes to breast cancer (Cybulski et al., 2007, Breast Cancer Research and Treatment 102:119-122). PTEN genomic deletions are associated with poor clinical outcome in prostate cancer patients (Yoshimoto et al., 2007, Br. J. Cancer 97:678-85). P16 deletions are also associated with unfavorable clinical outcome in leukemia patients (Kees et al., 1997, Blood 89:4161-4166). The spectrum of mitochondrial DNA deletions may also be useful as a biomarker of ultraviolet radiation exposure in the skin (Ray et al., 2000, J. Invest. Derm. 115:672-679).

Facioscapulohumeral muscular dystrophy (FSHD) is a usually autosomal dominant form of muscular dystrophy that initially affects the skeletal muscles of the face, scapula, and upper arms. It is the third most common inherited muscular dystrophy. FSHD is associated with deletion of integral copies of a tandemly repeated 3.2 kb unit (D4Z4 repeat) at the subtelomeric region 4q35 on chromosome 4, from 11-100 copies to 1-10 copies (Dixit et al., 2007, Proc. Natl. Acad. Sci. USA 104:18157-18162).

Mitochondrial dysfunction/deletions have also been suggested to be involved in the pathogenesis of psychiatric disorders, such as depression, schizophrenia, and dementia (Kato et al., 2011, Neurosci. Res. 69:331-336), cancer, and aging (Lee et al., 2010, Ageing Res. Rev. 9:S47-58).

Barrett's esophagus is a premalignant intermediate to esophageal adenocarcinoma, which develops in the context of chronic inflammation and exposure to bile and acid. Deletion and loss of heterozygosity at fragile sites are common and early events in Barrett's esophagus and may serve as biomarkers of cancer risk in Barrett's esophagus patients (Dagmar et al., 1997, Nature 15:1653-1659; Lai et al., 2010, Mol. Cancer. Res. 8:1084-1094).

The BCR-ABL fusion oncogene tyrosine kinase, the result of a reciprocal translocation between chromosome 9 and 22, causes chronic myelogenous leukemia. Depending on the precise location of the fusion, the molecular weight of BCR-ABL can range from 185 to 210 kDa. Three clinically important variants are p190, p210, and p230 isoforms. p190 is generally associated with acute lymphoblastic leukemia, while p210 is generally associated with chronic myeloid leukemia and also ALL. P230 is usually associated with chronic neutrophilic leukemia. Treatment of CML patients with imatinib frequently encounters resistance due to mutations in the BCR-ABL kinase domain.

In certain embodiments, the methods for detecting nucleic acid molecules comprising a rare mutation of the present disclosure may be used for pre-natal diagnosis. Cell-free fetal nucleic acids can be obtained from maternal circulation (Wright and Burton, 2009, Human Reprod. Update 15:139-151). Aneuploidy, translocations, or specific deletions associated with genetic disorders may be detected by using restriction endonucleases to cleave the overwhelming background of maternal cell-free DNA and then amplifying and quantitating target regions of interest using the methods as described herein.

Methods for Determining Amplicon Size

Also disclosed herein are methods for determining quantity and size of an amplicon using droplet digital PCR. The present disclosure provides an unexpected quantitative relationship between droplet fluorescence and amplicon size with high resolution that can be used determine the size of multiple targets of varying length. Using these methods, the quantity and size of fragments in a DNA library, such as a DNA library being prepared for next generation sequencing, may be rapidly determined.

By way of background, next-generation sequencing instruments have been developed, which are in general based on a massively parallel clonal amplification method to directly generate clusters of DNA templates at high densities on a substrate (e.g., glass slide, polymer bead, or flow cell surface). NGS technology is rapidly revolutionizing the fields of genomics molecular diagnostics, and personalized medicine through the increasingly efficient and economical generation of unprecedented volumes of data (Didelot et al., 2012, Nature Rev. Genetics, 13:601-612; Biesecker et al., 2012, Nature Rev. Genetics 13:818-824; Martin et al., 2011, Nature Rev. Genetics 12:671-682; Voelkerding et al., 2009, Clin. Chem. 55:641-658; Su et al., 2011, Expert Rev. Mol. Diag. 11:333-343; Meyerson et al., 2010, Nature Rev. Genetics 11:685-696; Zhang et al., 2011, Journal of Genetics and Genomics=Yi chuan xue bao 38:95-109). Some commonly used NGS platforms are the 454 GS Junior (Roche), Ion Torrent (Life Technologies), and MiSeq (Illuminia), which are "benchtop" sequencers designed for laboratory use. These platforms are capable of a wide range of sequencing applications due to their versatility in sample type, experiment scale, instrument protocol, and multiplexing options (Liu et al., 2012, J. Biomedicine & Biotechnology, 2012, 251364; Loman et al., 2012, Nature Biotechnol. 30:434-439; Glenn, 2011, Mol. Ecol. Resources 11:759-769; Quail et al., 2012, BMC Genomics 13:341). The 454 and Ion Torrent platforms use emulsion PCR to generate millions of DNA molecules with the same sequence from a single sample molecule attached to a polymer bead. The Illumina platforms use bridge PCR to amplify single surface-bound molecules to generate a cluster of molecules with the same sequence. Templates are then sequenced by a stepwise incorporation of nucleotides (e.g., Illumina Genome Analyzer, Roche Applied Science 454 Genome Sequencer) or short oligonucleotides (e.g., Applied Biosystems SOLiD). Both the bridge PCR and emulsion PCR methods of parallel amplification require the ligation of adapter sequences to the ends of sample DNA molecules to create sequencing libraries that can bind to surface or bead-bound probes complementary to the adapters. While the actual sequencing process in next generation sequencing has been streamlined and automated, the upstream sample preparation remains a challenge. There is a need for a method to convert source material into a standard DNA library suitable for loading onto the sequencing instrument compatible with high throughput workflows.

The preparation of DNA for next generation sequencing usually comprises of four main operations: 1) fragmentation, usually performed by mechanical shearing of the DNA such as high pressure or ultrasound treatment; 2) repair, modification and ligation of adapters, are all enzymatic steps preparing the sheared DNA by addition of universal sequences at the fragment ends thereby enabling amplification and hybridization of the sequencing primers; 3) size selection of DNA molecules with a certain length optimal for the current application or instrument; and 4) enrichment for DNA molecules with successfully ligated adapters.

For each of the current next generation sequencing platforms, the input is a double stranded DNA library consisting of short fragments flanked by adapters of known (and platform-specific) sequence. Optimal fragment length varies among the next generation sequencing platforms (Linnarsson, 2010, Exp. Cell Res. 316:1339-1343). Tight size selection reduces wasted "non-aligned" reads and increases average read length by excluding shorter fragments. For example, the SOLiD system (Applied Biosystems) works best with shorter fragments (150-200 bp). In contrast, the Genome Analyzer (Illumina) accepts a greater range of fragments (100-600), but the yield drops as fragments get longer because longer fragments result in larger surface clusters that must be spaced less densely. Size selection is generally performed by agarose gel or capillary electrophoresis. Standard protocols for gel extraction include a heating step that may denature some AT-rich sequences and render them un-ligatable. UV exposure of a standard ethidium bromide gel also reduces cloning efficiency. While other gel systems are available which avoid heating, ethidium bromide, and UV exposure (e.g., SizeSelect E-gels from Invitrogen), gel electrophoresis is still a labor intensive bottleneck in sample preparation. Stand-alone commercial systems have recently emerged targeting the problem of manual gel separation, e.g., LabChip XT (Caliper) and Pippin Prep (Sage Science). However, these systems require extra instrumentation not easily integrated in a fully automated workflow.

Furthermore, in order to maximize the amount of sequencing information from next generation sequencing platforms, and thereby reduce the cost per base pair sequenced, the amount of prepared DNA library for a sequencing run is monitored. The optimal input sample concentration also varies among the next generation sequencing platforms (Linnarsson, 2010, Exp. Cell Res. 316:1339-1343). For example, for the Illumina Genome Analyzer, the DNA library is immobilized by hybridization on a chip and amplified in situ in a process termed cluster generation. If the amount of DNA loaded is too high, the DNA clusters generated will overlap and thereby affect the quality of sequencing data. Loading a suboptimal amount of DNA results in a low cluster density, and reduces sequencing efficiency. On any NGS platform, performing a sequencing run with either too many or too few library molecules results in compromised data yields or completely failed sequencing runs that waste sample, user time, instrument time, and expensive reagents. DNA quantification methods, such as UV spectrophotometry, Quant-iT PicoGreen assay, Agilent BioAnalyzer, or gel electrophoresis, are widely used. However, with these methods, DNA fragments lacking the necessary adapters for cluster generation will also be measured (Linnarsson, 2010, Exp. Cell Res. 316:1339-1343; Meyer et al., 2008, Nucleic Acids Res. 36:e5; Buehler et al., 2010, Methods 50:S15-18), which can result in a lower cluster density than expected when a standard concentration of DNA is loaded onto the cluster generation station. These methods also have low sensitivity, consuming nanograms of precious samples, and are not suitable for high-throughput workflows. These methods are also only capable of measuring mass per volume, which must be converted to copy number using an estimated average size of library molecules which can introduce further error (White et al., 2009, BMC Genomics 10:116). Quantitative PCR is the recommended method for library quantification at present. However, there are considerable drawback to the method including amplification biases due to template size and GC-content and the need for a standard curve to estimate the absolute quantity of DNA (Valasek et al. 2005, Advances in Physiology Education 20:151-159). Creating a standard curve for each sample to be analyzed is a difficult and uncertain process that leads to inaccuracies in measurements of absolute target quantity (White et al., 2009, BMC Genomics 10:116; Yun et al., 2006, Nucleic Acids Res. 34:e85). Because of these potential inaccuracies, some NGS platform manufacturers recommend performing titration runs on their instrument to determine the proper loading amount, which is an expensive and time-consuming step. Thus, accurate quantification and size determination of library DNA is essential for achieving maximal data yield and maximizing a laboratory's efficiency and sequencing throughput.

Initial analysis of fluorescence amplitudes of three control plasmids following droplet digital PCR revealed that the fluorescent intensity of a positive droplet is inversely proportional to the amplicon size within the droplet (i.e., the smaller the amplicon, the higher the fluorescent intensity). The mean fluorescence amplitude (±s.d.) of positive droplets from the three control plasmids experiment were plotted against their expected amplicon size. The plot showed that the droplet digital PCR fluorescence data fit an exponential expression pattern, demonstrating the relationship between amplitude and amplicon size. The present disclosure provides a droplet digital PCR based assay that circumvents the limitations of other methods for quality control of NGS libraries, increases the accuracy of quantification, consumes less sample, and can combine quantification and size determination in a single method. In a ddPCR experiment, a mixture of target DNA template, PCR reagents, and target-specific fluorescent probe is partitioned into ~20,000 discrete one-nanoliter oil droplets per reaction well. The fluorescence assay may use a Taqman probe that fluoresces only when its fluorophore is separated from its quencher by the 5'-3' exonuclease activity of Taq polymerase as it moves along the template DNA strand. Consequently, the fluorescence amplitude of each discrete droplet is proportional to the number of amplicons that have been generated from the template DNA at the endpoint of the reaction. Positive droplets, which contain template, will fluoresce above the background fluorescence of negative droplets, which lack template and thus produce no amplicons. The total number of target molecules in a sample can be calculated from the fraction of total droplets that are positive using the Poisson statistical equation:

$$\lambda = -\ln(1-p)$$

where p is the fraction of positive droplets and $\lambda$ is the average number of target molecules per droplet (Hindson et al., 2011, Analytical Chem. 83:8604-8610). Because individual amplifiable molecules are partitioned into their own droplets, reagents are not shared between templates and the ddPCR system is not subject to the same length and GC-content amplification biases as bulk reactions in real-time PCR (Hindson et al., 2011, Analytical Chem. 83:8604-8610; Hori et al., 2007, Biochem. Biophys. Res. Comm. 352:323-328). The ddPCR system may be used to simultaneously provide absolute quantification of target nucleic acid molecule and measure the length of unknown amplifiable nucleic acid template molecules by applying a linear correlation between the fluorescence amplitude of droplets and the size of amplicons within them.

In certain embodiments, the present disclosure provides methods for determining the size of a nucleic acid molecule comprising: amplifying the nucleic acid molecule using droplet digital PCR to produce a target amplicon; measuring the fluorescence value of a positive droplet containing the target amplicon; and comparing the fluorescence value of the positive droplet containing the target amplicon to the fluorescence values of at least two control amplicons of known size, thereby determining the size of the nucleic acid molecule.

Droplet digital PCR may be performed using any platform that performs a digital PCR assay that measures absolute quantities by counting nucleic acid molecules encapsulated in discrete, volumetrically defined, water-in-oil droplet partitions that support PCR amplification. The strategy for droplet digital PCR may be summarized as follows: a sample is diluted and partitioned into thousands to millions of separate reaction chambers (water-in-oil droplets) so that each contains one or no copies of the nucleic acid molecule of interest. The number of "positive" droplets detected, which contain the target amplicon (i.e., nucleic acid molecule of interest), versus the number of "negative" droplets, which do not contain the target amplicon (i.e., nucleic acid molecule of interest), may be used to determine the number of copies of the nucleic acid molecule of interest that were in the original sample. Examples of droplet digital PCR systems include the QX100™ Droplet Digital PCR System by Bio-Rad, which partitions samples containing nucleic acid template into 20,000 nanoliter-sized droplets; and the RainDrop™ digital PCR system by RainDance, which partitions samples containing nucleic acid template into 1,000, 000 to 10,000,000 picoliter-sized droplets.

Figure 2A:
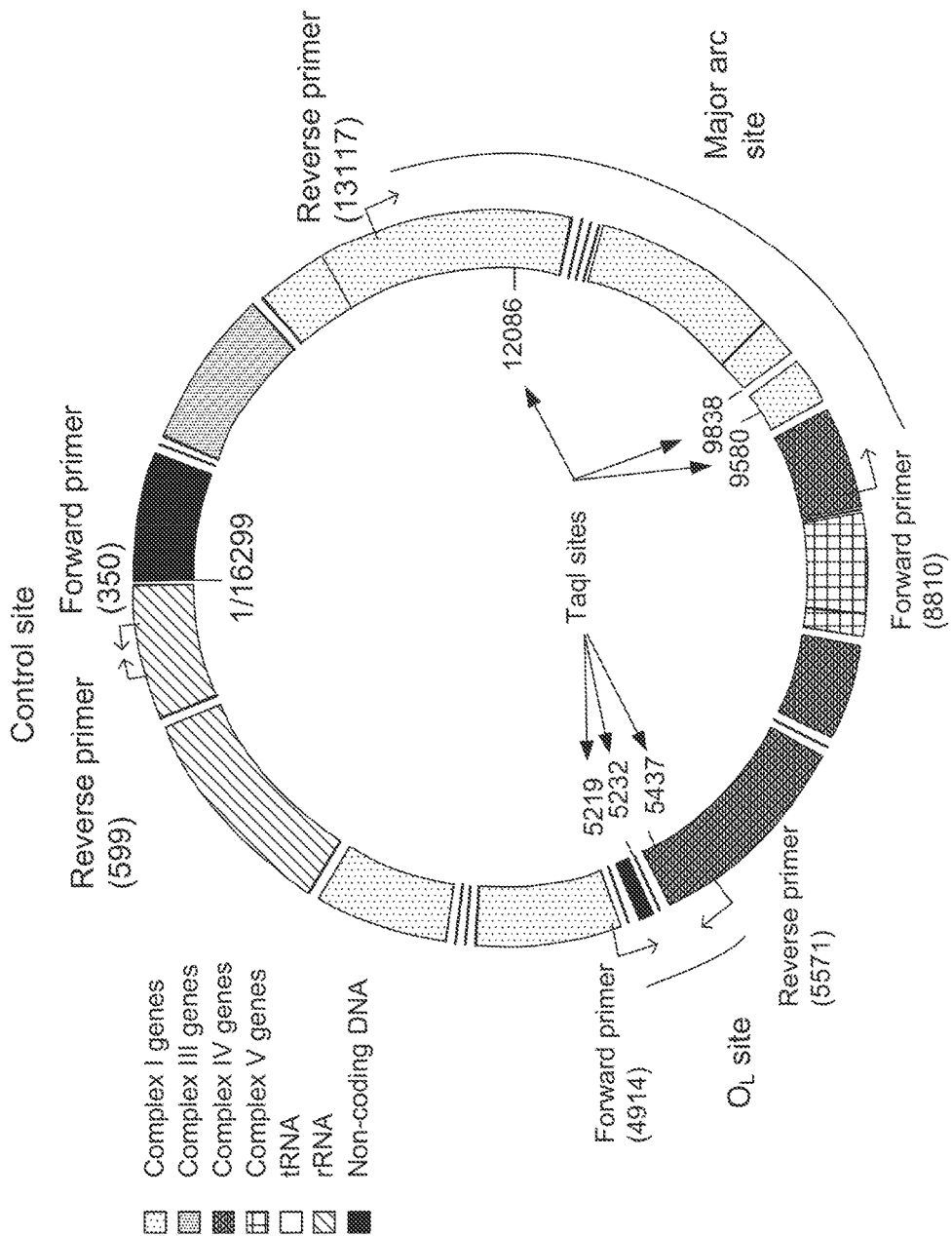
FIG. 2. Quantification of absolute mtDNA deletion frequency (±s.e.m.) in pol γ exonuclease deficient mouse tissue and cells. (A) and (B) 3D analysis of mtDNA isolated from Polga$^{+/+}$ and Polga$^{-/-}$ knock-in mice. (A) The first primer set flanks three TaqI restriction sites in the major arc target region of the mouse mitochondrial genome, while the second primer set flanks three TaqI restriction sites spanning $O_L$ target region. The control target region is located in the 12 S rRNA gene. (B) 3D analysis at each target region yields an absolute deletion frequency for Polga$^{+/+}$ and Polga$^{-/-}$ mice. (c) and (d) 3D analysis of mtDNA isolated from HeLa cells expressing the recombinant D274A pol γ mutant polymerase under control of a tetracycline inducible promoter. (C) The primers flank four TaqI restriction sites in the minor arc target region of the human mitochondrial genome. The control target region is located in the ATP8 gene. (D) Cells are treated for 21 days with or without doxycycline. 3D analysis allows quantification of absolute deletion frequencies under both conditions.
Figure 2B:
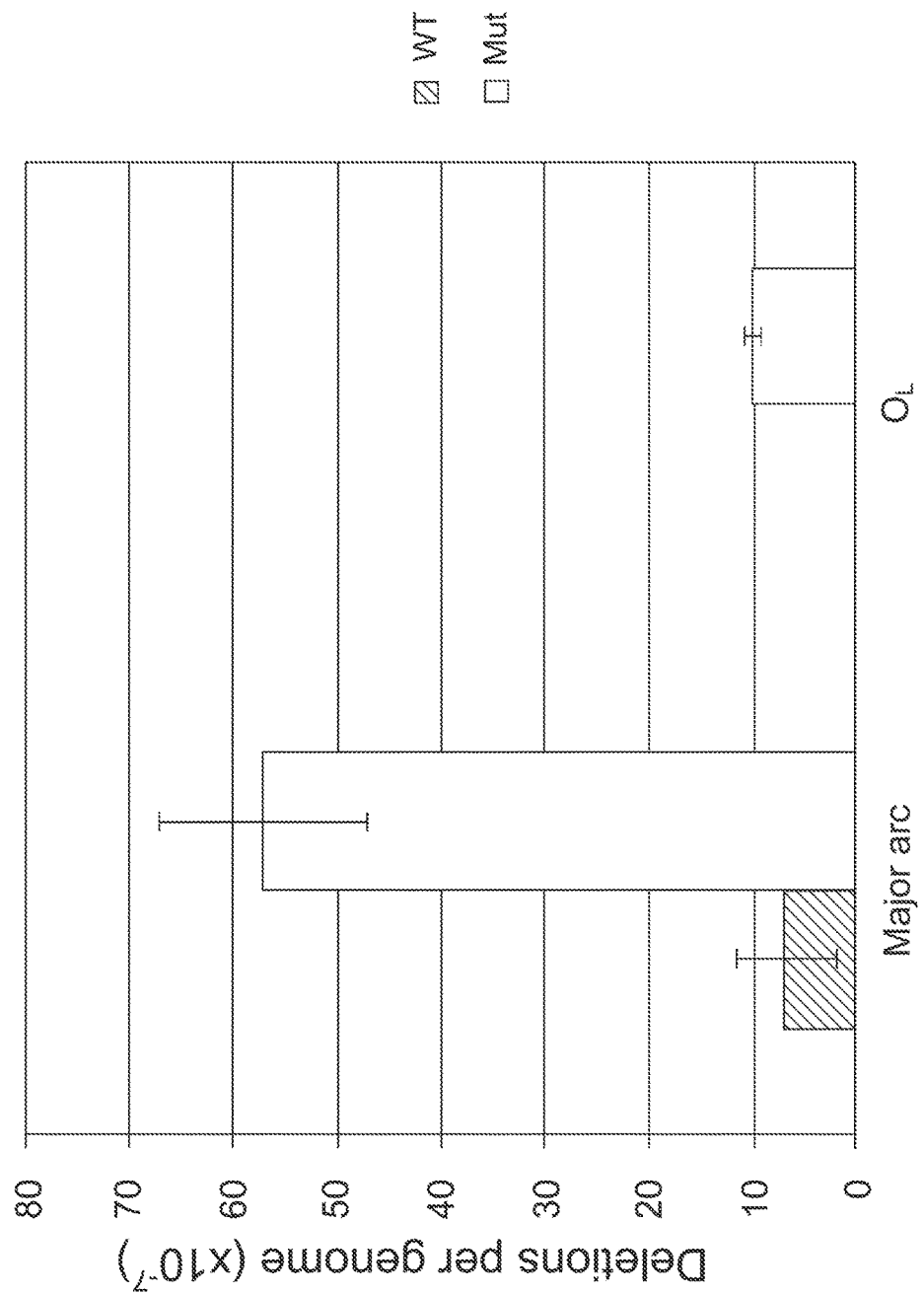
Figure 2C:
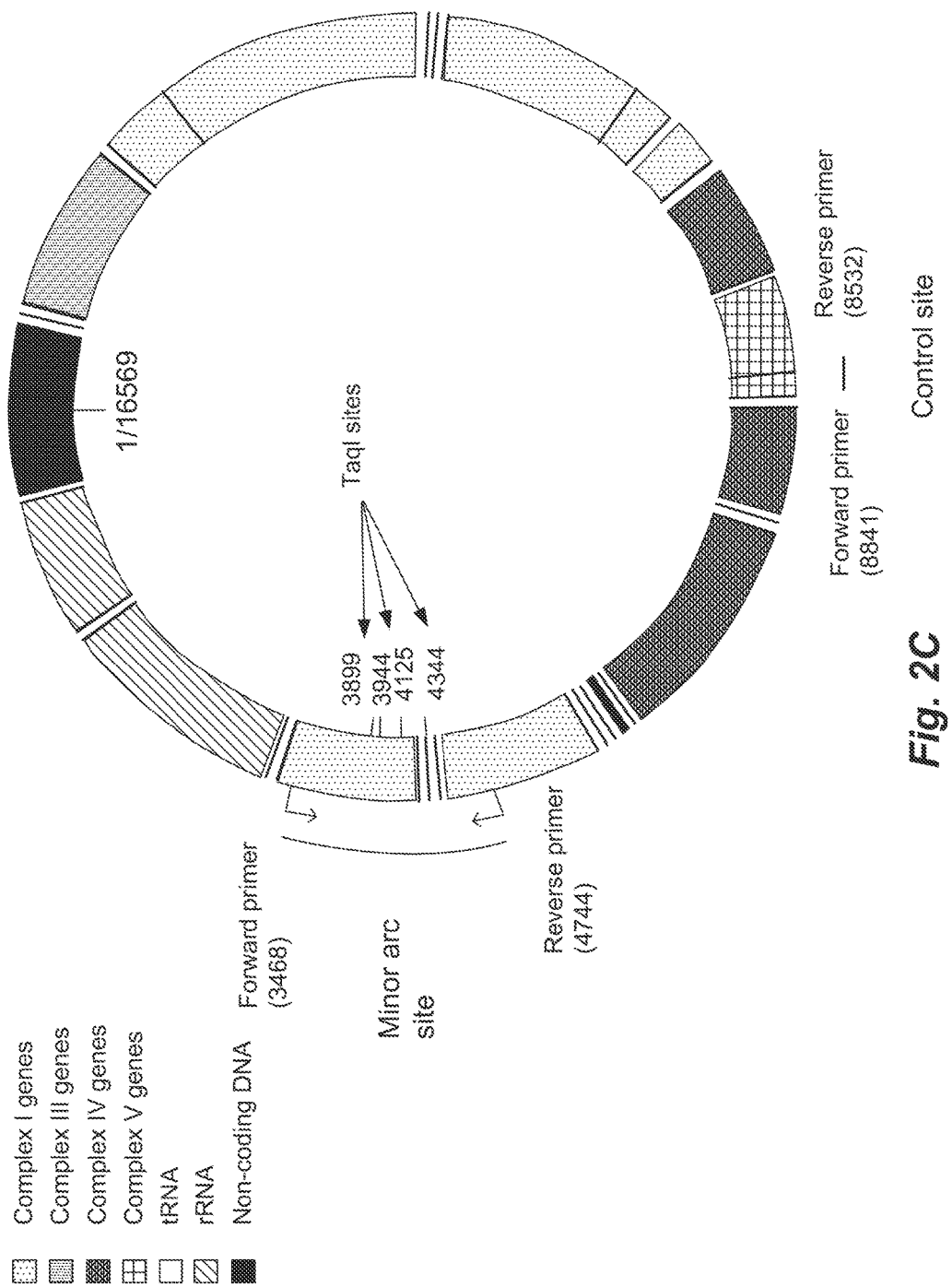

Primers that are used for amplification of a nucleic acid molecule to produce a target amplicon may anneal to sequences that are found in the nucleic acid molecule or anneal to sequences that are not originally found in the nucleic acid molecule. The entire nucleic acid molecule may be the template for the target amplicon or the nucleic acid molecule may contain a template for the target amplicon. By way of example, FIGS. 2A and 2C show primers that anneal to the major arc site, $O_L$ site, and minor arc site of mtDNA that were used to amplify and produce target amplicons of the major arc site, $O_L$ site, and minor arc site, respectively. In another example, the nucleic acid molecule may be flanked by sequences not originally found in the nucleic acid molecule, for example by vector sequence, adapter sequences, indices, bar codes, restriction enzyme sites, primer annealing sites or tags that are commonly used in DNA library construction or other molecular biology assays. Primers may anneal to the sequences flanking the nucleic acid molecule to produce a target amplicon comprising the nucleic acid molecule and the flanking sequence amplified by the primers. Methods for adding flanking sequence to a nucleic acid molecule, for example, by ligation or PCR, are known in the art.

In certain embodiments, the nucleic acid molecule comprises a molecule having a formula of, from 5' to 3', $X^a$-Y-$X^b$, wherein: $X^a$ comprises a first primer annealing site; Y comprises the target nucleic acid molecule; and $X^b$ comprises a second primer annealing site. In certain embodiments, first and second primer annealing sites may be part of the original nucleic acid molecule. By way of example, the first and second primer annealing sites may be sequence at the 5' and 3' ends of the original nucleic acid molecule (see, e.g., FIGS. 2A and 2C which show primers that anneal to the 5' and 3' ends of the major arc site, $O_L$ site, and minor arc site of mtDNA). In other embodiments, first and second primer annealing sites may be contained within sequence that has been joined to the nucleic acid molecule using molecular biology techniques. In some embodiments, first and second primer annealing sites are contained within a first adapter sequence and a second adapter sequence, respectively, that flank the nucleic acid molecule. In certain embodiments, each adapter sequence comprises a length ranging from about 10 nucleotides to about 200 nucleotides. Adapter sequences for use in NGS library construction are known in the art. First and second primer annealing sites may also be contained within bar codes or vector sequences that flank the nucleic acid molecule. In certain embodiments, the nucleic acid molecule (Y) further comprises a first index sequence disposed between $X^a$ and Y, and a second index sequence disposed between Y and $X^b$. An index sequence may comprise a length ranging from about 4 nucleotides to about 25 nucleotides. An index sequences (unique identifier tag) may be used to label different samples (e.g., different libraries, different ligation reactions) to allow for multiplexing.

A first primer (5') and a second primer (3') that anneal to the first and second primer annealing sites, respectively, may be used to amplify the target amplicon and control amplicons of known size. This may be accomplished when the target amplicon and control amplicons are flanked by common sequences (e.g., vector sequences, adapter sequences). In certain embodiments, a first fluorogenic probe binds to the target amplicon and the control amplicons. Providing that the target amplicon and control amplicons are flanked by common sequences (e.g., vector sequences, adapter sequences), the fluorogenic probe may bind to a region of common sequence amplified by the primers. In certain embodiments, a first primer and a second primer are used to amplify the target amplicon and control amplicons and a first fluorogenic probe is used to detect the target amplicons and control amplicons. By way of example, for nucleic acid libraries and control amplicons created with adapter sequences flanking the nucleic acid insert, the first and second primers anneal to primer annealing sites within the adapter sequences, and the fluorogenic probe may bind to a portion of the adapter sequence amplified by the primers (see, e.g., FIG. 10). Primers specific for the adapter sequences used in next generation sequence platforms also provide confirmation that the target amplicons contain the necessary adapter sequence for cluster generation. In other embodiments, a first fluorogenic probe binds the nucleic acid molecule (i.e., Y in $X^a$-Y-$X^b$). In other embodiments, multiple fluorogenic probes (e.g., at least 2, 3, 4, 5, 6, 7, 8, 9, 10, or more fluorogenic probes), each with different fluorophores, may be used in a ddPCR experiment to detect different target amplicons. By way of example, multiple fluorogenic probes may be used to detect target amplicons representing different ligation products, different deletion products, different copy number variants, etc.

In the various embodiments provided herein, the fluorescence value or amplitude of an individual positive droplet containing the target amplicon, or the mean or median fluorescence value of a test sample comprising a plurality of positive droplets containing the target amplicon may be compared to the fluorescence values of at least two control amplicons of known size (also referred to as size standards), thereby determining the size of the nucleic acid molecule. In the various embodiments provided herein, the fluorescence values of the at least two control amplicons of known size may be a fluorescence value of an individual positive droplet containing a control amplicon, or the mean or median fluorescence values of each control sample. Using fluorescence values of individual droplets allows for more detailed analysis of amplicon size distribution in a sample. In certain embodiments, the at least two control amplicons of known size are produced in the same experiment as the target amplicon. In other embodiments, the at least two control amplicons of known size are not produced in the same experiment as the target amplicon. The fluorescence value of any unknown target amplicon from different droplet digital PCR experiments may be compared to the fluorescence values of at least two control amplicons of known size, providing that the control amplicons and target amplicon are amplified under the same ddPCR conditions and the control and target amplicons share primer and probe binding sites. In certain embodiments, the target amplicon and control amplicons of known size are amplified in separate but parallel droplet digital PCR runs. In other embodiments, the target amplicon and control amplicons of known size are amplified in separate, non-parallel runs.

At least two, three, four, five, six, seven, eight, nine, ten, eleven, twelve, thirteen, fourteen, fifteen, sixteen, seventeen, eighteen, nineteen, twenty, or more control amplicons of known size may be used for comparison to the test amplicon. The at least two amplicons of known size have different lengths.

In certain embodiments, wherein a nucleic acid molecule template is inserted into a vector, the nucleic acid molecule template for generating a target or control amplicon may be lacking (i.e., size of nucleic acid molecule is 0). These empty vectors lacking insert may still generate short amplicons if the primers and probes anneal to sites within the vector, rather than the insert.

In certain embodiments, the at least two control amplicons of known size range in length from about 0 to about 10,000 nucleotides; from about 0 to about 9,000 nucleotides, from about 0 to about 8,000 nucleotides, from about 0 to about 7,000 nucleotides, from about 0 to about 6,000 nucleotides, from about 0 to about 5,000 nucleotides, from about 0 to about 4,000 nucleotides, from about 0 to about 3,000 nucleotides, from about 0 to about 2,000 nucleotides, from about 0 to about 1,000 nucleotides, or from about 0 to about 500 nucleotides. In certain embodiments, the at least two control amplicons of known size range in length from about 25 to about 10,000 nucleotides; from about 25 to about 9,000 nucleotides, from about 25 to about 8,000 nucleotides, from about 25 to about 7,000 nucleotides, from about 25 to about 6,000 nucleotides, from about 25 to about 5,000 nucleotides, from about 25 to about 4,000 nucleotides, from about 25 to about 3,000 nucleotides, from about 25 to about 2,000 nucleotides, from about 25 to about 1,000 nucleotides, or from about 25 to about 500 nucleotides.

In certain embodiments, the target amplicon is a length ranging from about 150 nucleotides to about 500 nucleotides, from 150 to about 1,000 nucleotides, from about 150 to about 2,000 nucleotides, from about 150 to about 3,000 nucleotides, from about 150 to about 4,000 nucleotides, from about 150 to about 5,000 nucleotides, from about 150 to about 6,000 nucleotides, from about 150 to about 7,000 nucleotides, from about 150 to about 8,000 nucleotides, from about 150 to about 8,000 nucleotides, from about 150 to about 9,000 nucleotides, from about 150 to about 10,000 nucleotides.

In other embodiments, the target amplicon is a length ranging from about 0 to about 10,000 nucleotides; from about 0 to about 9,000 nucleotides, from about 0 to about 8,000 nucleotides, from about 0 to about 7,000 nucleotides, from about 0 to about 6,000 nucleotides, from about 0 to about 5,000 nucleotides, from about 0 to about 4,000 nucleotides, from about 0 to about 3,000 nucleotides, from about 0 to about 2,000 nucleotides, from about 0 to about 1,000 nucleotides, or from about 0 to about 500 nucleotides. In other embodiments, the target amplicon is a length ranging from about 50 to about 10,000 nucleotides; from about 50 to about 9,000 nucleotides, from about 50 to about 8,000 nucleotides, from about 50 to about 7,000 nucleotides, from about 50 to about 6,000 nucleotides, from about 50 to about 5,000 nucleotides, from about 50 to about 4,000 nucleotides, from about 50 to about 3,000 nucleotides, from about 50 to about 2,000 nucleotides, from about 50 to about 1,000 nucleotides, or from about 50 to about 500 nucleotides.

In certain embodiments, a linear plot of the fluorescence values vs. control amplicon size is generated. The fluorescence value of the positive droplet containing the target amplicon can be compared to an equation of a line fitting the fluorescence values of the at least two control amplicons of known size. The equation of a line fitting the fluorescence values of the control amplicons and amplicon size (y=mx+b) can be used to calculate the size of a target amplicon. An inverse, linear correlation between amplicon size and fluorescence amplitude is observed. The slope (m) of this linear equation provides a measure of the difference in fluorescence amplitude that is expected with a given difference in amplicon size. Maximizing the magnitude of the slope maximizes the resolution of the control amplicons. The size of the nucleic acid molecule may be easily determined based on target amplicon size, taking into account any adapter sequences, vector sequences, index sequences, or the like which may be present in the target amplicon. It is apparent to one of skill in the art that an appropriate number and size range of control amplicons may be selected based upon the estimated size and diversity of the target amplicon(s).

Droplet digital PCR assay conditions may also be optimized to reliably discriminate between positive and negative droplets. For example, PCR elongation time may be varied. Increasing elongation time increases the fluorescence amplitude of all droplets containing amplifiable template and enables data collection for longer templates. However, the slope of the linear relationship between amplicon size and fluorescence amplitude decreases with increased elongation time, which decreases the ability to resolve small differences in amplicon size. Decreasing elongation time increases the resolution of size differences, but also prevents longer target nucleic acid molecules from amplifying to the point where they fluoresce above background level. In droplet digital PCR, the fluorescent amplitude reflects the reaction endpoint, which will vary depending on the size of the template and the availability of the reagents. In certain embodiments, relative differences in the fluorescent amplitude of amplicons of different sizes may be amplified or minimized depending on the primer concentration. In some embodiments, relative differences in the fluorescent amplitude of amplicons of different sizes are amplified by increasing the primer concentration used in droplet digital PCR. It is apparent to one of skill in the art how to vary assay conditions (e.g., elongation time, primer concentration) to optimize size resolution for a particular sample.

In certain embodiments, the methods described herein further comprise detecting a deletion or copy number variation in the nucleic acid molecule. In certain embodiments, the sizes of a plurality of nucleic acid molecules are determined. The plurality of nucleic acid molecules may be a library of nucleic acid molecules for next generation sequencing or a ligation reaction. In certain embodiments, the plurality of nucleic acid molecules have a formula of, from 5' to 3', $X^a$-Y-$X^b$, wherein: $X^a$ comprises a first adapter sequence primer annealing site; Y comprises the nucleic acid molecule; and $X^b$ comprises a second adapter sequence primer annealing site;
wherein the first and second primer annealing sites are first and second adapter sequences, respectively. The methods provided in the present disclosure may also be used to determine size distribution of a plurality of nucleic acid molecules. Size selection of target amplicons is useful for next generation sequencing sample preparation or identifying ligation reactions with appropriately sized product. In some embodiments, the plurality of nucleic acid molecules is contained in a self-replicating vector.

In certain embodiments, the sizes of nucleic acid molecules within multiple libraries are determined using the methods described herein.

In certain embodiments wherein up to 10,000 nucleic acid molecules are loaded per well or tube in a droplet digital PCR reaction. In other embodiments, up to 1000, 2000, 3000, 4000, 5000, 6000, 7000, 8000, 9000, 10000, 11000, 12000, 13000, 14000, 15000, 16000, 17000, 18000, 19000, 20000, 25000, 30000, 35000, 40000, 45000, 50000, 60000, 70000, 80000, 90000, 100000, 150000, 200000, 250000, 300000, 350000, 400000, 500000, 600000, 700000, 800000, 900000, 1000000, 2000000, or 5000000 nucleic acid molecules are loaded per well in a droplet digital PCR reaction. In a specific embodiment, up to 10,000 nucleic acid molecules are loaded per well in a ddPCR experiment wherein the sample is partitioned into approximately 20,000 droplets. At increasing concentrations of target nucleic acid molecule, the higher the likelihood of having multiple templates in a single droplet, which results in an amplification bias towards shorter templates. It is understood by one of skill in the art how to adjust nucleic acid concentration in a ddPCR sample, in view of factors such as estimated target amplicon frequency or number of droplets generated for ddPCR platform.

In certain embodiments, the methods described herein further comprise a step of measuring the quantity of the nucleic acid molecule. In some embodiments, the size and quantity of the nucleic acid molecule is determined simultaneously. The quantity of the nucleic acid molecule may be calculated using Poisson statistics:

$$\lambda = -\ln(1-p)$$

where $\lambda$ is the average number of amplicon molecules per droplet and p is the fraction of positive droplets. From $\lambda$, together with the volume of each droplet and the total number of droplets analyzed, an estimate of the absolute amplicon concentration is calculated.

Methods for determining the size of a nucleic acid molecule using the ddPCR system disclosed herein may be used to determine the sizes and distribution of sizes of nucleic acid molecules in a sequencing library prepared for NGS platforms. In certain embodiments, the NGS platforms use adapter sequences. Primers and probes may be designed to anneal to specific adapter sequences.

Methods for determining the size of an unknown nucleic acid molecule using the ddPCR system disclosed herein may also be used for studying rare events that cannot be detected using other systems, such as deletions or copy number variations, which are implicated in a wide range of human pathologies (Sudmant et al., 2010, Science 330:641-646). Determining the size and quantity of unknown nucleic acid molecules using the methods provided herein may also be useful in studying samples where there are multiple sizes of deletions that could possibly occur within known regions. Methods that combine sizing and quantification may also be useful for determining ligation efficiency, as it allows for the simple comparison of quantity of different sized products with a single primer set within a single reaction well.

EXAMPLES

Example 1

Digital Quantification of Random Mitochondrial DNA Deletions

The following example demonstrates that, as provided by the instant disclosure, for example, a new procedure for quantitative analysis of rare mtDNA deletion events has been developed. This assay, termed Digital Deletion Detection (3D), allows for direct quantification and characterization of rare site-specific deletions that occur at frequencies as low as 1 deletion per $10^7$ genomes. This assay was used to determine the endogenous, absolute frequencies of random deletions at three sites of the mtDNA. 3D was also used to quantify the increased frequency of deletions induced by an exonuclease-deficient polymerase γ. Furthermore, random deletions were captured, the breakpoints sequenced and flanking regions characterized. Thus, 3D allows monitoring of de novo deletion events, characterization of mechanisms of deletion and the kinetics of expansion, and facilitates a better understanding of the mechanisms of mtDNA maintenance. Moreover, 3D has high potential as a tool to explore the utility of mtDNA deletions as biomarkers for disease.

Methods

Polga Knock-in Mice

Hind limb skeletal muscle samples from three homozygous Polga$^{+/+}$ and three Polga$^{-/-}$ knock-in mice, age 13-15 months, were received from Dr. J. Wanagat (University of California, Los Angeles, Calif.).

D274A-HeLa Cells:

Human polymerase gamma (pol γ) was ordered as a cDNA from ATCC (Manassas, Va.), catalog number 7488604 (Manassas, Va.). The D274A mutation was generated via site directed mutagenesis using the following primers: 5'-GCA CAA TGT TTC CTT TGC CCG AGC TCA TAT CAG GG-3' (SEQ ID NO:1) and 5'-CCC TGA TAT GAG CTC GGG CAA AGG AAA CAT TGT GC-3' (SEQ ID NO:2). Mutagenesis was performed using the QuickChange™ Site-Directed Mutagenesis Kit (Stratagene) with the following modifications: the 50 µl reaction consisted of 1× Pfu Ultra reaction buffer, 125 ng each oligo, 56 ng of plasmid DNA, 300 µM each dNTP mix, and 375 U Pfu Ultra polymerase (Stratagene). To amplify the plasmid, the following thermal cycle protocol was followed: initial denaturation at 95° C. for 2 minutes, 18 cycles of 95° C. for 40 sec, 58° C. for 50 sec, and 68° C. for 12 min, followed by a final elongation step of 68° C. for 7 min. The remainder of the protocol followed the manufacturer's recommendations. Mutagenesis was confirmed by sequencing. WT and D274A pol γ were excised out of the original pCMV-Sport6 vector using SalI and NotI and subsequently cloned into the pTRE-Tight-BI-AcGFP1 Tet-On mammalian expression vector (Clontech). Proper insertion into the expression vector was confirmed by sequencing.

The recombinant pol γ was transfected into HeLa Tet-On® Advanced Cell Line (Clontech) using FuGENE® HD Transfection Reagent (Roche) following the manufacturer's recommended protocol. Single clones were isolated by ring cloning and screened for GFP expression using a Guava EasyCyte 8HT benchtop flow cytometer (Millipore). Expression of pol γ was confirmed by RT-PCR using the SuperScript III First-strand RT-PCR kit (Invitrogen). Tet-on HeLa cell lines were cultured in high-glucose DMEM supplemented with 10% FBS (Tet-system approved), penicillin/streptomycin and 50 µg/ml each of geneticin and hygromycin in a 5% $CO_2$ atmosphere at 37° C. Recombinant pol γ expression (D274A or WT) was induced by continuous treatment with 2 µg/ml doxycycline for 21 days.

DNA Isolation:

To obtain whole DNA from the mouse muscle, tissue samples (~50 mg) were immersed in 5 mL homogenization medium (0.32 M sucrose, 1 mM EDTA, 10 mM Tris-HCl, pH 7.8) and disrupted with a glass Dounce-type homogenizer. The homogenate was transferred to a 15 mL tube and centrifuged at 13000 g. The pellet was re-suspended in 3 mL lysis buffer (10 mM Tris-HCl, pH 8.0, 150 mM NaCl, 20 mM EDTA, 1% SDS, and 0.2 mg/ml Proteinase K) and incubated at 55° C. for 3 hr. DNA was isolated by phenol-chloroform extraction followed by isopropanol precipitation.

To obtain whole DNA from HeLa cells, cell pellets (~1 million cells) were re-suspended in 3 mL lysis buffer (10 mM Tris-HCl, pH 8.0, 150 mM NaCl, 20 mM EDTA, 1% SDS, and 0.2 mg/ml Proteinase K) and incubated at 55° C. for 3 hr. DNA was isolated by phenol-chloroform extraction followed by isopropanol precipitation.

Endonucleolytic Enrichment of mtDNA Deletions:

Rare deletion-bearing molecules were selectively enriched through endonucleolytic destruction of wild type target sites. First a 400 µl digestion reaction was prepared containing 10 µg of genomic DNA, 8 µl (800 U) of TaqI (New England Biolabs), and TaqI reaction buffer (Fermentas). The reaction mixture was divided into 4×100 µl reactions and incubated at 65° C. for 4-6 hours. An additional 200 U of TaqI were added to each reaction every hour. After each TaqI addition, samples were thoroughly mixed and briefly centrifuged to ensure efficient digestion. Following the digestion procedure, the reactions were recombined, extracted once with phenol/chloroform/isoamyl alcohol (25:24:1, v/v), precipitated by ethanol, and re-suspended in 1 mM Tris, pH 8.

Taqman Probe and Primer Design:

The following primer/probe sets were used with mouse total DNA for mtDNA deletion detection. Control site: 5'-GAC ACA AAC TAA AAA GCT CA-3' (forward primer) (SEQ ID NO:3), 5'-ACA TTA CTG CAG GAC ACT TA-3 (reverse primer) (SEQ ID NO:4), 5'-6FAM-CCA ATG GCA TTA GCA GTC CGG C-MGB-3' (probe) (SEQ ID NO:5). Major arc: 5'-AGG CCA CCA CAC TCC TAT TG-3' (forward primer) (SEQ ID NO:6), 5'-AAT GCT AGG CGT TTG ATT GG-3' (reverse primer) (SEQ ID NO:7), 5'-6FAM-AAG GAC TAC GAT ATG GTA TAA-MGB-3' (probe 1) (SEQ ID NO:8), 5'-6FAM-TGA GGT CTG GGT CATT-MGB-3' (probe 2) (SEQ ID NO:9). $O_L$ site: 5'-CAA TAA CCC TAC CCC TAG CC-3' (forward) (SEQ ID NO:10), 5'-GTC AGT TTC CAA AGC CTC CA-3' (reverse) (SEQ ID NO:11), 5'-6FAM-ACT AGT ATA TCC TAA ACT TC-MGB-3' (probe 1) (SEQ ID NO:12), 5'-6FAM-TGC TTT TGT TAT AAT TTT C-MGB-3' (probe 2) (SEQ ID NO:13).

The following primer/probe sets were used with human total DNA for mtDNA deletion detection. Control site: 5'-CTA AAA ATA TTA AAC ACA AAC TAC CAC CTA CCTC-3' (forward primer) (SEQ ID NO:14), 5'-GTT CAT TTT GGT TCT CAG GGT TTG TTA TAA-3' (reverse primer) (SEQ ID NO:15), and 5'-6FAM-CCT CAC CAA AGC CCA TA-MGB-3' (probe) (SEQ ID NO:16). Minor arc site: 5'-CGC CAC ATC TAC CAT CACC-3' (forward primer) (SEQ ID NO:17), 5'-GAT TAT GGA TGC GGT TGC TT-3' (reverse primer) (SEQ ID NO:18), 5'-6FAM-TTG ATG GCA GCT TCT GT-MGB-3' (probe) (SEQ ID NO:19).

Droplet Digital PCR:

The final concentration of digested DNA was adjusted to yield less than ~3500 positive molecules per µl, which is within the range of linearity for the Poisson calculation (Pinheiro et al., 2012, Anal. Chem. 84:1003-1011). Reaction mixtures (25 µl) contained ddPCR Master Mix (Bio-Rad), 250 nM TaqMan probe, 900 nM each of the appropriate flanking primers, and 1-2 µl of digested DNA (0-2 µg total). Reaction droplets were made by applying 20 µl of each reaction mixture to a droplet generator DG8 cartridge (Bio-Rad) for use in the QX100 Droplet Generator (Bio-Rad). Following droplet generation, 38 µl of the droplet emulsion were carefully transferred to a Twin.tec semi-skirted 96-well PCR plate (Eppendorf), which was then heat sealed with a pierceable foil sheet. To amplify the fragments, thermal cycling was carried out using the following protocol: initial denaturation step at 95° C. for 10 min, followed by 40 cycles of 94° C. for 30 sec and 63.5° C. for 4 min. The thermally cycled droplets were either (i) analyzed by flow cytometry for fluorescence analysis and quantification of deletion frequencies or (ii) disrupted and the PCR products recovered and sequenced in order to verify deletions and characterize the deletion sites. All experiments were performed in triplicate.

Analysis of Fluorescence Amplitude and Quantification of Deletions:

Following normal thermal cycling, droplets were individually scanned using the QX100™ Droplet Digital™ PCR system (Bio-Rad). Positive (deletion-bearing) and negative droplets were distinguished on the basis of fluorescence amplitude using a global threshold. The number of mutant genomes per droplet was calculated automatically by the accompanying software (QuantaSoft, Bio-Rad) using Poisson statistics:

$$\lambda = -\ln(1-p) \quad (2)$$

where $\lambda$ is the average number of mutant genomes per droplet and p is the fraction of positive droplets. From this, the absolute concentration of deletion-bearing genomes was calculated (Hindson et al. 2011, Anal. Chem. 83:8604-8610).

To quantify deletion frequency, ddPCR amplification is performed using two primer sets. The first primer set flanks the test region and measures the concentration of deletion bearing molecules. The second primer set flanks a distant region in the genome that bears no restriction recognition sites. This second set measures the concentration of all mtDNA genomes. Because de novo deletions are so rare, reactions using the different primer sets are run using different dilutions of the digested DNA, and the results normalized against the mass of total DNA in the reaction. Deletion frequency is calculated by taking the ratio of the normalized concentrations of deletion bearing mtDNA molecules to the total mtDNA molecules screened. Reactions that yielded less than 10 positive droplets per well were scored conservatively as having no positives above background (Pinheiro et al., 2012, Anal. Chem. 84:1003-1011).

Disruption of Droplet Emulsions:

Following thermal cycling, droplets were re-suspended by adding 1 volume of droplet reader solution and gently pipetting up and down, after which the emulsion was transferred to a clean 1.7 ml microcentrifuge tube. The volume of the solution was adjusted to about 200 µl, either through addition or removal of excess droplet reader oil. Emulsions were disrupted by addition of 200 µl chloroform and extracted twice with 150 µl 1 mM Tris, pH 8, following which the aqueous phases were removed to a fresh tube. The combined aqueous phases were then extracted again with phenol/chloroform/isoamyl alcohol (25:24:1, v/v) and the DNA precipitated with ethanol. The precipitated DNA was washed once with 70% ethanol, air-dried for 5 min, and re-suspended in 10-20 µl water.

Capillary gel electrophoresis and densitometry were performed using the QIAxcel Advanced Gel Electrophoresis System (Qiagen). Aliquots of the re-suspended DNA (1-5 µl) were removed and diluted for use in the capillary system following manufacturer's recommended protocols.

Cloning and Sequencing of ddPCR Products:

The ddPCR Master Mix used in the initial amplification contains dUTP in place of dTTP, making it unsuitable for cloning because of E. coli's endogenous uracil DNA glycosylases. A second round of PCR is needed to generate thymidine bearing amplicons. Additionally, nonspecific products often amplify in the droplets.

Although these artifacts do not bind the TaqMan probe and therefore do not affect quantification, they do interfere with cloning and sequencing of true deletion products. In order to select target-specific amplicons, the second round of PCR uses a set of nested primers that anneal to the TaqMan probe site. Reaction mixtures (25 µl) for the nested PCR contained GoTaq® Hot Start Colorless Master Mix, 900 nM each primer, and 5 µl of the re-suspended DNA from the initial ddPCR. Thermal cycling consisted of initial denaturation at 95° C. for 10 min, followed by 2 cycles of 94° C. for 30 sec, 58° C. for 30 sec and 63.5° C. for 4 min.

PCR products were cloned using the TOPO TA Cloning® Kit for Sequencing (Invitrogen) following the manufacturer's protocol with the following modifications. Ligation was performed using 1 µl of PCR product with incubation of the ligation reaction at room temperature for 1 hour. Two microliters of the ligation reaction were transformed into MAX Efficiency® DH5α™ competent cells (Invitrogen) following the recommended protocol. The cells were plated on LB agar media supplemented with 50 µg/mL kanamycin and grown at 37° C. overnight. Single colonies were picked into 1 mL LB media with 10% glycerol and incubated at 37° C. for 16 hrs. These cultures were frozen and sent to the University of Washington High Throughput Genomics Center for rolling circle amplification and capillary sequencing. Sequencing was performed using universal T7 and T3 priming sites on the pCR®4-TOPO plasmid.

Figure 5A:
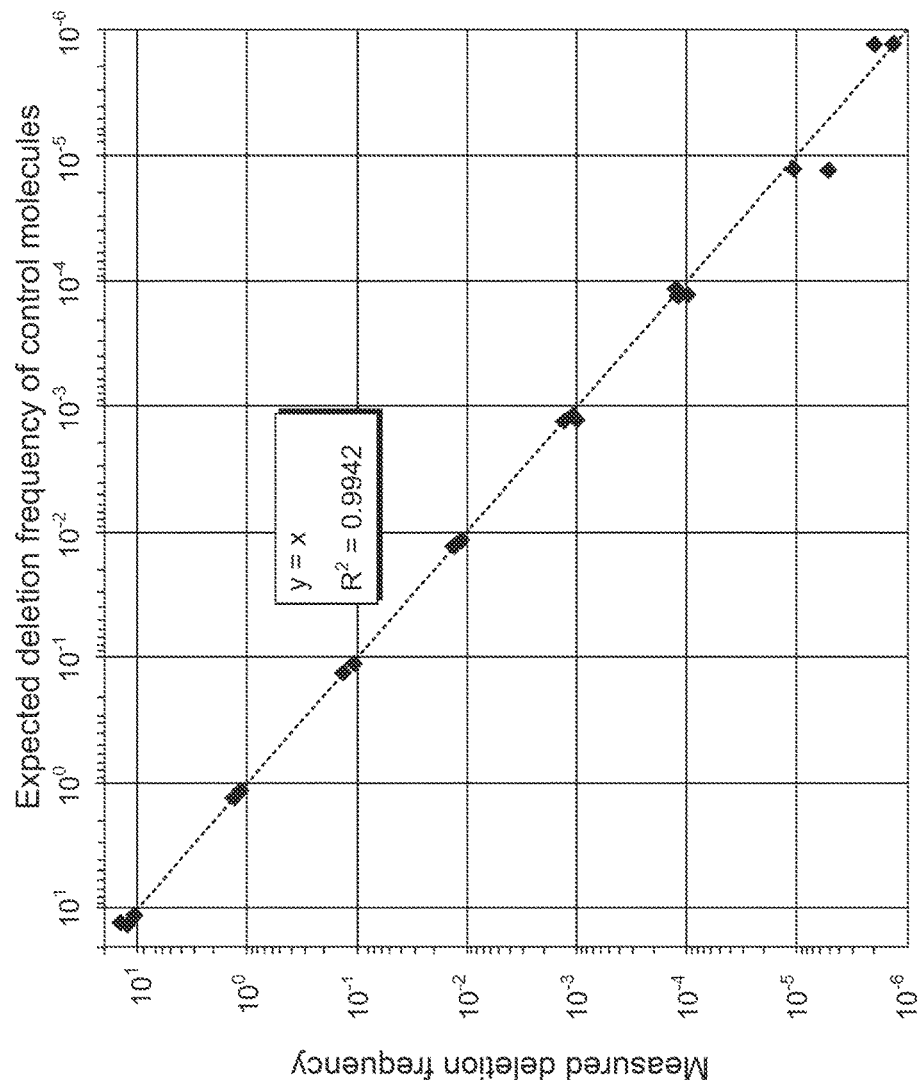
FIG. 5. Reconstruction (A) A control plasmid bearing the 3534Δ997 deletion was spiked at 3 molecules/μl into a serial dilution series of TaqI digested HCT 116 genomic DNA, and 3D analysis performed. The predicted deletion frequency of the control plasmid is plotted against the measured deletion frequency using the minor arc probe set. Each data point represents an individual experiment. The data were fit to y=x (dotted line) and the residuals calculated. (B) Concentration of plasmid controls as measured by 3D. Three plasmid controls (3534Δ997, 3719Δ809, and 3871Δ492) were diluted to an expected concentration of 300 molecules/μl/ template and subjected to 3D analysis, either singly or combined. 3D analysis was performed using two different primer concentrations: 900 nM and 45 nM. Error bars indicate the Poisson 95% confidence intervals for each concentration determination.
Figure 5B:
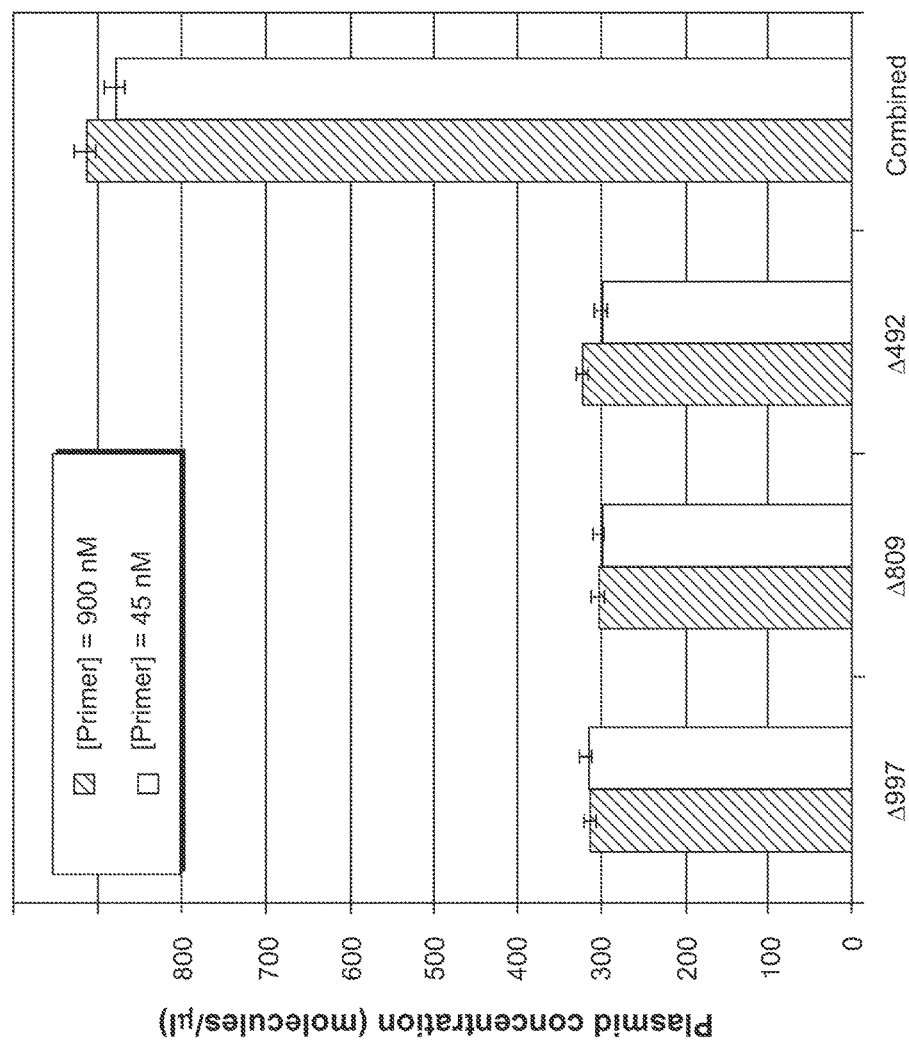

Reconstruction Experiments:

Genomic DNA was isolated from HCT 116 cells, chosen for its relatively low endogenous deletion frequency of $1.8 \times 10^{-7}$. Following TaqI digestion, a series of 10-fold serial dilutions of the genomic DNA were prepared, ranging over eight orders of magnitude. A 997 bp deletion was isolated, amplified, and cloned into a vector for use as a control molecule (FIG. 5b). Approximately 600 ng of the 3534Δ997 control plasmid was serially diluted 100 million fold and subjected to a preliminary 3D analysis in order to calculate the absolute concentration of molecules within the dilution. To each of the genomic dilutions, three copies of the 3534Δ997 control plasmid were added per microliter of reaction. The reactions were then partitioned, cycled, and the droplets analyzed to determine if the small concentration of the control molecules could be accurately assessed even in the presence of high concentrations of background, HCT 116 DNA.

Heterogeneous Population Reconstruction Experiments:

Three control plasmids (3534Δ997, 3719Δ809, and 3871Δ492) were isolated from D274A-HeLa cells as described above (see also FIG. 5). Each plasmid was serially diluted and subjected to preliminary 3D analysis in order to calculate the concentration of molecules within each dilution. Based on these quantifications, 300 molecules/μl/template were subjected to another round of 3D analysis, either separately or combined into a single reaction.

Results

Assay Design

Digital Deletion Detection (3D) is an extremely sensitive tool for the absolute quantification and characterization of rare deletion molecules. 3D allows for interrogation of a specific test region within a population of mitochondrial DNA (mtDNA) genomes in order to enumerate all deletions present within this region. The basic strategy behind 3D is essentially a two step process involving targeted destruction of wild-type (WT) target sites followed by partitioning of the intact mutant targets into individual "reaction chambers" or partitions for quantitative amplification (FIG. 1).

Figure 1B:
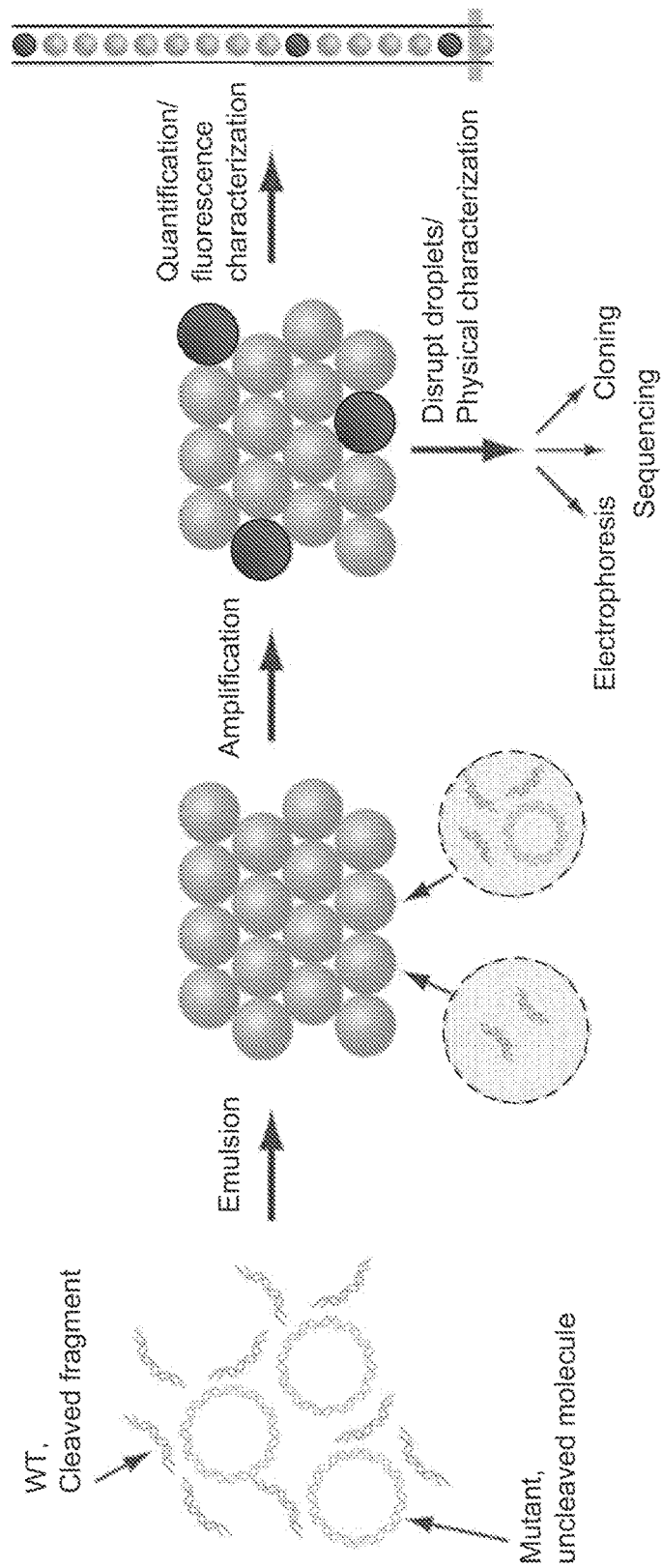

A region of mtDNA is defined by selecting an endonuclease and primer set (FIG. 1a). The endonuclease is chosen such that several recognition sites are contained within the target region (Vermulst et al., 2008, Methods 46:263-268). The primer pair is designed to be specific for sequence flanking the target region and corresponding recognition sites. Restriction endonucleases cleave WT target molecules at each of the several recognition sites, thus preventing PCR amplification with the flanking primers. However, if a deletion is present that removes the restriction sites, the target region between the primers remains intact, thus allowing for selective amplification of only the deletion-bearing molecules. Amplification of mutant molecules is facilitated through the use of droplet digital PCR (ddPCR) (Hindson et al., 2011, Anal. Chem. 83:8604-8610; Pinheiro et al., 2012, Anal. Chem. 84:1003-1011) (FIG. 1b). After digestion with the appropriate restriction endonuclease, the mtDNA molecules are sequestered into discrete, 1 nl water-in-oil emulsion droplets. Partitioning offers several other benefits that improve the sensitivity and accuracy of the assay. Sequestration of individual molecules in a heterogeneous population into separate reaction compartments eliminates competition for amplification among targets. The concentration of molecules within the droplets is adjusted such that most droplets contain no mutant genomes, while a small fraction contains at least one. During thermal cycling, only mutant molecules bearing deletions will successfully amplify, thereby creating a sub-population of droplets containing clonal amplicons derived from a single, deletion-bearing template. Because 3D quantification occurs at the endpoint rather than at a threshold value, variable PCR efficiencies become irrelevant for quantification.

The throughput, or total number of molecules that can be screened in a given reaction, is influenced by several factors, but is largely dependent on the total mass of DNA that is packaged within a single droplet. Because the droplets also contain large amounts of digested nuclear DNA, detection of deletions at lower frequencies may be possible depending on the relative sizes of the nuclear and mitochondrial genomes as well as the ratio of mitochondrial to nuclear DNA (Hindson et al, 2011, Anal. Chem. 83:8604-8610). Application mtDNA enrichment protocols during extraction will increase the relative proportion of total mtDNA within each droplet and thus the number of genomes screened per 3D assay.

Following thermal cycling, the droplets may be used in one of several process pathways for quantification and characterization of the isolated deletions (FIG. 1b). For example, with the aid of site-specific TagMan® probes, deletion-bearing droplets increase in fluorescence upon successful amplification of the mutant template. Droplets are then individually scanned through a specialized flow cytometer, whereby droplets containing amplifiable template (positives) and those that do not (negative) are distinguished based on fluorescence amplitude and directly enumerated (Hindson et al., 2011, Anal. Chem. 83:8604-8610). Poisson statistics are applied to calculate the average number of deletion-bearing molecules per droplet and the absolute concentration of mutant molecules is determined (Pinheiro et al., 2012, Anal. Chem. 84:1003-1011). Furthermore, the fluorescence amplitudes of the droplets can be used to make qualitative characterizations of the captured deletions. Alternatively, the droplets can be disrupted and the amplicons recovered. The captured deletions can then be directly characterized via gel electrophoresis, sequenced to determine breakpoints, or cloned for use in other downstream applications.

Measurement of Absolute Deletion Frequency and Mouse and Human Tissue:

Homozygous knock-in mice expressing exonuclease-deficient mitochondrial polymerase γ(exo− pol γ) demonstrate a significant increase in mitochondrial deletions that are associated with a progeroid phenotype (Vermulst et al., 2008, Nat. Genet. 40:392-394; Edgar et al., 2009, Cell Metab. 10:131-138). While previous studies have estimated the fold increase in deletion load, a quantitative analysis of absolute deletion frequency has yet to be achieved. Therefore used 3D was used to more precisely quantify mtDNA deletions in tissues expressing the exo− pol γ variant.

3D was applied to mtDNA isolated from muscle samples of homozygous mice that contained either the WT PolgA allele (Polga$^{+/+}$) or an exo− variant harboring a D257A mutation (Polga$^{-/-}$) (Vermulst et al., 2008, Nat. Genet. 40:392-394; Vermulst et al., 2007, Nat. Genet. 39:540-543). Primers designed to detect deletions in two target regions on the genome were used: one target region within the major arc (nt 8810-13117) and one target region that encompasses the light chain origin of replication ($O_L$, nt 4914-5571). The results of the 3D analysis are summarized in FIG. 2a-b and FIG. 3. For the Polga$^{+/+}$ mice, a frequency of 7±5 deletions per $10^7$ genomes at the major arc target region, i.e., $7 \times 10^{-7}$, was measured. At the $O_L$ target region, there was no detectable signal. Therefore, the upper limit for the deletion frequency was estimated to be approximately $1 \times 10^{-8}$, which represents the limit of sensitivity under the current conditions. Mice expressing the mutant polymerase gamma showed a marked increase in accumulated deletions at both sites (57±10 and 9.9±0.7 deletions per $10^7$ genomes at the major arc and $O_L$ target regions, respectively). These frequencies represent a nearly 9-fold increase in deletion frequency in the major arc, and at least a 60-fold increase in deletion frequency at the $O_L$.

Figure 2D:
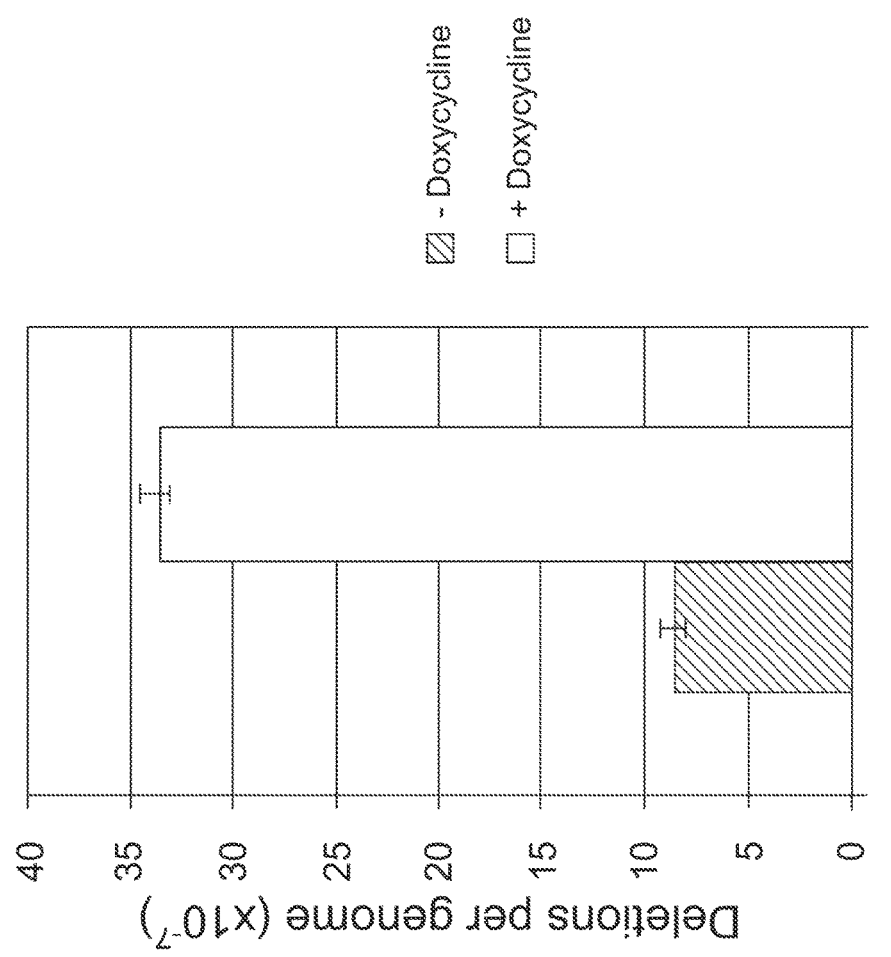

While exo− pol γ is known to cause an increase in point mutations in humans, an increase in large-scale deletions has not been demonstrated (Spelbrink et al., 2000, J. Biol. Chem. 275:24818-24828). To analyze the effect of exo− pol γ on the accumulation of mtDNA deletions in human cells, a HeLa cell line with stably expressed recombinant pol γ bearing a D274A mutation in the second exonuclease proofreading domain was established (Trifunovic et al., 2004, Nature 429:417-423; Foury & Vanderstraeten, 1992, EMBO J. 11:2717-2726; Kujoth et al., 2005, Science 309:481-484). The recombinant protein was placed under control of a tetracycline-inducible promoter to provide fine control on the temporal expression of the mutant. D274A-HeLa cells were grown for 21 days either in the presence or absence of doxycycline, after which the cells were harvested and the DNA isolated. 3D was applied to analyze the deletion frequency at a target region in the minor arc, spanning nucleotides 3468-4745. The control cells with no treatment were found to have a deletion frequency of $8.5 \pm 0.5 \times 10^{-7}$, whereas the cells receiving doxycycline treatment had a deletion frequency of $33.8 \pm 0.7 \times 10^{-7}$ (FIG. 2c-d and FIG. 4), demonstrating that the expression of the D274A mutant in human cells resulted in ~4-fold increase in minor arc target region deletions after 21 days of exo⁻ pol γ expression.

From this analysis, it is noted that deletion frequencies are not uniform throughout the mitochondrial genome, i.e., the deletion frequency is higher within the major arc versus the minor arc. This is consistent with available data from large numbers of patients with single and multiple deletions, which show that a majority of pathological mutations occur within the major arc (Ruiz-Pesini et al., 2007, Nucl. Acids. Res. 35:D823-828). Deletion of the light chain origin of replication is particularly rare, which is to be expected as its absence is predicted to severely impair mtDNA replication and propagation. However, the fact that the frequency of $O_L$ deletions can be induced to detectable levels may be interpreted as support for the existence of alternative origins (Brown et al., 2005, Genes Dev. 19:2466-2476).

Additionally, these results are significant in that it is the first study demonstrating an increase in accumulated deletions in human cells as a result of the expression of an exo⁻ pol γ. This result is made even more remarkable given that the mutant polymerase was only expressed for three weeks.

While expression of the exo⁻ pol γ resulted in an increase in the deletion frequency in both mouse and human and at all sites analyzed, this increase varied depending on the site within the genome from 4-fold to 9-fold to over 60-fold for the minor arc, major arc, and $O_L$ sites respectively. Furthermore, although it has been shown that over 90% of pathogenic mtDNA deletions are flanked by direct repeats of 3-13 by (Scheffler, I. E. *Mitochondria, 2nd* ed., Wiley-Liss, 2008), the conspicuous absence of such repeats in the deletions induced by the mutant pol γ at each of the three sites analyzed is noted (Table 1). Based on similar results, a role for the proofreading activity of pol γ in homolog-directed synthesis strand-break repair has been suggested (Vermulst et al., 2008, Nat. Genet. 40:392-394). However, we note that at the minor arc site, deletions mostly lacked homology even in the WT condition. Thus, the exonuclease domain may have a more general role in mtDNA strand maintenance beyond homology directed repair (Song et al., 2011, PLoS Computational Biology 7:e1002287).

Quantification of Known Concentrations of Plasmid Deletion Control Molecules:

The above experiments represent the first quantitative measurement of absolute deletion frequency for several target regions within mtDNA. To further validate mutation detection via 3D, a series of reconstruction experiments were performed. A plasmid harboring a known mtDNA deletion was analyzed at a constant concentration (3 copies/μl) against increasingly higher levels of genomic DNA (up to $2.5 \times 10^6$ copies/μl). 3D analysis was then performed to determine if the small concentration of the control molecules could be accurately assessed even in the presence of high concentrations of background DNA. The reconstruction demonstrated accurate recovery of target molecules over a range of six orders of magnitude of excess background mtDNA and confirmed the ability of 3D to accurately quantify rare deletion events (FIG. 5a).

Figure 7A:
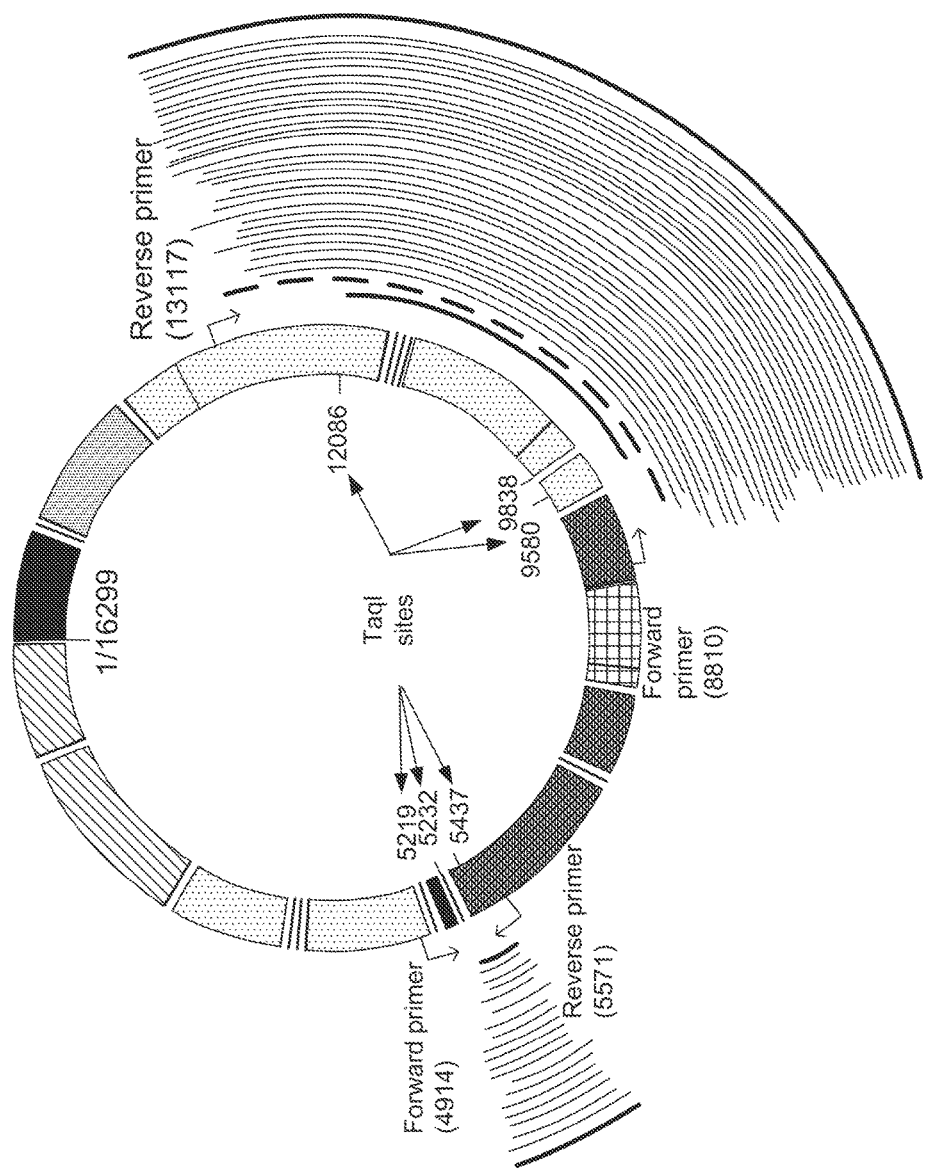
FIG. 7. Unique deletions induced by exonuclease-deficient pol γ and isolated by 3D. (A) Deletions at the major arc and $O_L$ sites mapped onto the mouse mitochondrial genome. Bold lines indicate the maximum and minimum deletion sizes for each site. The bold, dashed line at the major arc site indicates the common deletion. (B) Deletions at the minor arc site mapped onto the human mitochondrial genome. The bold, dashed lines indicate the three deletions that were used to generate the plasmid controls (from largest to smallest): 3534Δ997, 3719Δ809, 3871Δ492.
Figure 7B:
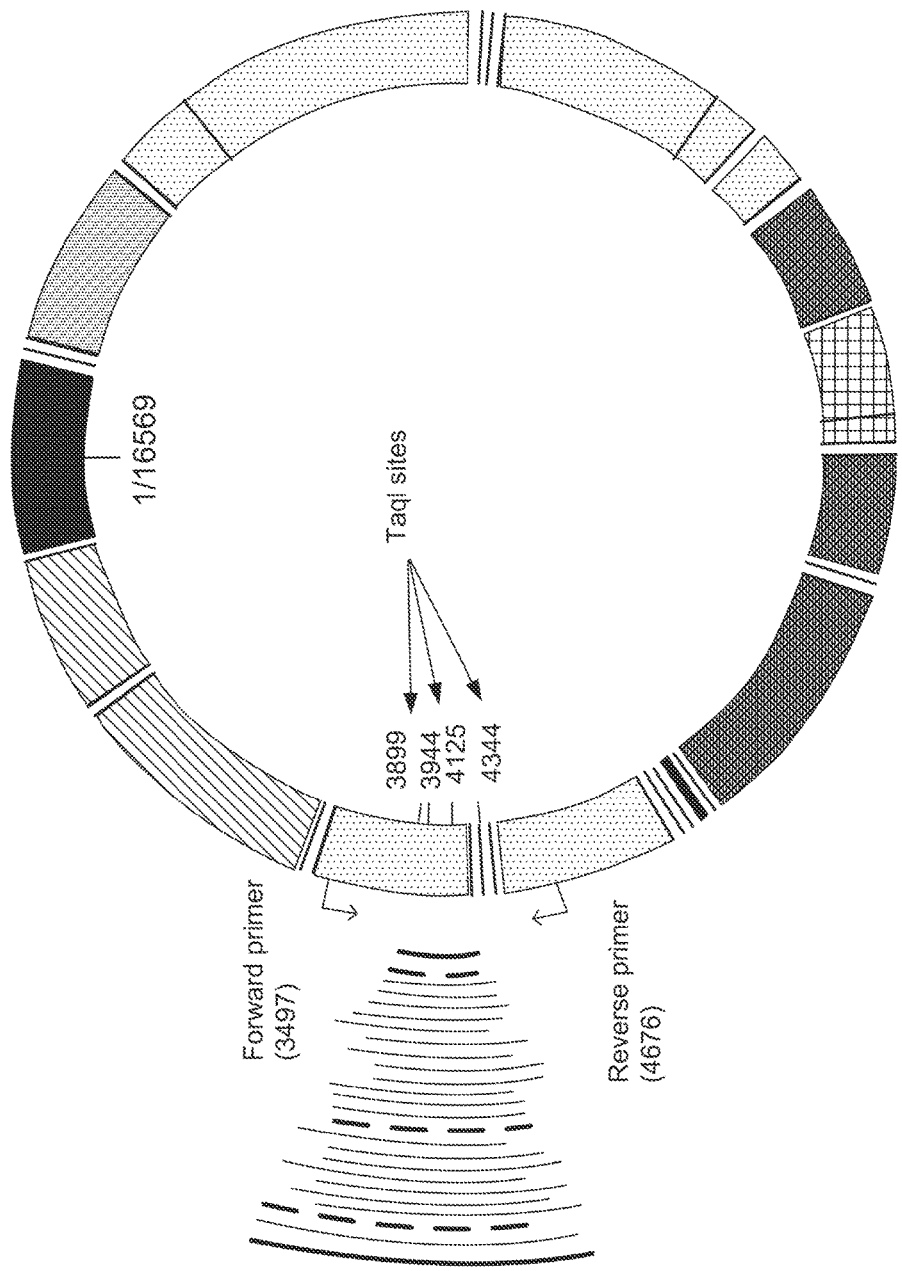

Next, the accuracy of quantification when 3D is applied to a heterogeneous population of deletions was characterized. To this end, three control plasmids, each containing a mtDNA fragment that harbors a unique deletion from the human mitochondrial genome (3534Δ997, 3719Δ809, and 3871Δ492, see FIG. 7b) were obtained. When used as a template in PCR, each yields different size fragments (185-bp, 372-bp, and 686-bp, respectively, with the minor arc 3D primer set). Equal amounts (300 molecules/template/μl) of each control plasmid were subjected to 3D analysis, either separately or combined into a single reaction, in order to determine if 3D could accurately report the known concentration of a mixture of target molecules. Furthermore, the analysis was performed with two different primer concentrations in order to optimize the amplification endpoints of each template for downstream processing (see also "Amplification factors" section below).

In the combined reaction, 3D quantification of the control plasmids should yield a final concentration of 900 total molecules/μl. 3D quantification of the individual plasmids yielded concentrations of 313±6, 304±6, and 322±6 molecules/μl, respectively at 900 nM primers, and 318±7, 303±6, 301±6 respectively at 45 nM primers (FIG. 5b and Table 1). Quantification of the combined reaction yielded a concentration of 915±12 molecules/μl at 900 nM primer and 881±11 molecules/μl at 45 nM primer. These values match the expected concentrations within the limits of uncertainty due to the stochastic effect associated with sampling of a dilute solution (Pinheiro et al., 2012, Anal. Chem. 84:1003-1011). Quantification was unaffected by primer concentration. These results demonstrate that 3D can accurately quantify a heterogeneous population of deletions across a wide spectrum of sizes.

TABLE 1 ddPCR data on the quantification of known concentrations of plasmid deletion control molecules using two different primer concentrations

| | [Primers] = 900 nM | | | | [Primers] = 45 nM | | | |
| --- | --- | --- | --- | --- | --- | --- | --- | --- |
| SampleID | Positive droplet counts | Negative droplet counts | Mean amplitude of positives | molecules/μl | Positive droplet counts | Negative droplet counts | Mean amplitude of positives | molecules/μl |
| 3534Δ997 | 10634 | 32276 | 9087.4 | 313 | 10046 | 29901 | 4805.1 | 318 |
| 3719Δ809 | 10083 | 31587 | 7582.9 | 304 | 10352 | 32652 | 4324.4 | 303 |

TABLE 1-continued ddPCR data on the quantification of known concentrations of plasmid deletion control molecules using two different primer concentrations

| | [Primers] = 900 nM | | | | [Primers] = 45 nM | | | |
| --- | --- | --- | --- | --- | --- | --- | --- | --- |
| SampleID | Positive droplet counts | Negative droplet counts | Mean amplitude of positives | mole-cules/μl | Positive droplet counts | Negative droplet counts | Mean amplitude of positives | mole-cules/μl |
| 3871Δ492 | 10620 | 31167 | 6705.2 | 322 | 10071 | 31948 | 4003.2 | 307 |
| Combined | 22468 | 17299 | 7970.6 | 915 | 25075 | 20400 | 4364.6 | 881 |

Figure 6A:
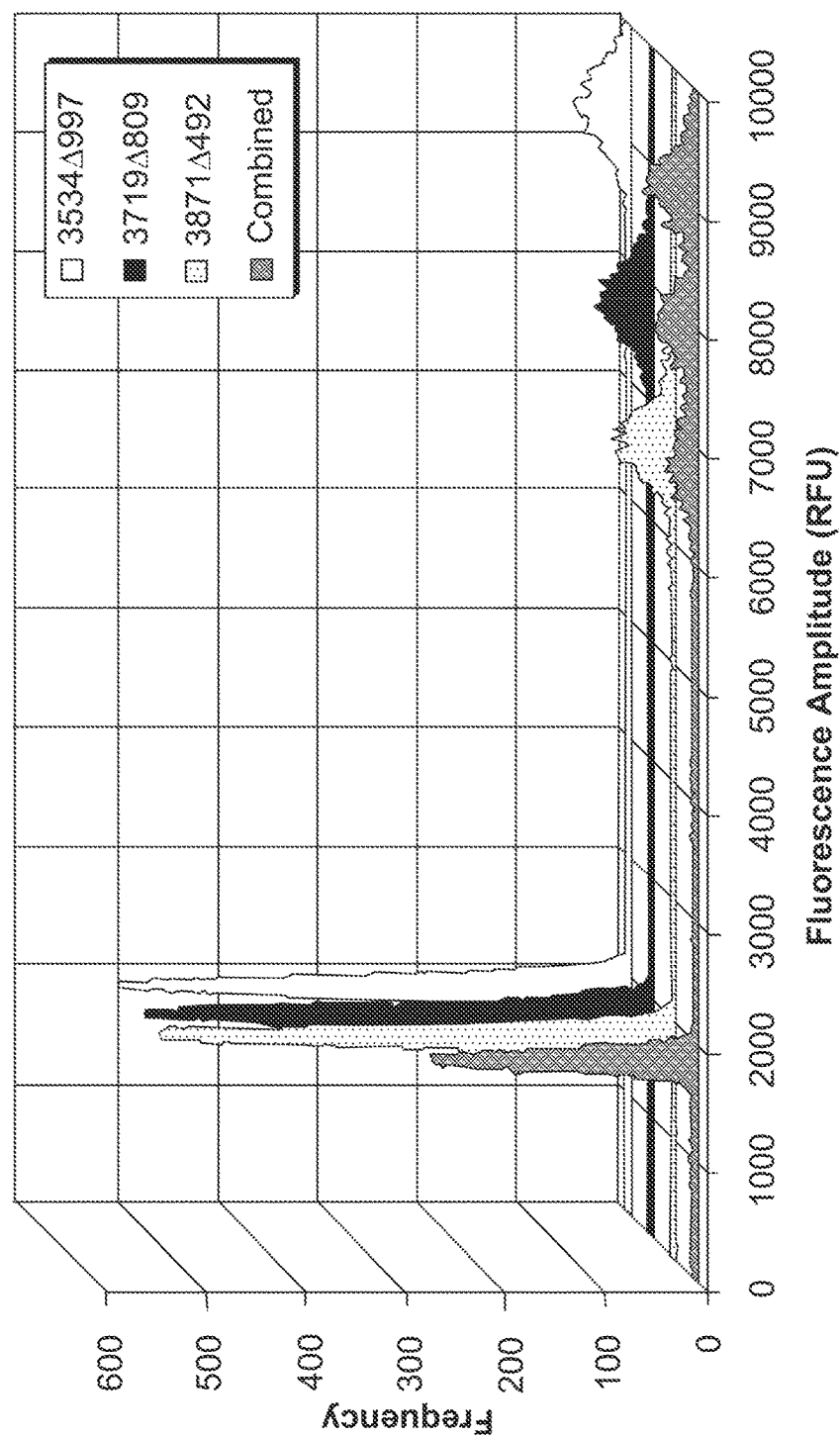
FIG. 6. Characterization of deletions by size. (A) Histogram of fluorescence amplitudes of droplets from 3D analysis of three deletion controls (individually and combined). Primer concentration is 900 nM. The global threshold is set at 2944. Populations of negative (below the threshold) and positive (above the threshold) are well defined. (B) Same as (A). Primer concentration is 45 nM, demonstrating the influence of primer concentration on relative fluorescence amplitudes of positive droplets. (C) The mean fluorescence amplitude (±s.d.) of positive droplets from (A) is plotted against expected amplicon size. Given the exponential nature of PCR amplification, the data were fit to an exponential expression demonstrating the relationship between amplitude and amplicon size. (D) Analysis of deletion size using capillary gel electrophoresis of recovered amplicons. 3D and conventional amplification was performed using two primer concentrations. The droplets were disrupted and the products were resolved and quantified via densitometry. Concentrations were normalized against the product length and compared against the Δ492 product in each reaction in order to calculate the relative amplification factor for each band.
Figure 6B:
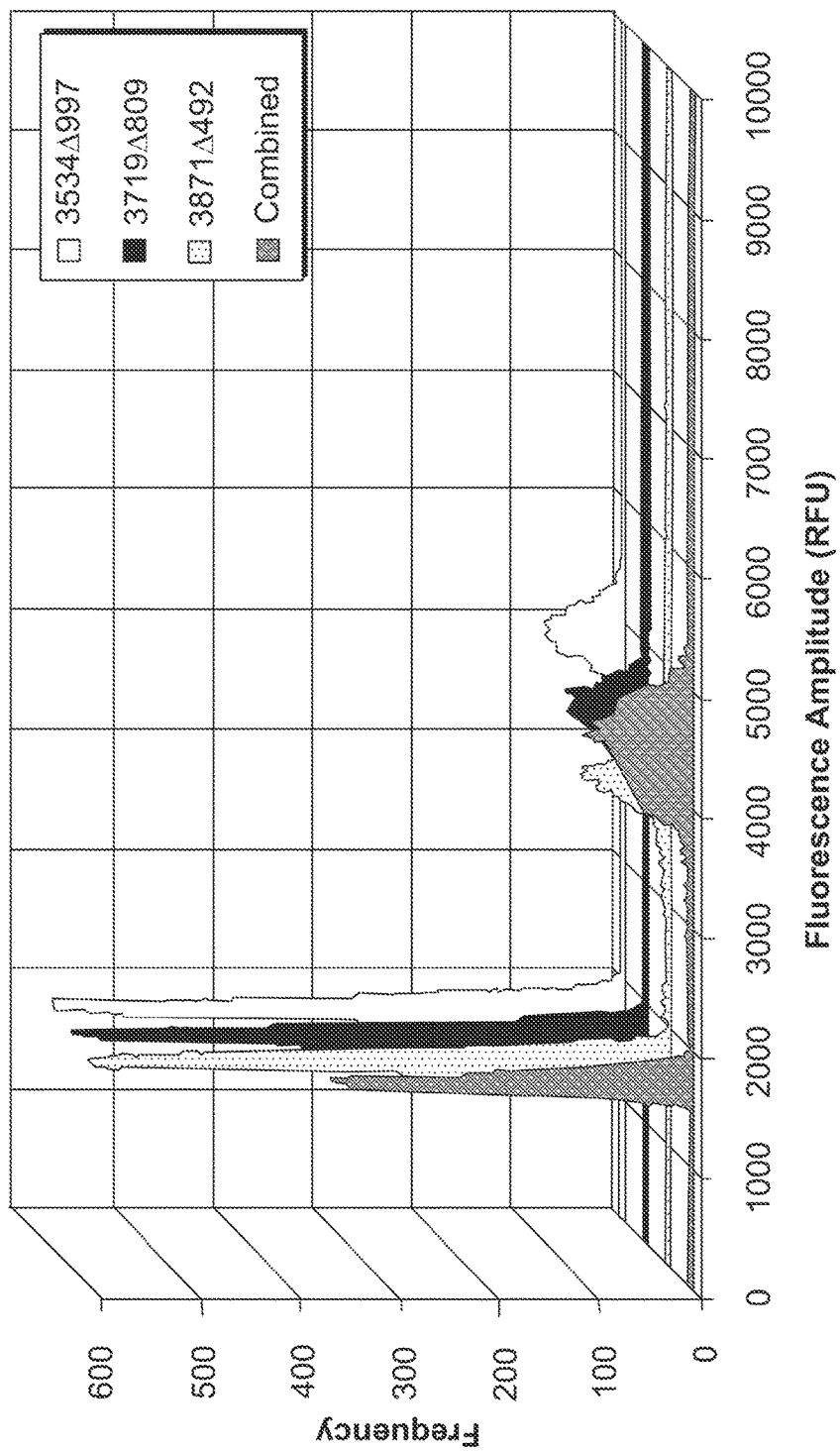
Figure 6C:
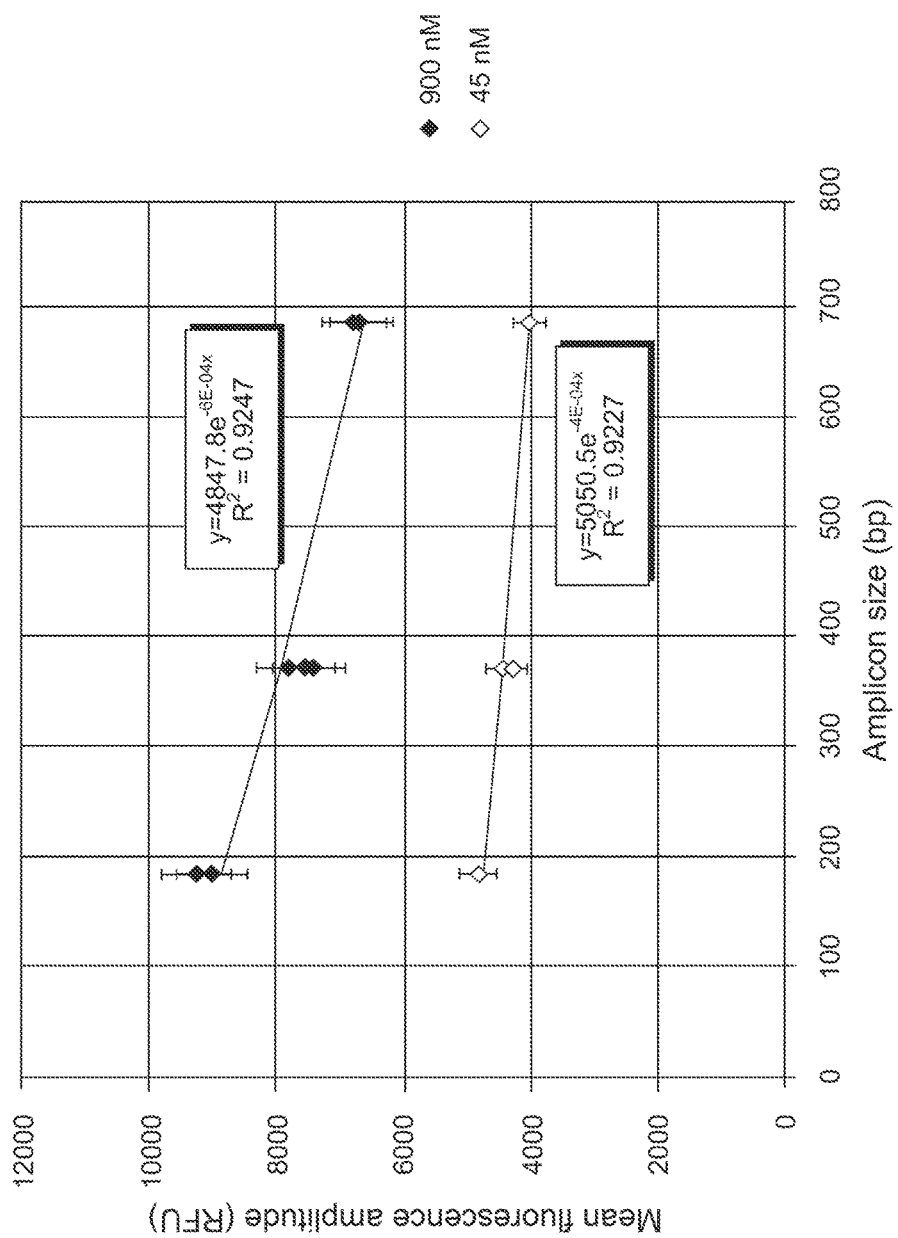

Characterization of Deletions by Size:

In addition to providing quantitative estimates of deletion frequency, 3D can be used to characterize sizes, proportions, sequences, and breakpoints of deletions. Analysis of fluorescence amplitudes of the three control plasmids following PCR reveals that the fluorescence intensity of a droplet is inversely proportional to the template size (FIG. 6). Furthermore, this pattern was maintained even in a complex mixture of all three control molecules, giving rise to a distinctive multimodal distribution in the fluorescence amplitudes (FIG. 6a). Because the amplitude reflects the reaction endpoint (which will vary depending on the size of the template and the availability of reagents), it follows that relative differences in amplitude can be amplified or minimized depending on the primer concentration (see "Amplification factors" section below). Provided that appropriate size standards are used to calibrate the signal, 3D can be used to provide semi-quantitative analysis of the spectrum of deletions present in a sample based on the relative fluorescence amplitudes of the positive droplets.

Figure 6D:
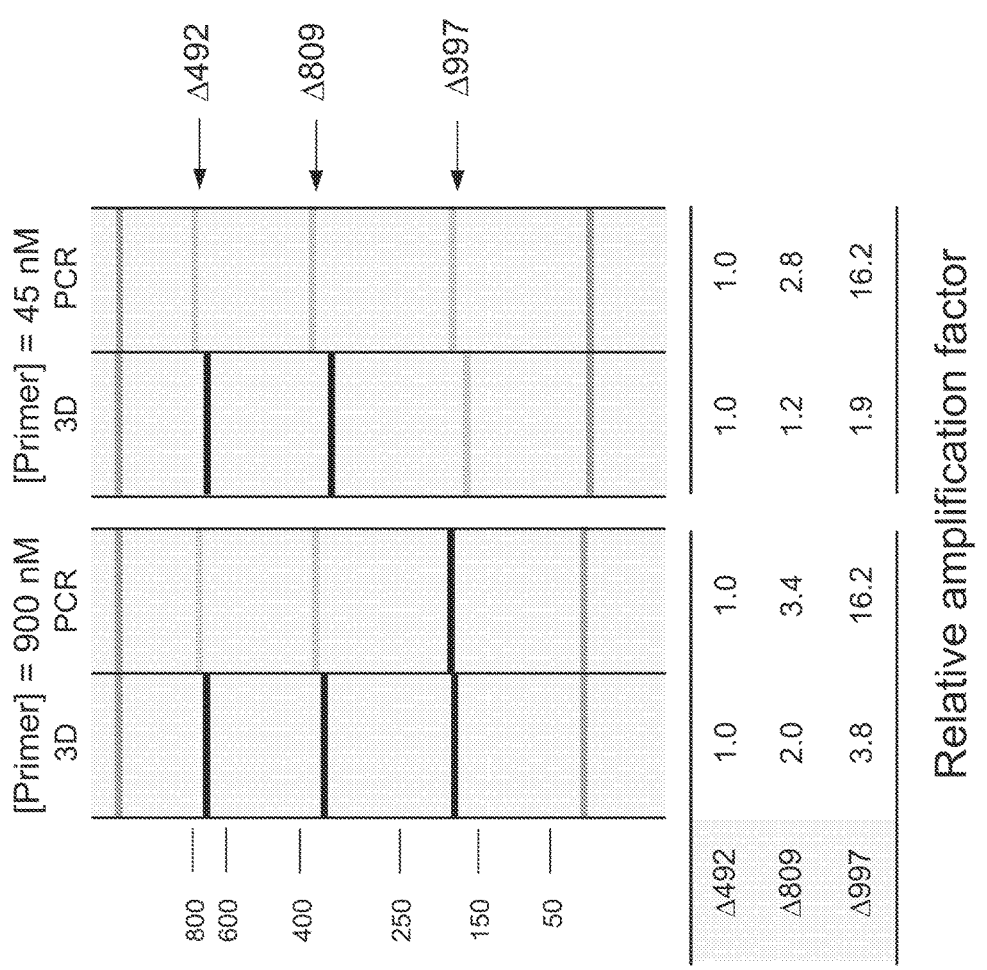

For more specific characterization of deletions, the droplets can be disrupted and the amplicons analyzed directly via gel electrophoresis (FIG. 6d). Following thermal cycling, droplets bearing a mixture of the three control plasmids were broken, and the products analyzed using a capillary electrophoresis system. In addition to directly assessing the sizes of all major deletion products present, the concentrations of the individual amplicons were measured. By using a lower primer concentration, amplification bias of the different sized products is minimized, allowing for use of relative concentrations of the amplified products as an estimate of the proportion of templates in the original sample (FIG. 6d). This estimate may be further refined through the use of a statistical correction that accounts for the small fraction of droplets that contain multiple templates (see also Residual amplification bias section below).

Characterization of Deletions by Sequencing:

Captured deletions can also be sequenced in order to precisely define their specific size or location. For example, in order to gain insight into the role of pol γ in mtDNA maintenance, genomic DNA from the Polga$^{+/+}$ and Polga$^{-/-}$ mice were subjected to 3D, amplifying deletions at both the major arc and $O_L$ target regions. DNA isolated from the D274A-HeLa cells was similarly treated, amplifying deletions at the minor arc target region. The thermally cycled emulsion droplets were disrupted and the amplified fragments recovered, cloned and sequenced. The results of the sequencing analysis (FIG. 7 and Table 2) reveal several interesting features. At the major arc target region, 63 of the 64 confirmed deletion sequences from the Polga$^{+/+}$ mice bore an identical 3874 by deletion corresponding to the mouse "common" deletion. This sequence was flanked by the canonical 15 by direct repeat. In contrast, in the Polga$^{-/-}$ mice, we sequenced 31 unique deletions at the same site, of which 90% showed less than 3 by of homology at the flanking sequences. At the minor arc target region, 24 unique deletions in the HeLa mtDNA were sequenced after induction of the mutant D274A pol γ, compared to 7 unique deletions from cells with no induction. However, unlike deletions within the major arc, no significant homology was found flanking the deletions within the minor arc under either condition. At the $O_L$ target region, no deletions from the Polga$^{+/+}$ mice were isolated after screening over 700 million genomes. However, from the Polga$^{-/-}$ clones, 37 sequences were obtained comprising 18 unique deletions ranging in size from 304-611 bp. Of the 18 unique deletions, 88% showed less than 3 by of homology at the flanking sequences.

TABLE 2

Sequencing Analysis of Deletion Mutations from Polga$^{+/+}$ and Polga$^{+/+}$ mice

| | | WT | | | Mut | | |
| --- | --- | --- | --- | --- | --- | --- | --- |
| | | Unique deletions (Total analyzed) | Min (bp) | Max (bp) | Unique deletions (Total analyzed) | Min (bp) | Max (bp) |
| Major arc | Total | 2 (64) | 3874 | 4076 | 31 (95) | 3597 | 4174 |
| | <3bp | 1 | | | 28 | | |
| | >3bp | 1 | | | 3 | | |
| $O_L$ | Total | 0 | | | 18 (37) | 304 | 611 |
| | <3bp | 0 | | | 16 | | |
| | >3bp | 0 | | | 2 | | |
| Minor arc | Total | 7 (69) | 519 | 997 | 24 (82) | 492 | 1101 |
| | <3bp | 7 | | | 20 | | |
| | >3bp | 0 | | | 4 | | |

Amplification Factors:

Although 3D is able to accurately quantify the total number of heterogeneous deletions from a population, certain challenges remain for characterization of the unique events from such a population. For example, in any PCR-based reaction where primers are not the limiting reagent, it is likely that smaller templates will have a larger amplification factor given that smaller quantities of dNTPs are consumed and smaller quantities of inhibiting pyrophosphates are produced. This is especially problematic in bulk PCR reactions where the smaller template will out-compete larger templates for amplification. Such asymmetric amplification may have a significant impact on downstream characterization procedures such as analytical gel electrophoresis, cloning, and sequencing. The hyper-partitioning of the 3D reaction largely circumvents this problem by providing separate reaction vessels for each template, thus preventing direct competition between different sized templates. Nonetheless, within each reaction droplet, smaller templates appear to undergo a larger amplification factor, producing far more amplified fragments than an equivalent droplet bearing a larger template. This effect is evident in the differences in the mean fluorescence intensities of droplets bearing the different control plasmids, where we note a marked inverse relationship between the mean fluorescence amplitude and the predicted amplicon size (FIG. 6).

In order to minimize amplification bias, 3D analysis was repeated, significantly reducing the primer concentration 20-fold from 900 nM to 45 nM. Under conditions of limiting primer, the amplitudes were reduced nearly 2-fold, resulting in a smaller amplification bias across the different template sizes (FIG. 6, Table 3). This result was further confirmed by directly measuring the concentration of amplified fragments via capillary gel electrophoresis (FIG. 6d). Importantly, although the endpoint amplitude was reduced, the quantification of absolute plasmid concentrations by 3D remained unaffected (FIG. 5b).

$$\lambda = \frac{M * V_d}{1000} \quad (3)$$

where M is the total concentration of templates per µl, and $V_d$ is the mean droplet volume (0.91 nl) (Pinheiro et al., 2012, Anal. Chem. 84:1003-1011). The Poisson function used in (1) is expressed as $$Poiss(\lambda, k) = \frac{\lambda^k e^{-\lambda}}{k!} \quad (4)$$

Next the number of droplets ($N_2$) that contain at least one copy of the next shortest template ($T_2$) is calculated, excluding those that contain any longer piece:

TABLE 3 ddPCR data on the quantification of known concentrations of plasmid deletion control molecules using two different primer concentrations.

| | [Primers] = 900 nM | | | | [Primers] = 45 nM | | | |
|---|---|---|---|---|---|---|---|---|
| SampleID | Positive droplet counts | Negative droplet counts | Mean amplitude of positives | molecules/µl | Positive droplet counts | Negative droplet counts | Mean amplitude of positives | molecules/µl |
| 3534Δ997 | 10634 | 32276 | 9087.4 | 313 | 10046 | 29901 | 4805.1 | 318 |
| 3719Δ809 | 10083 | 31587 | 7582.9 | 304 | 10352 | 32652 | 4324.4 | 303 |
| 3871Δ492 | 10620 | 31167 | 6705.2 | 322 | 10071 | 31948 | 4003.2 | 307 |
| Combined | 22468 | 17299 | 7970.6 | 915 | 25075 | 20400 | 4364.6 | 881 |

Residual Amplification Bias:

The amplification bias in 3D was substantially reduced by reducing the primer concentration such that it becomes the limiting reagent. By doing so, an upper limit on the total number of amplicons that can be generated from any given template was set. While the bias was greatly reduced, it was not altogether eliminated (FIG. 6d). This is because template compartmentalization obeys a Poisson distribution and a small subset of reaction droplets will contain more than one template. In such cases, amplification of the smaller template will be favored as in conventional PCR reactions. If the input concentrations of each template are known (as is the case for the control reactions), then a statistical correction can be applied using combinatorics and the Poisson equation in order to account for biased amplification in partitions with multiple templates.

Presuming that in cases where multiple templates are found within the same partition that only the shortest template ($T_1$) will be amplified, then the total number of droplets ($N_1$) that contain at least one molecule of $T_1$ must first be calculated:

$$N_1 = N_{Total} \times \sum_{k=1}^{n} \left[ Poiss(\lambda, k) \times \sum_{r=1}^{k} \left[ \binom{k}{k-r} \times P_1^k \times (1 - P_1)^{k-r} \right] \right]$$

where $N_{Total}$ is the total number of droplets, $P_1$ is the probability of selecting the short template once from a pool of all available templates (equal to the relative concentration of the template), and n is the maximum number of templates found inside a single droplet. The average number of templates per droplet ($\lambda$) is found according to equation 3:

$$N_2 = \quad (5)$$
$$N_{Total} \times \sum_{k=1}^{n} \left[ Poiss(\lambda, k) \times \sum_{r=1}^{k} \left[ \binom{k}{k-r} \times P_2^r \times (1 - P_1 - P_2)^{k-r} \right] \right]$$

This process is repeated until all templates have been accounted for. Comparison of these values provides a correction for the relative amplification factor for each template. This procedure was applied to the relative amplification factors obtained from capillary gel electrophoresis, using, $N_{Total}$=45,475, $\lambda$=0.80171, n=6, and the following template concentrations (P):

| Template | P | N | Poisson Correction | Relative amplification factor | Template Proportion |
|---|---|---|---|---|---|
| 3534Δ997 | 0.3449 | 10985 | 0.56 × | 1.9 = | 1.1 |
| 3719Δ809 | 0.3286 | 7988 | 0.76 × | 1.2 = | 0.9 |
| 3871Δ492 | 0.3265 | 6103 | 1.00 × | 1.0 = | 1.0 |

As the total concentration of positive molecules is reduced in the sample, so is the need for this statistical correction.

Figure 8:
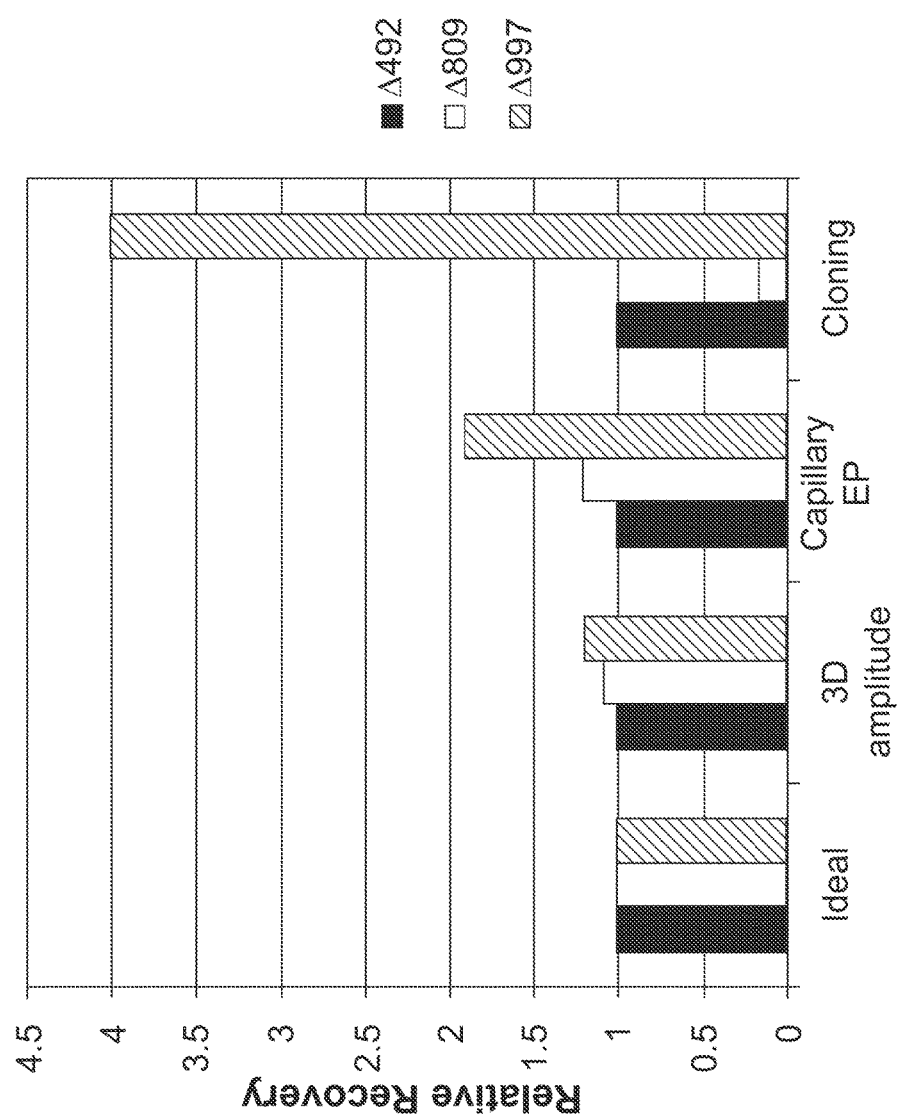
FIG. 8. Relative recovery of amplified products from plasmid controls. Relative recovery proportions are shown at various stages of 3D analysis. Values are normalized against Δ492.
Figure 9A:
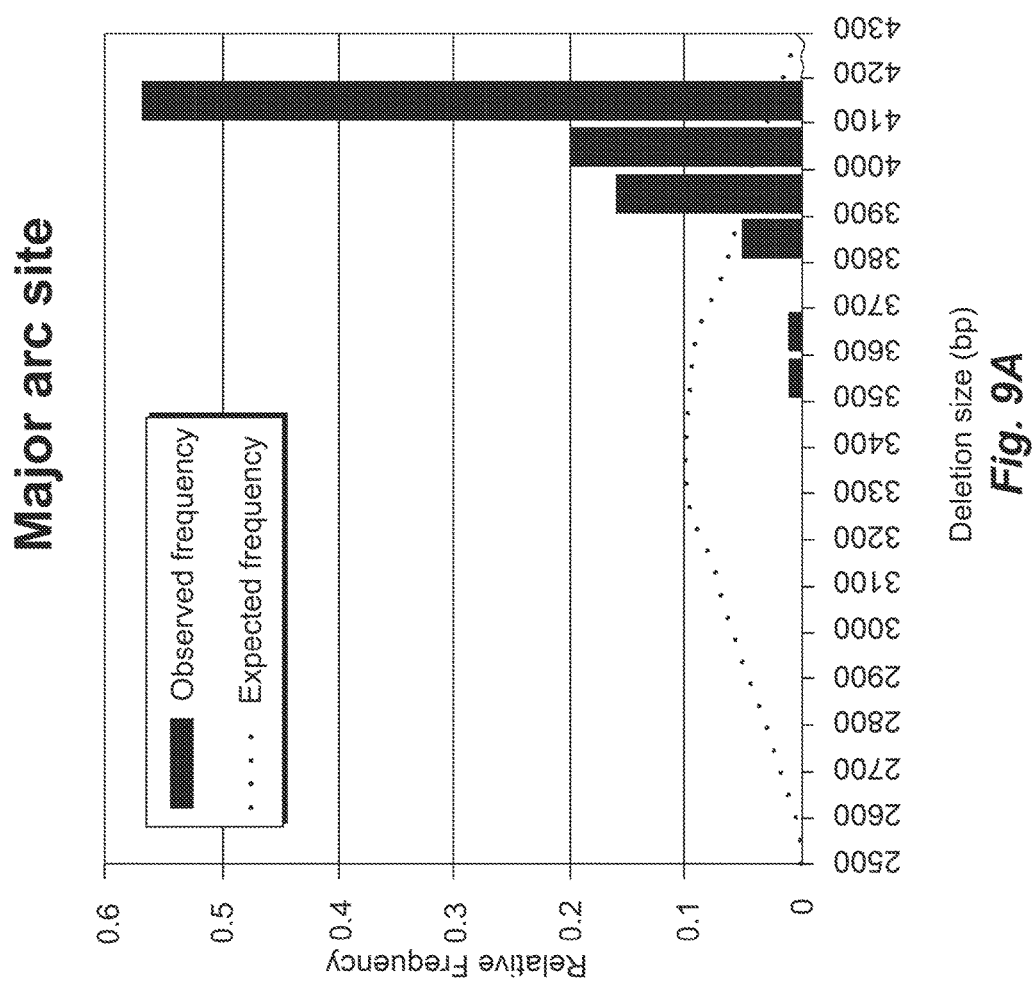
FIG. 9. Histograms showing size distributions of deletions sequenced from (A) the major arc target region, (B) the $O_L$ target region, and (C) the minor arc target region. The expected frequency was calculated from 25000 simulations allowing random break points in the respective target areas.
Figure 9B:
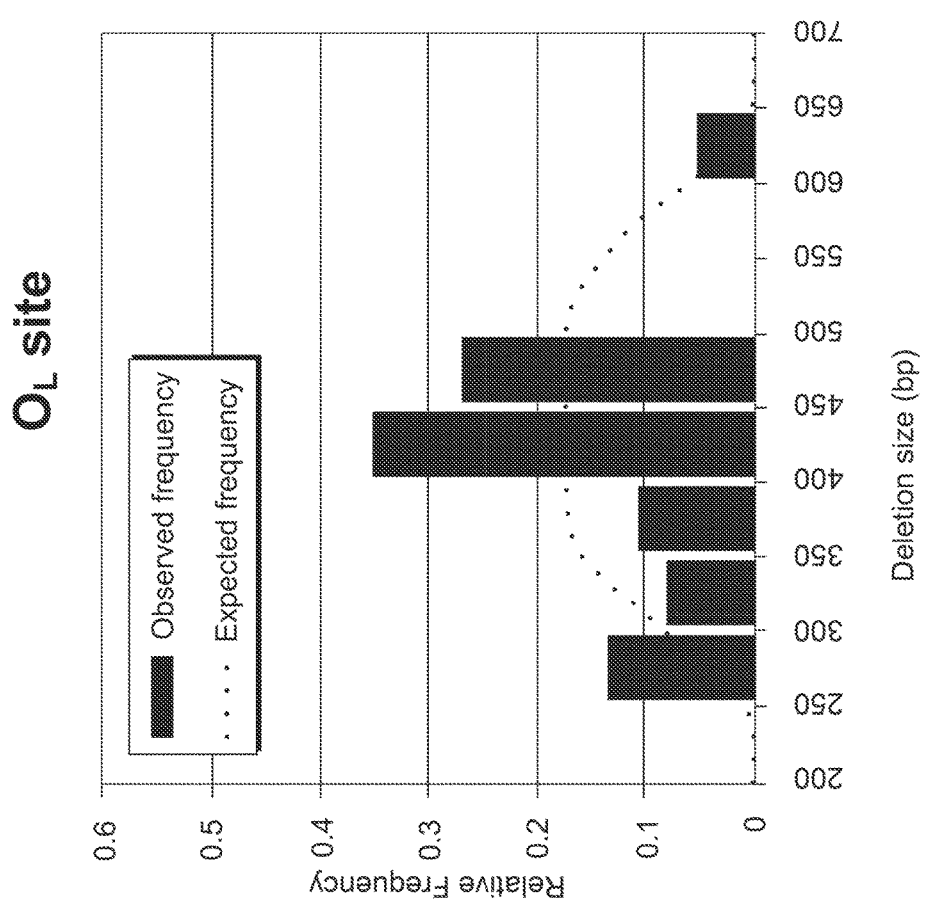
Figure 9C:
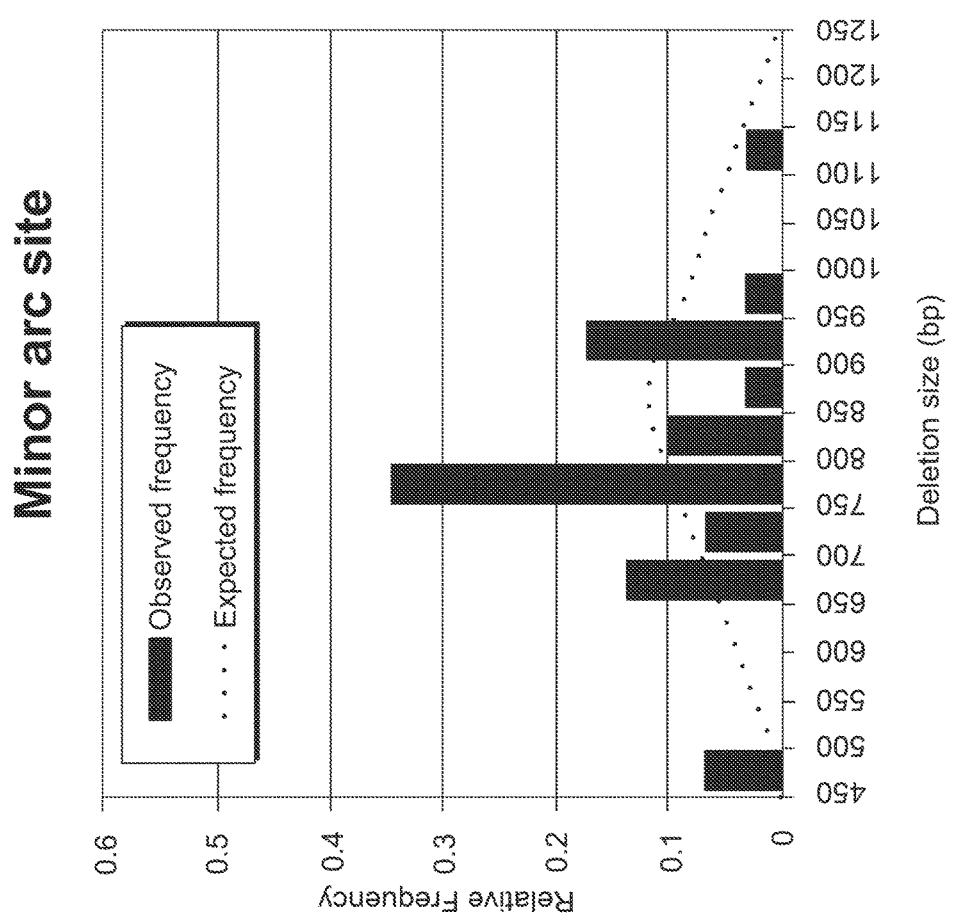

Sampling of Deletion Space:

By reducing the primer concentration, amplification is normalized across targets of all sizes such that the molar ratios of the amplified products are proportional to the ratios of their respective templates. It has been observed that some downstream applications used to characterize the deletions also present their own biases (FIG. 8). For example, cloning of the PCR products typically favors ligation of small inserts into the vector. As long as the possible inserts are of roughly comparable size, the methodology appears to adequately sample the possible deletion space. However, if a large distribution of deletion sizes is possible, cloning bias will favor capture of larger deletions (smaller fragments) (FIG. 9). While this could be bypassed by simply constructing additional primers at internal sites with a target region, such an endeavor is time and labor intensive. An alternative approach may be to employ deep sequencing technology. This would offer the added advantage of potentially being a far more comprehensive characterization than could be obtained by selecting some subset of colonies for analysis.

In summary, a digital deletion detection assay (3D) has been developed as a highly sensitive tool for detection, quantification, and characterization of rare mitochondrial deletion events occurring at frequencies near 1 in $10^7$ genomes. 3D is adaptable to any organism, and can be used to interrogate multiple sites within the mitochondrial genome to look for both random and specific deletions. Given these properties, 3D is a powerful tool to help identify new deletions associated with a variety of diseases, allow for the development of new assays using mtDNA deletions as biomarkers for diagnostic or early detection screening, and facilitate the study of the mechanisms of mtDNA maintenance, repair and expansion of pathogenic deletion mutations.

Example 2

Simultaneous Digital Quantification and Fluorescence-Based Size Characterization of Massively Parallel Sequencing Libraries The following example demonstrates, as provided in the instant disclosure, the application of droplet digital PCR to the process of preparing NGS libraries. The accuracy of quantification and size determination with this method by comparing the concentration and size predictions made with the method disclosed herein to the read numbers and lengths observed in a sequencing run on the Illumina MiSeq platform is highlighted. This method may be used to substantially increase the average data yield from NGS runs while adding user convenience, thereby increasing the overall efficiency and throughput of sequencing experiments.

Methods

Purification of DNA Fragments

An exACTGene™ molecular weight 50 by DNA Ladder (Fisher) and 1 kb Plus DNA Ladder (Fisher) were run on a 1.0% UltraPure Low-Melting Point Agarose (Invitrogen) electrophoresis gel and the 25, 50, 100, 200, 300, 400, 500, 600, 700, 800 and 1000 by ladder bands were manually excised. The DNA in these fragments was then purified using the QIAcube® automated gel extraction protocol with the QIAquick® Gel Extraction Kit (QIAGEN). The size and purity of all DNA fragments were verified by gel electrophoresis.

Ligation of DNA Fragments into Target Plasmid

Figure 10:
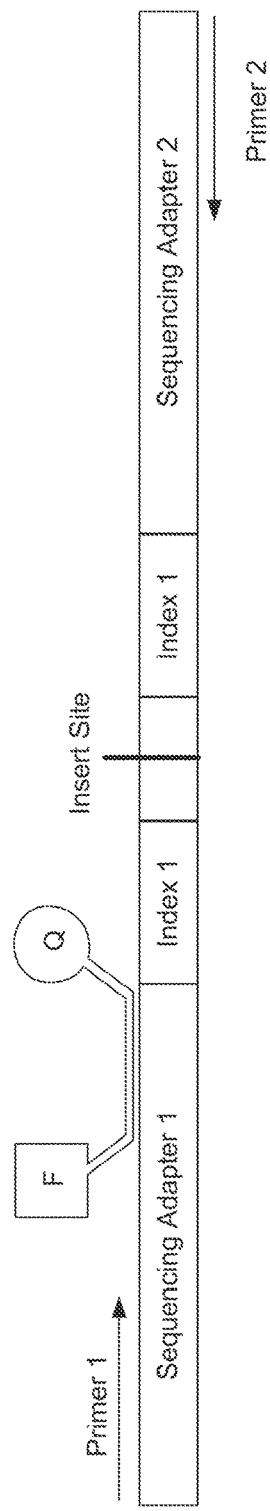
FIG. 10. Schematic representation of sequencing plasmid insert region. The size standards used in this study were created by ligating inserts ranging from 25 to 1000 base pairs into sequencing plasmids at the indicated restriction site. Similarly, the sequencing libraries used in this study were created by ligating sheared DNA into the insert site. The insert site is flanked on both sides by unique seven base pair indices (bar codes) and adapter sequences compatible with the Illumina MiSeq®. Each library was created with unique indices so they can be identified in a heterogenous mixture. A pair of primers and a fluorescent TaqMan® probe were designed to bind to the adapter regions so the same primers and probe can be used for the fluorescent amplification of the size standards and the MiSeq® libraries via ddPCR. The 5'-3' exonuclease activity of the polymerase cleaves the TagMan® probe upon amplification of the template DNA to free the fluorophore (F) from the quencher (Q), thereby increasing fluorescence of the system.

Samples of pUC-19 plasmid (Invitrogen) were modified to contain a SmaI restriction site flanked on both sides by seven-base pair indices unique to each plasmid and Nextera version 1 adapters (Epicentre Biotechnologies). The resulting construct will be referred to as "pJB" (FIG. 10). One of these pJB plasmids was digested with SmaI restriction endonuclease (New England BioLabs) for 2 hours at 25° C. The digested plasmid was treated with Calf Intestinal Alkaline Phosphatase (New England BioLabs) for 1 hour at 37° C. and heat inactivated for 15 minutes at 65° C. to remove the 5' phosphate group and prevent re-ligation. The plasmid was then run on a 1.0% UltraPure Low-Melting Point Agarose (Invitrogen) gel, and the band corresponding to the cut vector was manually excised and purified using the QIAcube® gel extraction protocol. The cut, dephosphorylated plasmid was then purified with a phenol/chloroform/isoamyl alcohol extraction.

Blunt-end ligations of the differently sized DNA fragments into the pJB plasmid were carried out in 20 μL reactions containing 1 μL at T4 DNA Ligase (New England BioLabs), 2 μL 10×T4 DNA Ligase Buffer (New England BioLabs), and a 1:3 molar ratio of plasmid to insert. The ligation reactions were incubated at room temperature for two hours.

One microliter of the ligation reaction was transformed into MAX Efficiency DH5α chemically competent cells (Invitrogen) following the vendor's protocol. The transformed cells were plated on LB agar media containing 100 μg/mL carbenicillin and grown overnight at 37° C. Five single colonies from each ligation reaction were picked into 5 mL LB media containing 100 μg/mL carbenicillin and grown overnight at 37° C. The ligated DNA was purified using the QIAcube® automated plasmid DNA purification protocol with the QIAquick® Spin Miniprep Kit (QIAGEN). The size and purity of each plasmid/insert ligation was verified by restriction digest and gel electrophoresis. The samples were also sent to the Fred Hutchinson Cancer Research Center ABI capillary sequencing facility to verify that the correct insert had been ligated into the plasmid in each sample.

Library Preparation for Illumina MiSeq®

Eight pJB constructs with unique seven-base pair indices were digested with SmaI, treated with Calf Intestinal Alkaline Phosphatase, and purified by phenol/chloroform/isoamyl alcohol extraction.

Samples of the plasmid pET-23a were sheared using the Covaris S220 Ultrasonicator set to shear DNA to an average size of 150 bp. Each sample of sheared DNA was run on a 1.0% UltraPure Low-Melting Point Agarose gel, manually excised, and purified using the QIAcube® gel extraction protocol. The sheared DNA was blunted and phosphorylated using the Quick Blunting Kit (New England BioLabs) and purified with a phenol/chloroform/isoamyl alcohol extraction.

Separate blunt-end ligations of sheared DNA fragments into the eight differently barcoded pJB plasmids were carried out in 20 μL reactions containing 1 μL T4 DNA Ligase (New England BioLabs), 2 μL 10×T4 DNA Ligase Buffer (New England BioLabs), and a 1:10 molar ratio of plasmid to insert. The ligation reactions were incubated at room temperature for 2 hours. All ligations were purified with a phenol/chloroform/isoamyl alcohol extraction.

One microliter of each ligated pJB library was transformed into MAX Efficiency DH5α chemically competent cells (Invitrogen) following the Invitrogen protocol. The transformed cells were grown overnight in 5 mL of LB media containing 100 μg/mL carbenicillin at 37° C. The pJB libraries were purified using the QIAcube® automated plasmid DNA purification protocol with the QIAquick® Spin Miniprep Kit (QIAGEN). Correct insert sizes were verified by diagnostic PCR and gel electrophoresis.

The region of each pJB library containing the Nextera adapters, indices, and sheared DNA insert was amplified using 20 cycles of standard PCR. All pJB libraries were quantified using the ddPCR system (Bio-Rad) and the Quant-iT PicoGreen assay (Invitrogen). The pJB size standards were run in parallel with the amplified libraries in a ddPCR experiment to allow for the estimation of the distribution of template sizes within each library. The measured concentrations of the eight differently indexed libraries were used to dilute and combine the libraries in a molar ratio of 100:50:10:1 with two libraries at each concentration. The combination of libraries was denatured and diluted in preparation for loading onto the Illumina MiSeq® flow cell as per the Illumina protocol.

TaqMan® Probe and Primer Design

A pair of 20-base pair oligonucleotide primers (Invitrogen) was designed flanking the region of the pJB plasmid containing the Nextera adapter sequences, indices and SmaI restriction site (FIG. 10). A 20-base pair TaqMan® probe with a FAM fluorophore (Applied Biosystems) complementary to a binding site within the amplified region was also designed for use in the QX100 ddPCR system.

Droplet Digital PCR

The plasmids containing different sized inserts were prepared for droplet PCR in 25 μL reactions containing 2× ddPCR Master Mix (Bio-Rad), 250 nM TaqMan probe (Applied Biosystems), 900 nM each of the appropriate flanking primers, and 10,000 copies of pJB plasmid DNA. One nanoliter reaction droplets were made by adding 20 μL of each reaction mixture to the sample wells of a droplet generator DG8 cartridge (Bio-Rad) and 70 μL ddPCR Droplet Generation Oil (Bio-Rad) to the oil wells of the cartridge for use in the QX100 Droplet Generator (Bio-Rad). Forty microliters of the generated droplet emulsions were transferred to Twin.tec semi-skirted 96-well PCR plates (Eppendorf), which were then heat sealed with pierceable foil sheets. To amplify the target DNA, the droplet emulsions were thermally cycled using the following protocol: initial denaturation step at 95° C. for 10 min, followed by 40 cycles of 94° C. for 30 sec, and 60° C. for 1 min. The fluorescence of each thermally cycled droplet was measured using the QX100 Droplet Reader and the amplitude of fluorescence was analyzed. All reactions were performed in triplicate.

Data Analysis

An equation of the line fitting the correlation between amplicon size and fluorescence amplitude for the size standards was generated using Excel (Microsoft) and applied to the measured fluorescence amplitude of the sequencing libraries to calculate amplicon size. The distribution of amplicon sizes estimated by ddPCR was compared to the distribution of library molecule lengths appearing in the MiSeq® data that passed the default quality filter. The .fastq data files produced by the MiSeq® were imported to Sequencher™ DNA sequence analysis software (Gene Codes) and aligned to the pET-23a plasmid sequence to generate a sequence alignment/map file (SAM). A perl script was used to count the length of each read pair by retrieving the number corresponding to the "TLEN" field of the SAM file. Only library molecules for which both paired-end reads passed the quality filter were included in the analysis.

Results

QuantiSize Assay Design

In addition to providing absolute quantification of target DNA, the ddPCR system may be used to measure the length of unknown amplifiable templates. This novel assay, referred to as "QuantiSize", takes advantage of a linear correlation demonstrated herein between the fluorescence amplitude of droplets and the size of amplicons within them. This example shows the application of QuantiSize assay to the process of preparing next generation sequencing (NGS) libraries. The accuracy of quantification and size determination with QuantiSize was assessed by comparing the concentration and size predictions made with this method to the read numbers and lengths observed in a sequencing run on the Illumina MiSeq® next generation sequencing system.

The ability of the QuantiSize assay to combine quantification and size determination in a single ddPCR experiment is derived from a correlation between the fluorescence amplitude of droplets and the size of amplicon within them. With standard ddPCR reagent concentrations, DNA amplification is eventually limited by the availability of dNTPs and inhibited by the presence of pyrophosphate (Hori et al., 2007, Biochem. Biophys. Res. Comm. 352:323-328; Xiao et al., 2004, Genome Res. 14:1749-1755); thus long DNA templates, which consume more dNTPs and generate more pyrophosphate, will have produced fewer products than short templates at the endpoint of a standard reaction. Because the final number of products generated within a droplet determines its level of fluorescence, the measured fluorescence amplitude of droplets containing short templates will be greater than that of droplets containing long templates. The QuantiSize assay exploits this fact to generate an equation relating fluorescence amplitude to amplicon size by using measurements of known size standards. The equation describing the relationship between fluorescence amplitude and amplicon size can be used to calculate the size of any unknown ddPCR template that shares common primer and probe binding sites with the size standards. Creating size standards that have primer and probe binding sites in common with DNA samples can be accomplished in a number of ways including cloning sample DNA into a vector and appending adapter sequences to both the sample DNA and size standards (Zhang et al., 2003, Nucleic Acids Res. 31:e123).

A set of size standards applicable to Illumina NGS libraries was created with modified pUC-19 plasmids containing inserts ranging from 25 to 1,000 base pairs flanked on both sides by seven base pair indices and adapter sequences compatible with the Illumina MiSeq® platform. With this setup, both the adapter sequence and the plasmid backbone can serve as primer and probe binding sites common to size standards and sample DNA. A pair of primers and a fluorescent TaqMan® probe were designed to hybridize to the adapter sequences such that the length of the amplicon from each plasmid is 160 base pairs plus the length of the insert (FIG. 10). As the primers and probe are specific to the MiSeq® adapter sequences, only the adapter-ligated molecules that will be amplifiable on the MiSeq® flow cell will be quantified.

Correlation Between Droplet Fluorescence Amplitude and Amplicon Size

Figure 11A:
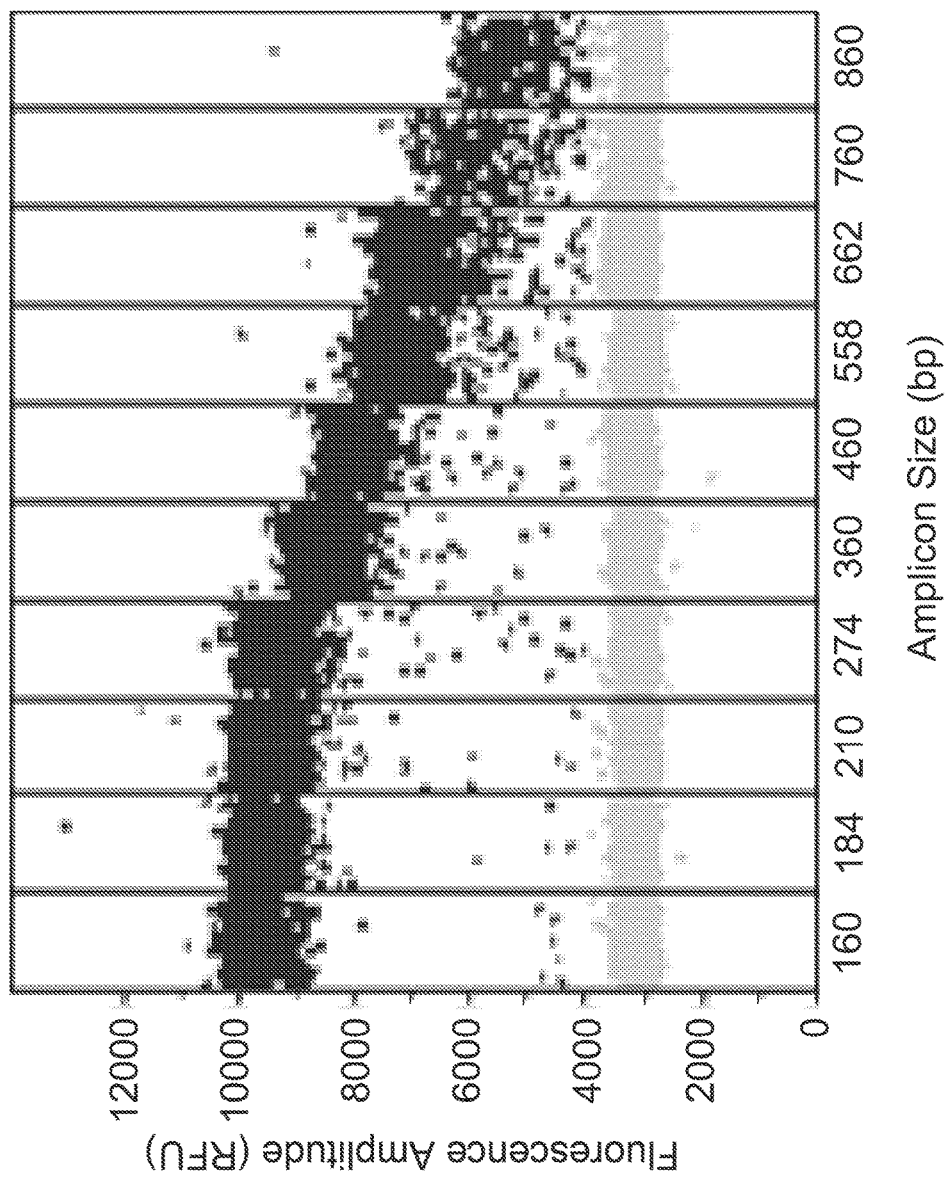
FIG. 11. ddPCR amplification of 10 size standards designed for use with the QuantiSize assay. All size standards were amplified in parallel with standard reagent and thermal cycling conditions. (A) Scatter plot of fluorescence amplitude of individual droplets for each size standard. Droplets whose fluorescence amplitude is above a specified threshold ("positives") are shown in black and droplets with a fluorescence amplitude below the threshold ("negatives") are shown in grey. (B) Box-and-whisker plots showing distribution of fluorescence amplitudes of positive droplets. Horizontal bars mark the mean fluorescence amplitude, boxes mark the interquartile range, and whiskers mark the 95% confidence interval. (C) Plot of mean fluorescence amplitude±SEM versus amplicon size showing a linear correlation ($R^2$=0.9943).
Figure 11B:
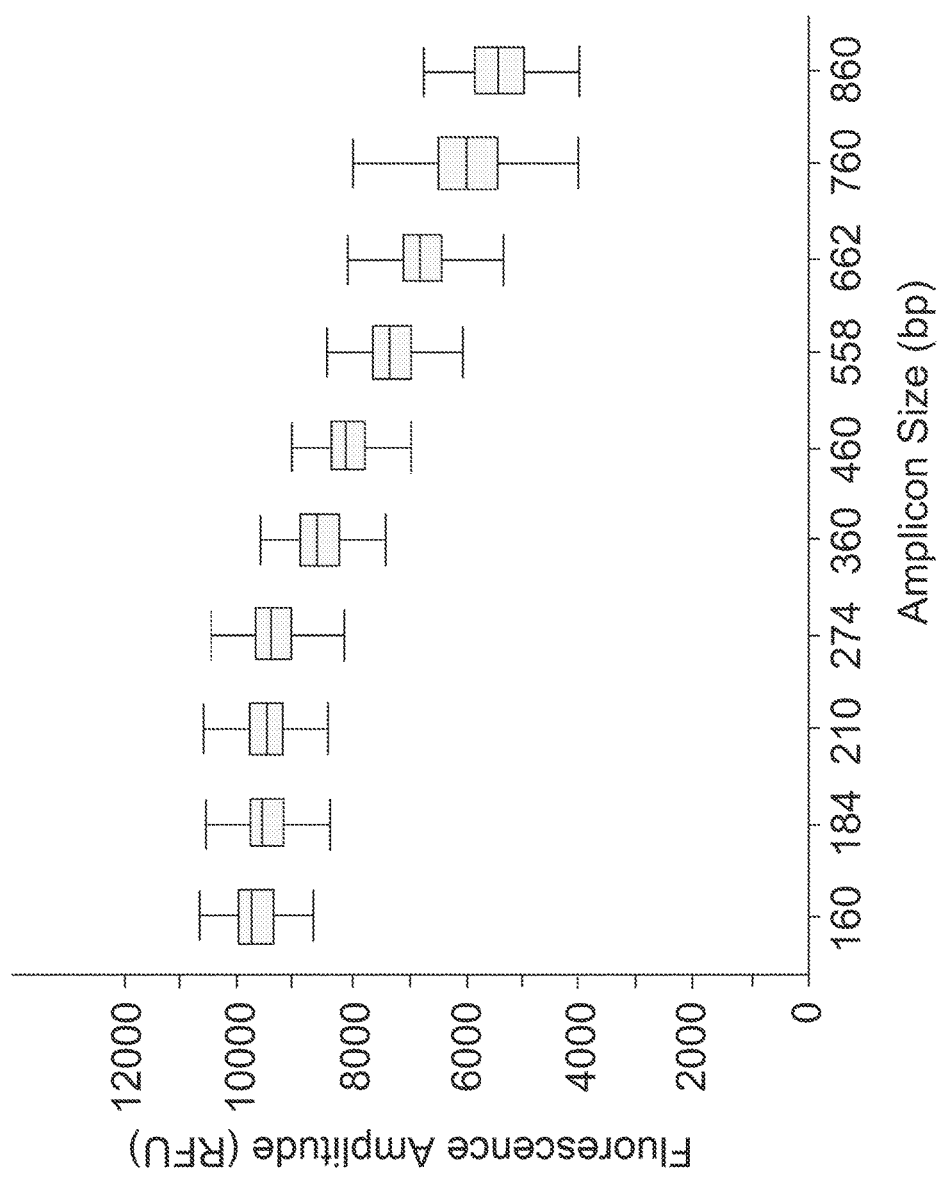
Figure 11C:
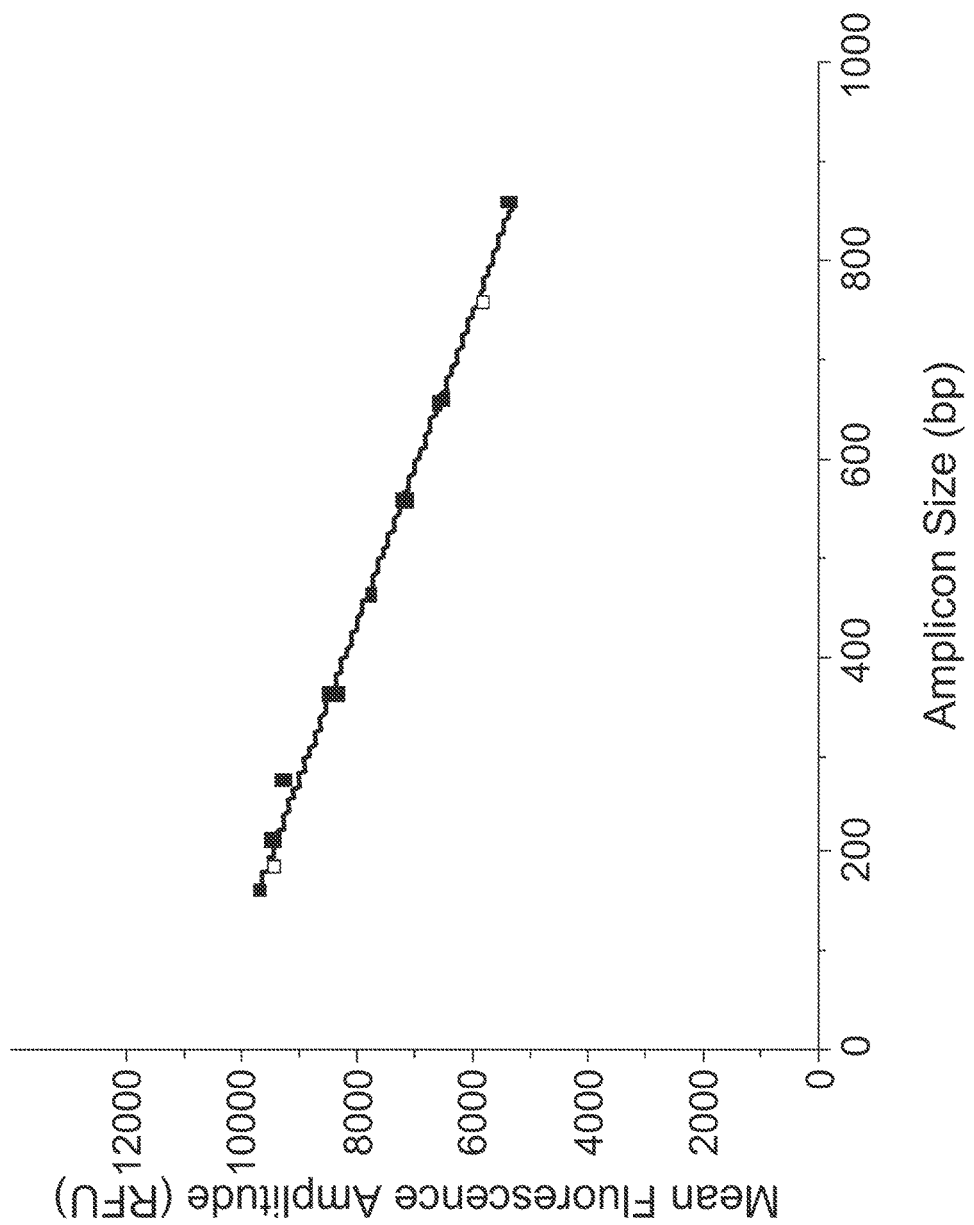

A ddPCR experiment was performed with the aforementioned size standards in separate wells of a 96-well plate. Droplets containing the plasmid target (positive) increased in fluorescence following amplification of the target whereas droplets lacking the target (negative) remained at the background level of fluorescence (FIG. 11A). The distribution of droplet amplitudes is consistent across most amplicon lengths, but the 760 and 860 by amplicons show a broader distribution of amplitudes (FIG. 11B). An inverse, linear correlation between amplicon size and mean fluorescence amplitude was observed ($R^2=0.99436$) (FIG. 11C). The equation describing this correlation allows for the calculation of amplicon size given a measured fluorescence amplitude. The slope of this equation provides a measure of the difference in mean fluorescence amplitude that is expected with a given difference in amplicon size. Maximizing the magnitude of this slope maximizes the resolution of size standards, which is advantageous for the purpose of determining the length of unknown amplicons more accurately.

Improving Assay Conditions

Figure 12:
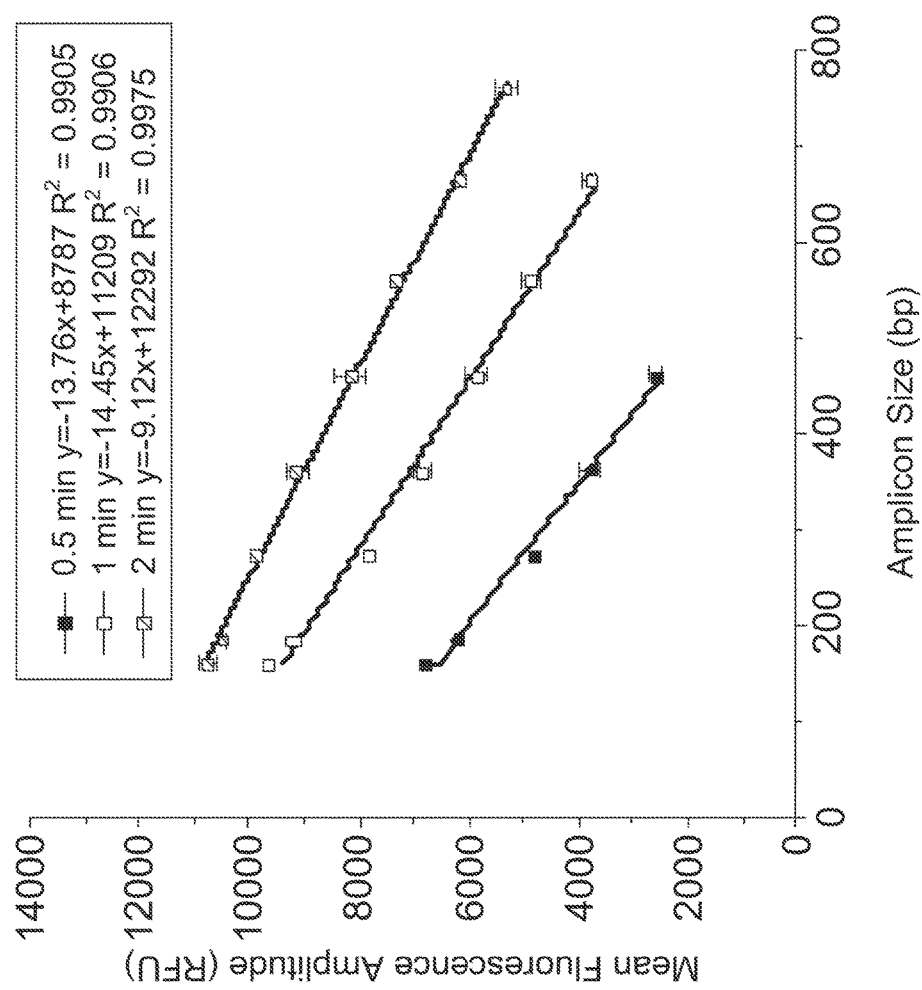
FIG. 12. Effect of ddPCR elongation time on the relationship between fluorescence amplitude±SEM and amplicon size. Three ddPCR experiments were carried out with the same size standards using 0.5, 1, and 2 minute elongation times during droplet thermal cycling. With a 0.5 minute elongation time (black squares), the slope of the regression line relating fluorescence amplitude to amplicon size was −13.760 ($R^2$=0.9905). With a 1 minute elongation time (white squares), the slope was −11.460 ($R^2$=0.9906). With a 2 minute elongation time (diagonal stripe squares), the slope was −9.123 ($R^2$=0.9975). As the magnitude of the slope of the relationship between fluorescence amplitude and amplicon size increases, so does the ability to accurately resolve small differences in amplicon size. Larger templates require longer elongation times for positive droplets to fluoresce discernibly above the background level of droplet fluorescence.

The droplet reader software counts positive and negative droplets by using a threshold of fluorescence between the well-defined populations of high and low fluorescence amplitude droplets. For one particular TaqMan® probe tested, the fluorescence amplitude of droplets containing amplicons larger than 660 by was too low to reliably discriminate between positive and negative droplets when templates are amplified with a one-minute elongation time. When this is the case, the average fluorescence amplitude for these amplicons cannot be calculated. Increasing the elongation time to two minutes increases the fluorescence amplitude of all droplets containing amplifiable template (FIG. 12). This enables the acquisition of accurate concentration and fluorescence amplitude data for longer templates, but the slope of the relationship between amplicon size and fluorescence amplitude is decreased (from m=−11.66 to m=−9.12), which decreases the ability to resolve small differences in amplicon size (FIG. 12). Decreasing the elongation time to 30 seconds increases the resolution of the relationship between amplicon size and fluorescence amplitude, but prevents targets longer than 460 by from amplifying to the point that they fluoresce detectably above the background fluorescence (FIG. 12).

Quantification of MiSeq Libraries with ddPCR

Figure 13:
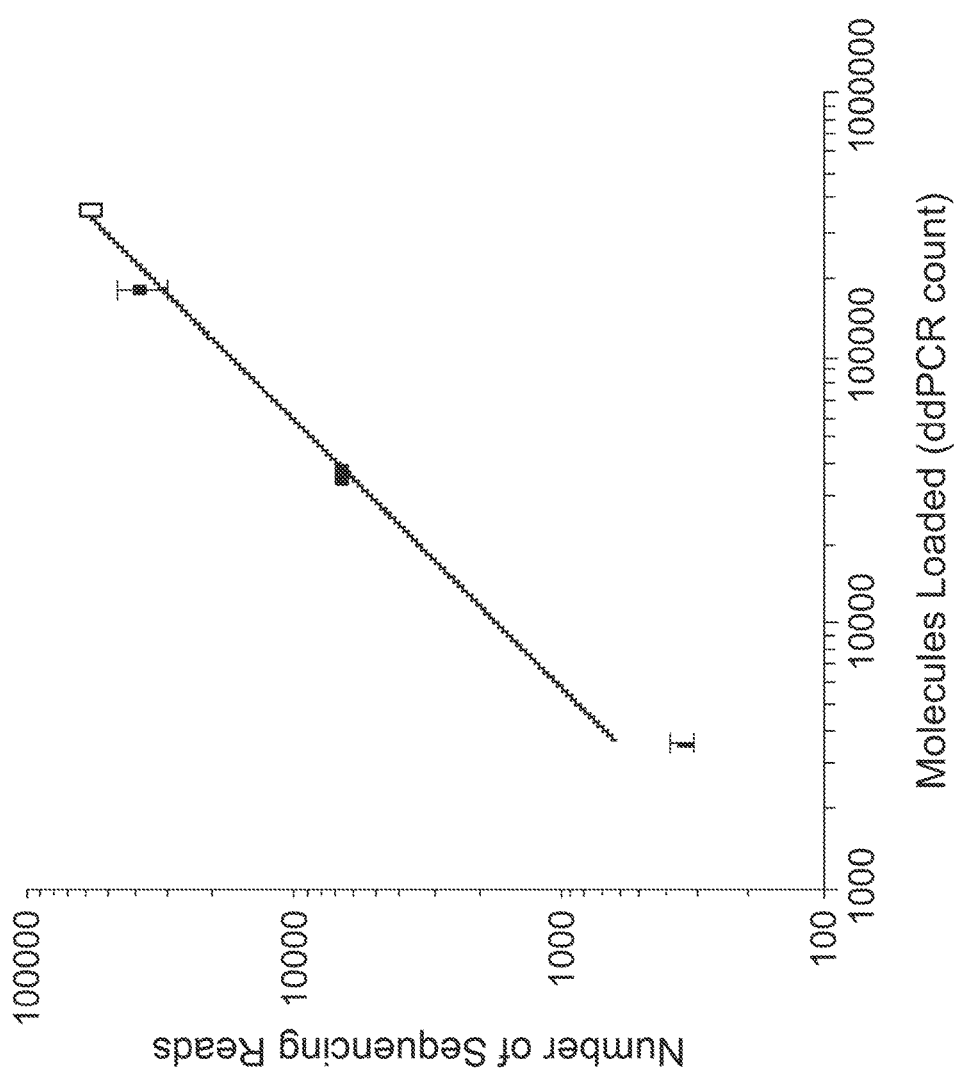
FIG. 13. Number of sequencing reads versus number of molecules loaded as measured by ddPCR. Eight uniquely indexed libraries were loaded onto the MiSeq® with two libraries at each concentration. The libraries were loaded in a concentration ratio of 100:50:10:1 based on ddPCR measurements. Due to the binding kinetics of library molecules on the MiSeq® flow cell, the number of reads generated by the MiSeq® is expected to be a fraction of the number of library molecules loaded. The relative numbers of MiSeq® reads for each library closely correspond to the relative numbers of molecules loaded according to ddPCR measurements ($R^2$=0.9693). Error bars represent the standard error of the mean.

Due to the strong correlation between amplicon size and fluorescence amplitude of droplets, the pJB plasmids containing different sized inserts can be used as size standards to determine the size of unknown amplicons that share the same TagMan® probe binding site. To validate the use of the QuantiSize assay for the sizing and quantification steps in library preparation for NGS, an experiment to compare the quantity and size distribution of library DNA predicted by the QuantiSize assay to the quantity and size distribution observed by using the Illumina MiSeq® platform was performed. The test libraries were generated by ligating sheared pET-23a plasmid DNA into pJB plasmids similar to those used to create the aforementioned size standards, but with different indices flanking the insert site. Eight pJB plasmids with unique indices were used in individual ligation reactions with DNA sheared to an average size of 150 bp. The libraries were run in individual wells of a ddPCR experiment alongside the set of size standards. Using the concentrations measured by ddPCR, the eight uniquely indexed libraries were diluted and combined in a molar ratio of 100:50:10:1 with two libraries at each concentration. The combination of all eight libraries was loaded onto a 150-cycle paired-end MiSeq® run for sequencing. The resulting reads indicated the number and size of DNA fragments binding to the adapter ligated flow cell. The observed number of reads containing each index was compared to the expected number of copies of each uniquely indexed library loaded onto the MiSeq®. The observed ratio of the number of reads containing each index very closely matched the expected ratio of 100:50:10:1 that was measured by ddPCR and the correlation between the expected and actual number of library molecules gave an $R^2$ value of 0.9693 (FIG. 13).

Measurement of MiSeq Library Size Distribution with the QuantiSize Assay

Figure 14:
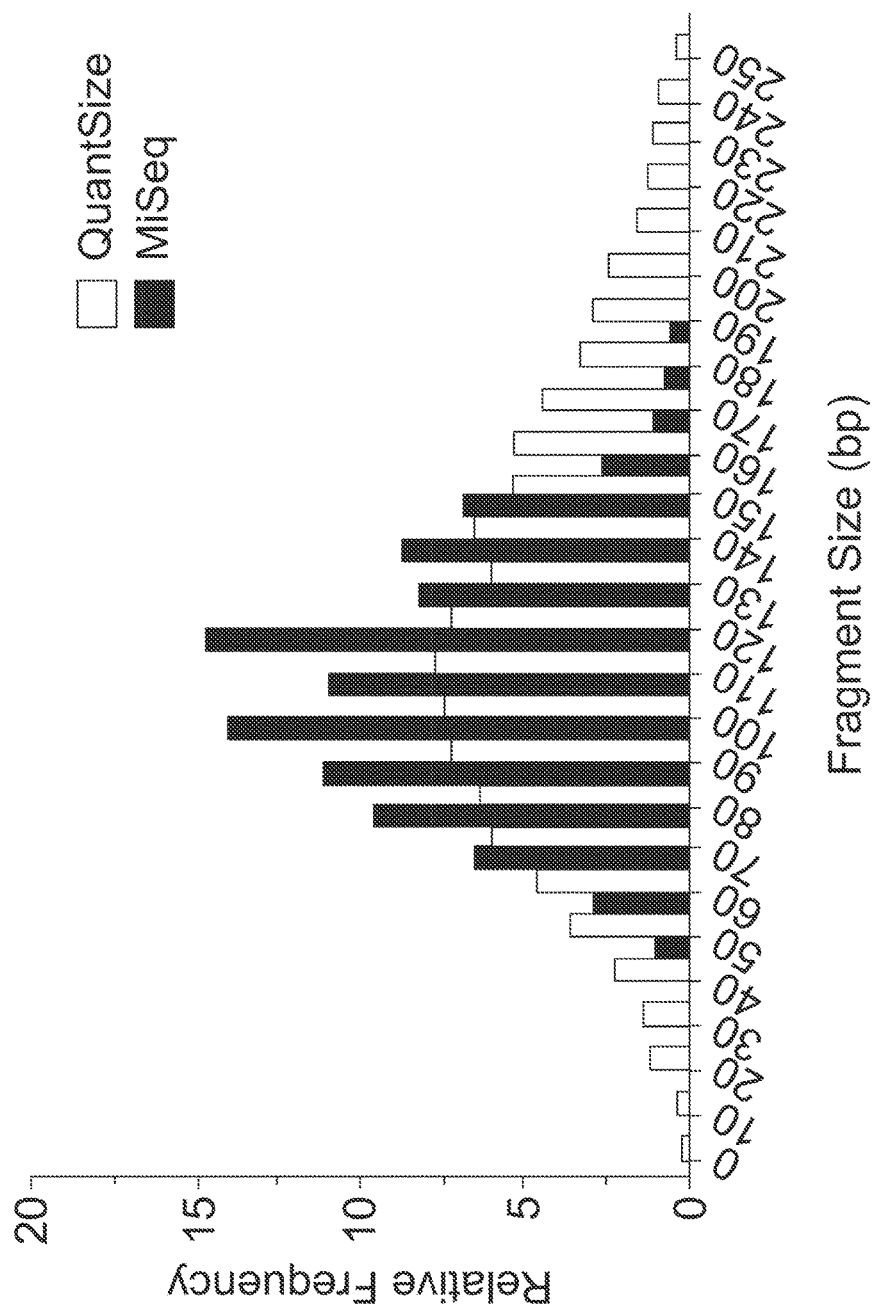
FIG. 14. Comparison of library molecule size distribution. The QuantiSize assay was performed on a DNA library prepared for the MiSeq® in order to predict the distribution of library molecule sizes. The DNA library was amplified in parallel with a set of size standards using the same primers and TaqMan® probe, allowing estimation of the expected amplicon size within each individual droplet. The resulting size distribution is shown in white bars. The actual size distribution was determined through paired-end sequencing on the Illumina MiSeq® system (shown in black bars). Both histograms show the relative frequency of measured molecule sizes in 10 base pair bins. The size distribution measured by QuantiSize is naturally wider than the distribution measured by the MiSeq® due to the inherent variance in droplet amplitude that occurs even with amplicons of the same length. The DNA library was amplified in parallel with a set of size standards using the same primers and TaqMan® probe, allowing us to estimate the expected amplicon size within each individual droplet.

The equation relating amplicon size and fluorescence amplitude can be applied either to the average (mean or median) fluorescence amplitude of a sample or to the fluorescence amplitude of individual droplets. Applying the equation to individual droplets allows for a more detailed analysis of the distribution of product sizes present in a sample. The equation generated by the adapter-ligated size standards was applied to the fluorescence amplitude of individual droplets containing library DNA to calculate the expected amplicon size within each droplet. The size distribution estimated by QuantiSize with individual droplet analysis was compared to the distribution of read sizes measured by the MiSeq® (FIG. 14). The frequency distribution shows a high degree of overlap and a common center point for the estimation made using the QuantiSize assay and the observations from the MiSeq®. As depicted in FIG. 11A, there is an inherent variance in droplet amplitude that occurs even within a completely homogeneous sample of amplicon lengths. This variance likely accounts for the wider distribution of product sizes estimated by ddPCR than were observed in the MiSeq® data. Alternatively, this could be explained by bias on the MiSeq® platform against short and/or long amplicons.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A method for detecting and quantifying frequency of a rare nucleic acid molecule deletion mutation, comprising:
   a. contacting a plurality of nucleic acid molecules with a first restriction endonuclease, wherein the first restriction endonuclease is capable of cleaving a nucleic acid molecule comprising a first target region having two or more restriction sites for the first restriction endonuclease, and wherein the nucleic acid molecule is not cleaved by the first restriction endonuclease at the two or more restriction sites of the first target region when the first target region comprises a first deletion mutation;
   b. amplifying the first target region comprising the first deletion mutation from the plurality of nucleic acid molecules of step (a) with a first 5' primer and a first 3' primer using digital PCR to obtain a number of the first deletion mutation, wherein the first 5' primer and the first 3' primer are complementary to nucleic acid sequences flanking the first target region on the nucleic acid molecule, and only the first target region comprising the first deletion mutation is substantially amplified;
   c. amplifying a control target region from the plurality of nucleic acid molecules of step (a) with a control 5' primer and a control 3' primer using digital PCR to obtain a total number of the plurality of nucleic acid molecules, wherein the control 5' primer and control 3' primer are complementary to nucleic acid sequences flanking the control target region and the control target region does not comprise a restriction site for the first restriction endonuclease; and
   d. obtaining a ratio of the number of the first deletion mutation to the total number of the plurality of nucleic acid molecules;

thereby detecting and quantifying the frequency of the rare nucleic acid molecule deletion mutation of the first target region within the plurality of nucleic acid molecules.

2. The method of claim 1, wherein the nucleic acid molecule comprising the first target region comprising the deletion mutation is a genomic DNA molecule or a mitochondrial DNA molecule.

3. The method of claim 1, wherein the digital PCR amplifying step comprises use of water-in-oil droplets or microfluidic chambers.

4. The method of claim 3, wherein the digital PCR amplifying step comprises use of water-in-oil droplets comprising magnetic beads.

5. The method of claim 1, wherein the amplified first target region comprising the deletion mutation is fluorescently labeled.

6. The method of claim 5, wherein the fluorescence of the amplified first target region comprising the first deletion mutation is detected by flow cytometry.

7. The method of claim 1, wherein the number of the first deletion mutation is calculated by using a Poisson statistical equation according to:

$$\lambda = -\ln(1-p)$$

wherein $\lambda$ is the average number of nucleic acid molecules comprising the first target region comprising the first deletion mutation per reaction chamber and p is the fraction of positive end-point reaction chambers,
wherein $\lambda$ is multiplied by the volume of each reaction chamber and the total number of reaction chambers analyzed to obtain the number of the first deletion mutation.

8. The method of claim 1, wherein the method further comprises determining deletion mutation size, sequence of the deletion mutation, deletion mutation breakpoints, or spectrum of deletion mutations.

9. The method of claim 1, wherein:
the nucleic acid molecule of the contacting step (a) comprises a second target region having two or more restriction sites for the first restriction endonuclease, and the nucleic acid molecule comprising the second target region is not cleaved by the first restriction endonuclease at the two or more restriction sites of the second target region when the second target region comprises a second deletion mutation;
the amplifying step (b) further comprises amplifying the second target region comprising the second deletion mutation from the plurality of nucleic acid molecules with a second 5' primer and a second 3' primer using digital PCR to obtain a number of the second deletion mutation, wherein the second 5' primer and the second 3' primer are complementary to nucleic acid sequences flanking the second target region on the nucleic acid molecule, and only the first target region comprising the first deletion mutation and the second target region comprising the second deletion mutation are substantially amplified; and
a ratio of the number of the second deletion mutation to the total number of the plurality of nucleic acid molecules is obtained;
thereby detecting and quantifying the frequencies of the rare nucleic acid molecule deletion mutations of the first target region and the second target region within the plurality of nucleic acid molecules.

10. The method of claim 1, wherein:
the nucleic acid molecule of the contacting step (a) comprises a plurality of target regions, each target region having two or more restriction sites for the first restriction endonuclease, and the nucleic acid molecule is not cleaved by the first restriction endonuclease at the two or more restriction sites in any target region comprising a deletion mutation;
the amplifying step (b) further comprises amplifying the plurality of target regions with a plurality of 5' primers and a plurality of 3' primers using digital PCR to obtain a number of each deletion mutation, wherein the plurality of 5' primers and 3' primers are complementary to nucleic acid sequences flanking the plurality of target regions on the nucleic acid molecule, and only the plurality of target regions that each comprise the deletion mutation is substantially amplified; and
a ratio of the number of each deletion mutation to the total number of the plurality of nucleic acid molecules is obtained;
thereby detecting and quantifying the frequencies of the rare nucleic acid molecule deletion mutations of the plurality of target regions within the plurality of nucleic acid molecules.

11. The method of claim 1, wherein:
the contacting step (a) comprises contacting the plurality of nucleic acid molecules with a second restriction endonuclease, wherein the second restriction endonuclease is capable of cleaving the nucleic acid molecule comprising a second target region having a two or more restriction sites for the second restriction endonuclease, and wherein the nucleic acid molecule is not cleaved by the second restriction endonuclease at the two or more restriction sites of the second target region when the second target region comprises a second deletion mutation;
the amplifying step (b) further comprises amplifying the second target region comprising the deletion mutation with a second 5' primer and a second 3' primer using digital PCR to obtain a number of the second deletion mutation, wherein the second 5' primer and the second 3' primer are complementary to nucleic acid sequences flanking the second target region on the nucleic acid molecule, and only the first target region comprising the first deletion mutation and the second target region comprising the second deletion mutation are substantially amplified;
the control target region does not comprise a restriction site for the second restriction endonuclease; and
a ratio of the number of the second deletion mutation to the total number of the plurality of nucleic acid molecules is obtained;
thereby detecting and quantifying the frequency of the rare nucleic acid molecule deletion mutations of the first target region and second target region within the plurality of nucleic acid molecules.

12. The method of claim 11, wherein:
the nucleic acid molecule of the contacting step (a) comprises a plurality of target regions, each target region having two or more restriction sites for the second restriction endonuclease, and the nucleic acid molecule is not cleaved by the second restriction endonuclease at the two or more restriction sites in any target region comprising a deletion mutation;
the amplifying step (b) further comprises amplifying the plurality of target regions with a plurality of 5' primers and a plurality of 3' primers using digital PCR to obtain a number of each deletion mutation, wherein the plurality of 5' primers and 3' primers are complementary to nucleic acid sequences flanking the plurality of target regions on the nucleic acid molecule, and only the first target region comprising the deletion mutation and the plurality of target regions that each comprise the deletion mutation are substantially amplified; and
a ratio of the number of each deletion mutation to the total number of the plurality of nucleic acid molecules is obtained;
thereby detecting and quantifying the frequency of the rare nucleic acid molecule deletion mutations of the first target region and the plurality of target regions within the plurality of nucleic acid molecules.

13. A method for determining the size of a nucleic acid molecule, comprising:
a. amplifying a nucleic acid molecule using digital PCR in a water-in-oil droplet to produce a target amplicon;
b. measuring the fluorescence value of a positive droplet containing target amplicon; and
c. comparing the fluorescence value of the positive droplet containing the target amplicon to the fluorescence values of at least two control amplicons of known size, thereby determining the size of the nucleic acid molecule.

14. The method of claim 13, wherein the nucleic acid molecule comprises a molecule having a formula of, from 5' to 3', $X^a$-Y-$X^b$, wherein:
a. $X^a$ comprises a first primer annealing site;
b. Y comprises the nucleic acid molecule; and
c. $X^b$ comprises a second primer annealing site.

15. The method of claim 13, wherein the nucleic acid molecule contains a template to generate a target amplicon.

16. The method of claim 14, wherein $X^a$ comprises a first adapter sequence that comprises the first primer annealing site and $X^b$ comprises a second adapter sequence that comprises the second primer annealing site.

17. The method of claim 14, wherein the nucleic acid molecule further comprises a first index sequence disposed between $X^a$ and Y, and a second index sequence disposed between Y and $X^b$.

18. The method of claim 13, wherein the target amplicon and control amplicons are amplified with a first primer and a second primer, and the target amplicon and control amplicons are detected with a first fluorogenic probe.

19. The method of claim 3, wherein the digital PCR amplifying step comprises partitioning the plurality of nucleic acid molecules into nanoliter water-in-oil droplets, or picoliter water-in-oil droplets, following the contacting step and prior to the digital PCR amplifying step.

20. The method of claim 13, wherein the digital PCR amplifying step comprises partitioning the plurality of nucleic acid molecules into nanoliter water-in-oil droplets or picoliter water-in-oil droplets.

21. The method of claim 13, wherein the fluorescence value of the positive droplet containing the target amplicon is correlated with the target amplicon size.

22. The method of claim 21, wherein the fluorescence value of the positive droplet containing the target amplicon is inversely correlated with the target amplicon size.

23. The method of claim 13, wherein the nucleic acid molecule comprises a deletion mutation or copy number variation.

24. A method of determining the sizes of a plurality of nucleic acid molecules according to claim 13, further comprising:
   a. amplifying a plurality of nucleic acid molecules using digital PCR in water-in-oil droplets to produce a plurality of target amplicons;
   b. measuring the fluorescence values of positive droplets containing the target amplicons; and
   c. comparing the fluorescence values of the positive droplets containing the target amplicons to the fluorescence values of at least two control amplicons of known size,
   thereby determining the sizes of the plurality of nucleic acid molecules.

* * * * *

SEQUENCE LISTING

<160> NUMBER OF SEQ ID NOS: 19

<210> SEQ ID NO 1
<211> LENGTH: 35
<212> TYPE: DNA
<213> ORGANISM: Artificial Sequence
<220> FEATURE:
<223> OTHER INFORMATION: Primer sequence

<400> SEQUENCE: 1
gcacaatgtt tcctttgccc gagctcatat caggg                    35

<210> SEQ ID NO 2
<211> LENGTH: 35
<212> TYPE: DNA
<213> ORGANISM: Artificial Sequence
<220> FEATURE:
<223> OTHER INFORMATION: Primer sequence

<400> SEQUENCE: 2
ccctgatatg agctcgggca aaggaaacat tgtgc                              35

<210> SEQ ID NO 3
<211> LENGTH: 20
<212> TYPE: DNA
<213> ORGANISM: Artificial Sequence
<220> FEATURE:
<223> OTHER INFORMATION: Primer sequence

<400> SEQUENCE: 3
gacacaaact aaaaagctca                                               20

<210> SEQ ID NO 4
<211> LENGTH: 20
<212> TYPE: DNA
<213> ORGANISM: Artificial Sequence
<220> FEATURE:
<223> OTHER INFORMATION: Primer sequence

<400> SEQUENCE: 4
acattactgc aggacactta                                               20

<210> SEQ ID NO 5
<211> LENGTH: 22
<212> TYPE: DNA
<213> ORGANISM: Artificial Sequence
<220> FEATURE:
<223> OTHER INFORMATION: Probe sequence
<220> FEATURE:
<221> NAME/KEY: modified_base
<222> LOCATION: (1)...(1)
<223> OTHER INFORMATION: 6FAM fluorophore covalently attached
<220> FEATURE:
<221> NAME/KEY: modified_base
<222> LOCATION: (22)...(22)
<223> OTHER INFORMATION: MGB quencher covalently attached

<400> SEQUENCE: 5
ccaatggcat tagcagtccg gc                                            22

<210> SEQ ID NO 6
<211> LENGTH: 20
<212> TYPE: DNA
<213> ORGANISM: Artificial Sequence
<220> FEATURE:
<223> OTHER INFORMATION: Primer sequence

<400> SEQUENCE: 6
aggccaccac actcctattg                                               20

<210> SEQ ID NO 7
<211> LENGTH: 20
<212> TYPE: DNA
<213> ORGANISM: Artificial Sequence
<220> FEATURE:
<223> OTHER INFORMATION: Primer sequence

<400> SEQUENCE: 7
aatgctaggc gtttgattgg                                         20

<210> SEQ ID NO 8
<211> LENGTH: 21
<212> TYPE: DNA
<213> ORGANISM: Artificial Sequence
<220> FEATURE:
<223> OTHER INFORMATION: Probe sequence
<220> FEATURE:
<221> NAME/KEY: modified_base
<222> LOCATION: (1)...(1)
<223> OTHER INFORMATION: 6FAM fluorophore covalently attached
<220> FEATURE:
<221> NAME/KEY: modified_base
<222> LOCATION: (21)...(21)
<223> OTHER INFORMATION: MGB quencher covalently attached

<400> SEQUENCE: 8
aaggactacg atatggtata a                                       21

<210> SEQ ID NO 9
<211> LENGTH: 16
<212> TYPE: DNA
<213> ORGANISM: Artificial Sequence
<220> FEATURE:
<223> OTHER INFORMATION: Probe sequence
<220> FEATURE:
<221> NAME/KEY: modified_base
<222> LOCATION: (1)...(1)
<223> OTHER INFORMATION: 6FAM fluorophore covalently attached
<220> FEATURE:
<221> NAME/KEY: modified_base
<222> LOCATION: (16)...(16)
<223> OTHER INFORMATION: MGB quencher covalently attached

<400> SEQUENCE: 9
tgaggtctgg gtcatt                                             16

<210> SEQ ID NO 10
<211> LENGTH: 20
<212> TYPE: DNA
<213> ORGANISM: Artificial Sequence
<220> FEATURE:
<223> OTHER INFORMATION: Primer sequence

<400> SEQUENCE: 10
caataaccct acccctagcc                                         20

<210> SEQ ID NO 11
<211> LENGTH: 20
<212> TYPE: DNA
<213> ORGANISM: Artificial Sequence
<220> FEATURE:
<223> OTHER INFORMATION: Primer sequence

<400> SEQUENCE: 11
gtcagtttcc aaagcctcca                                         20

<210> SEQ ID NO 12
<211> LENGTH: 20
<212> TYPE: DNA
<213> ORGANISM: Artificial Sequence
<220> FEATURE:
<223> OTHER INFORMATION: Probe sequence
<220> FEATURE:
<221> NAME/KEY: modified_base
<222> LOCATION: (1)...(1)
<223> OTHER INFORMATION: 6FAM fluorophore covalently attached
<220> FEATURE:
<221> NAME/KEY: modified_base

```
<222> LOCATION: (20)...(20)
<223> OTHER INFORMATION: MGB quencher covalently attached

<400> SEQUENCE: 12
actagtatat cctaaacttc                                              20

<210> SEQ ID NO 13
<211> LENGTH: 19
<212> TYPE: DNA
<213> ORGANISM: Artificial Sequence
<220> FEATURE:
<223> OTHER INFORMATION: Probe sequence
<220> FEATURE:
<221> NAME/KEY: modified_base
<222> LOCATION: (1)...(1)
<223> OTHER INFORMATION: 6FAM fluorophore covalently attached
<220> FEATURE:
<221> NAME/KEY: modified_base
<222> LOCATION: (19)...(19)
<223> OTHER INFORMATION: MGB quencher covalently attached

<400> SEQUENCE: 13
tgcttttgtt ataattttc                                               19

<210> SEQ ID NO 14
<211> LENGTH: 34
<212> TYPE: DNA
<213> ORGANISM: Artificial Sequence
<220> FEATURE:
<223> OTHER INFORMATION: Primer sequence

<400> SEQUENCE: 14
ctaaaaatat taaacacaaa ctaccaccta cctc                              34

<210> SEQ ID NO 15
<211> LENGTH: 30
<212> TYPE: DNA
<213> ORGANISM: Artificial Sequence
<220> FEATURE:
<223> OTHER INFORMATION: Primer sequence

<400> SEQUENCE: 15
gttcattttg gttctcaggg tttgttataa                                   30

<210> SEQ ID NO 16
<211> LENGTH: 17
<212> TYPE: DNA
<213> ORGANISM: Artificial Sequence
<220> FEATURE:
<223> OTHER INFORMATION: Probe sequence
<220> FEATURE:
<221> NAME/KEY: modified_base
<222> LOCATION: (1)...(1)
<223> OTHER INFORMATION: 6FAM fluorophore covalently attached
<220> FEATURE:
<221> NAME/KEY: modified_base
<222> LOCATION: (17)...(17)
<223> OTHER INFORMATION: MGB quencher covalently attached

<400> SEQUENCE: 16
cctcaccaaa gcccata                                                 17

<210> SEQ ID NO 17
<211> LENGTH: 19
<212> TYPE: DNA
<213> ORGANISM: Artificial Sequence
<220> FEATURE:
<223> OTHER INFORMATION: Primer sequence
```

```
<400> SEQUENCE: 17
cgccacatct accatcacc                                                    19

<210> SEQ ID NO 18
<211> LENGTH: 20
<212> TYPE: DNA
<213> ORGANISM: Artificial Sequence
<220> FEATURE:
<223> OTHER INFORMATION: Primer sequence

<400> SEQUENCE: 18
gattatggat gcggttgctt                                                   20

<210> SEQ ID NO 19
<211> LENGTH: 17
<212> TYPE: DNA
<213> ORGANISM: Artificial Sequence
<220> FEATURE:
<223> OTHER INFORMATION: Probe sequence
<220> FEATURE:
<221> NAME/KEY: modified_base
<222> LOCATION: (1)...(1)
<223> OTHER INFORMATION: 6FAM fluorophore covalently attached
<220> FEATURE:
<221> NAME/KEY: modified_base
<222> LOCATION: (17)...(17)
<223> OTHER INFORMATION: MGB quencher covalently attached

<400> SEQUENCE: 19
ttgatggcag cttctgt                                                      17
```